(12) United States Patent
Keegan et al.

(10) Patent No.: US 7,651,496 B2
(45) Date of Patent: Jan. 26, 2010

(54) METHODS AND APPARATUSES FOR PERCUTANEOUS IMPLANT DELIVERY

(75) Inventors: Thomas E. Keegan, North Easton, MA (US); John Matthew Lessin, Vallejo, CA (US); Gene P. DiPoto, Upton, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 556 days.

(21) Appl. No.: 11/184,568

(22) Filed: Jul. 19, 2005

(65) Prior Publication Data

US 2006/0030850 A1 Feb. 9, 2006

Related U.S. Application Data

(60) Provisional application No. 60/590,986, filed on Jul. 23, 2004.

(51) Int. Cl.
*A61F 5/00* (2006.01)
(52) U.S. Cl. .................. 606/60; 606/86 R; 128/898
(58) Field of Classification Search .............. 606/61, 606/86 R, 60; 623/17.11–17.16; 128/898; 600/219; 604/104
See application file for complete search history.

(56) References Cited

U.S. PATENT DOCUMENTS

| | | | |
|---|---|---|---|
| 4,863,133 A | 9/1989 | Bonnell | |
| 5,163,949 A | 11/1992 | Bonutti | |
| 5,171,279 A | 12/1992 | Mathews | |
| 5,197,971 A | 3/1993 | Bonutti | |
| 5,242,443 A | 9/1993 | Kambin | |
| 5,295,994 A | 3/1994 | Bonutti | |
| 5,345,927 A | 9/1994 | Bonutti | |
| 5,354,311 A | 10/1994 | Kambin et al. | |
| 5,357,983 A | 10/1994 | Mathews | |
| 5,370,647 A * | 12/1994 | Graber et al. | ............... 606/127 |
| 5,454,365 A | 10/1995 | Bonutti | |
| 5,496,322 A | 3/1996 | Mathews | |
| 5,569,248 A | 10/1996 | Mathews | |
| 5,601,590 A | 2/1997 | Bonutti et al. | |
| 5,667,520 A | 9/1997 | Bonutti | |
| 5,695,448 A | 12/1997 | Kimura | |
| 5,728,097 A | 3/1998 | Mathews | |
| 5,762,629 A | 6/1998 | Kambin | |
| 5,792,044 A | 8/1998 | Foley | |
| 5,902,231 A | 5/1999 | Foley | |
| 5,961,499 A | 10/1999 | Bonutti et al. | |

(Continued)

FOREIGN PATENT DOCUMENTS

| | | |
|---|---|---|
| WO | WO 02/09801 | 2/2002 |
| WO | 2003068083 | 8/2003 |
| WO | 2004021899 | 3/2004 |
| WO | 2004022108 | 3/2004 |
| WO | 2004103188 | 12/2004 |

(Continued)

*Primary Examiner*—Pedro Philogene
(74) *Attorney, Agent, or Firm*—Crompton, Seager & Tufte, LLC.

(57) ABSTRACT

A method for treating the spine. A guidewire is advanced through the skin of a patient along a percutaneous path to a target location of a vertebra. An implant is advanced over the guidewire to the target location of the vertebra. The implant is coupled with the vertebra at the target location. An elongate body having a proximal end and a distal end is advanced until the distal end is adjacent the target location, the elongate body having an inner surface defining a passage extending therethrough. A procedure is performed at the target location.

26 Claims, 47 Drawing Sheets

U.S. PATENT DOCUMENTS

| | | |
|---|---|---|
| 5,976,146 A | 11/1999 | Ogawa |
| 6,033,406 A | 3/2000 | Mathews |
| 6,120,434 A | 9/2000 | Kimura |
| 6,171,299 B1 | 1/2001 | Bonutti |
| 6,187,000 B1 * | 2/2001 | Davison et al. .............. 606/1 |
| 6,193,715 B1 | 2/2001 | Wrublewski et al. |
| 6,235,028 B1 | 5/2001 | Brumfield et al. |
| 6,258,089 B1 | 7/2001 | Campbell et al. |
| 6,261,291 B1 | 7/2001 | Talaber et al. |
| 6,267,763 B1 | 7/2001 | Castro |
| 6,338,730 B1 | 1/2002 | Bonutti et al. |
| 6,358,266 B1 | 3/2002 | Bonutti |
| 6,361,488 B1 | 3/2002 | Davison et al. |
| 6,361,537 B1 | 3/2002 | Anderson |
| 6,371,968 B1 | 4/2002 | Kogasaka et al. |
| 6,383,195 B1 * | 5/2002 | Richard ............... 606/114 |
| 6,485,518 B1 | 11/2002 | Cornwall et al. |
| 6,524,320 B2 * | 2/2003 | DiPoto ............... 606/108 |
| 6,530,880 B2 | 3/2003 | Pagliuca |
| 6,530,929 B1 | 3/2003 | Justis et al. |
| 6,599,290 B2 | 7/2003 | Bailey et al. |
| 6,602,255 B1 | 8/2003 | Campbell et al. |
| 6,626,907 B2 | 9/2003 | Campbell et al. |
| 6,648,888 B1 | 11/2003 | Shluzas |
| 6,652,553 B2 | 11/2003 | Davison et al. |
| 6,749,614 B2 | 6/2004 | Teitelbaum et al. |
| 6,755,833 B1 | 6/2004 | Paul et al. |
| 6,793,656 B1 | 9/2004 | Mathews |
| 6,800,084 B2 | 10/2004 | Davison et al. |
| 6,821,243 B2 | 11/2004 | Pagliuca et al. |
| 6,821,277 B2 | 11/2004 | Teitelbaum |
| 6,837,889 B2 | 1/2005 | Shluzas |
| 6,875,212 B2 | 4/2005 | Shaolian et al. |
| 7,004,947 B2 | 2/2006 | Shluzas et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,056,321 B2 | 6/2006 | Pagliuca |
| 7,066,937 B2 | 6/2006 | Shluzas |
| 7,144,393 B2 | 12/2006 | DiPoto |
| 7,179,225 B2 | 2/2007 | Shluzas et al. |
| 7,226,451 B2 * | 6/2007 | Shluzas et al. .............. 606/86 |
| 2002/0068975 A1 | 6/2002 | Teitelbaum et al. |
| 2002/0082598 A1 | 6/2002 | Teitelbaum |
| 2002/0082600 A1 | 6/2002 | Shaolian et al. |
| 2002/0161368 A1 | 10/2002 | Foley et al. |
| 2002/0198526 A1 | 12/2002 | Shaolian et al. |
| 2003/0014068 A1 | 1/2003 | Bonutti et al. |
| 2003/0060826 A1 | 3/2003 | Foley |
| 2003/0229347 A1 | 12/2003 | Sherman et al. |
| 2004/0087951 A1 | 5/2004 | Khalili |
| 2004/0097907 A1 | 5/2004 | DiPoto |
| 2004/0133201 A1 | 7/2004 | Shluzas |
| 2004/0138662 A1 | 7/2004 | Landry et al. |
| 2004/0143265 A1 | 7/2004 | Landry et al. |
| 2004/0153069 A1 | 8/2004 | Paul |
| 2004/0158245 A1 | 8/2004 | Chin |
| 2004/0172022 A1 | 9/2004 | Landry et al. |
| 2004/0215190 A1 | 10/2004 | Nguyen et al. |
| 2004/0215193 A1 | 10/2004 | Shaolian et al. |
| 2004/0230100 A1 | 11/2004 | Shluzas |
| 2005/0010227 A1 | 1/2005 | Paul |
| 2005/0021031 A1 | 1/2005 | Foley et al. |
| 2005/0021032 A1 | 1/2005 | Koo |
| 2005/0033434 A1 | 2/2005 | Berry |
| 2005/0038432 A1 | 2/2005 | Shaolian et al. |
| 2005/0038434 A1 | 2/2005 | Mathews |
| 2005/0065515 A1 | 3/2005 | Jahng |
| 2005/0065516 A1 | 3/2005 | Jahng |
| 2005/0065517 A1 | 3/2005 | Chin |
| 2005/0070901 A1 | 3/2005 | David |
| 2005/0070917 A1 | 3/2005 | Justis |
| 2005/0075644 A1 | 4/2005 | DiPoto et al. |
| 2005/0085813 A1 | 4/2005 | Spitler et al. |
| 2005/0090822 A1 | 4/2005 | DiPoto |
| 2005/0090833 A1 | 4/2005 | DiPoto |
| 2005/0131408 A1 | 6/2005 | Sicvol et al. |
| 2005/0149022 A1 | 7/2005 | Shaolian et al. |
| 2005/0154389 A1 | 7/2005 | Selover et al. |
| 2005/0165398 A1 | 7/2005 | Reiley |
| 2005/0171540 A1 | 8/2005 | Lim et al. |
| 2005/0171551 A1 | 8/2005 | Sukovich et al. |
| 2005/0215999 A1 | 9/2005 | Birkmeyer et al. |
| 2005/0245928 A1 | 11/2005 | Colleran et al. |
| 2005/0245942 A1 | 11/2005 | DiPoto |
| 2005/0251139 A1 | 11/2005 | Roh |
| 2005/0251140 A1 | 11/2005 | Shaolian et al. |
| 2005/0251192 A1 | 11/2005 | Shluzas et al. |
| 2005/0273131 A1 | 12/2005 | Shluzas et al. |
| 2005/0273132 A1 | 12/2005 | Shluzas et al. |
| 2005/0277934 A1 | 12/2005 | Vardiman |
| 2006/0084985 A1 | 4/2006 | Kim |
| 2006/0084987 A1 | 4/2006 | Kim |
| 2006/0084993 A1 | 4/2006 | Landry et al. |
| 2006/0085069 A1 | 4/2006 | Kim |
| 2006/0111712 A1 | 5/2006 | Jackson |
| 2006/0111713 A1 | 5/2006 | Jackson |
| 2006/0111714 A1 | 5/2006 | Foley |
| 2006/0111715 A1 | 5/2006 | Jackson |
| 2006/0147276 A1 | 6/2006 | Landry |

FOREIGN PATENT DOCUMENTS

| | | |
|---|---|---|
| WO | WO 2005/011508 A1 | 2/2005 |
| WO | WO 2005/013864 A2 | 2/2005 |
| WO | 2005018466 | 3/2005 |
| WO | 2005046492 | 3/2005 |
| WO | WO 2005/032358 A2 | 4/2005 |
| WO | WO 2005/072081 A2 | 8/2005 |

* cited by examiner

FIG.2
FIG.3
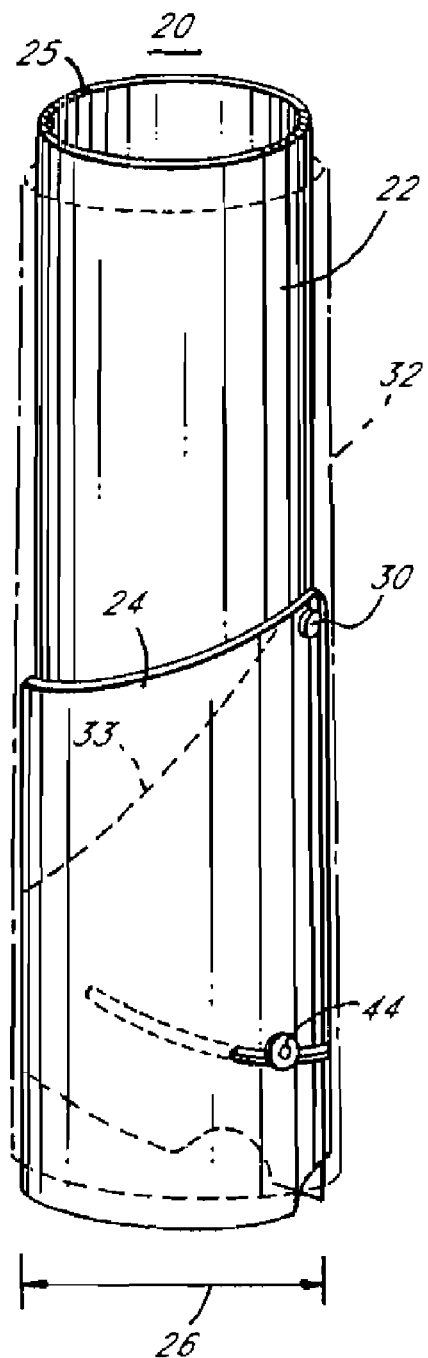
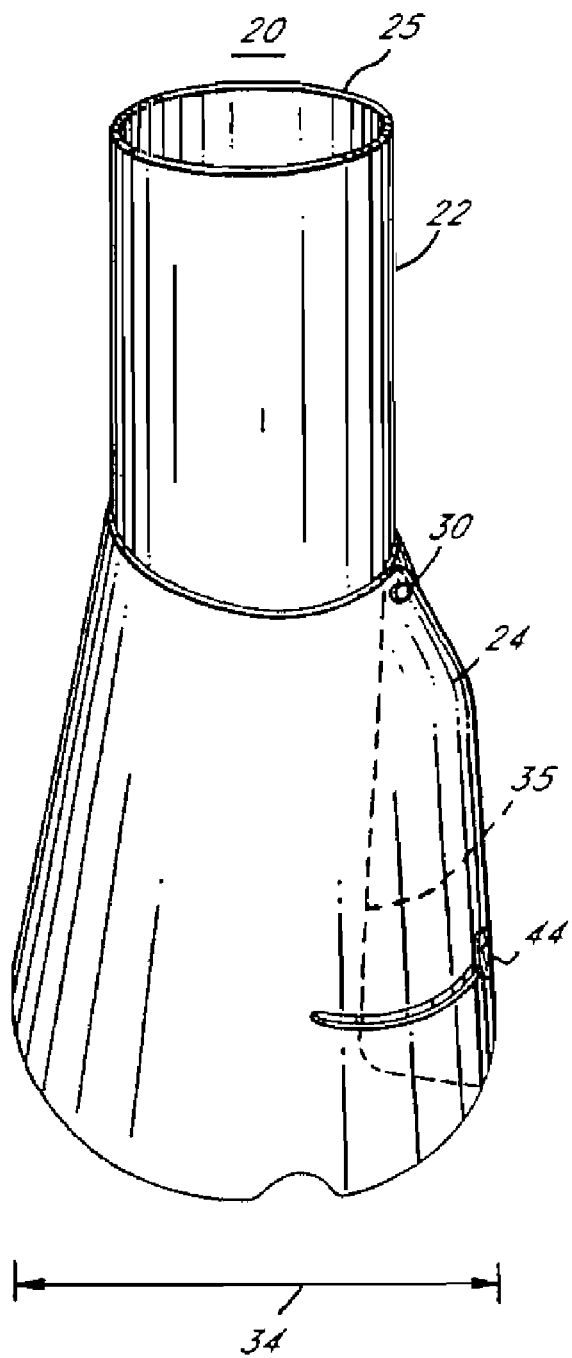

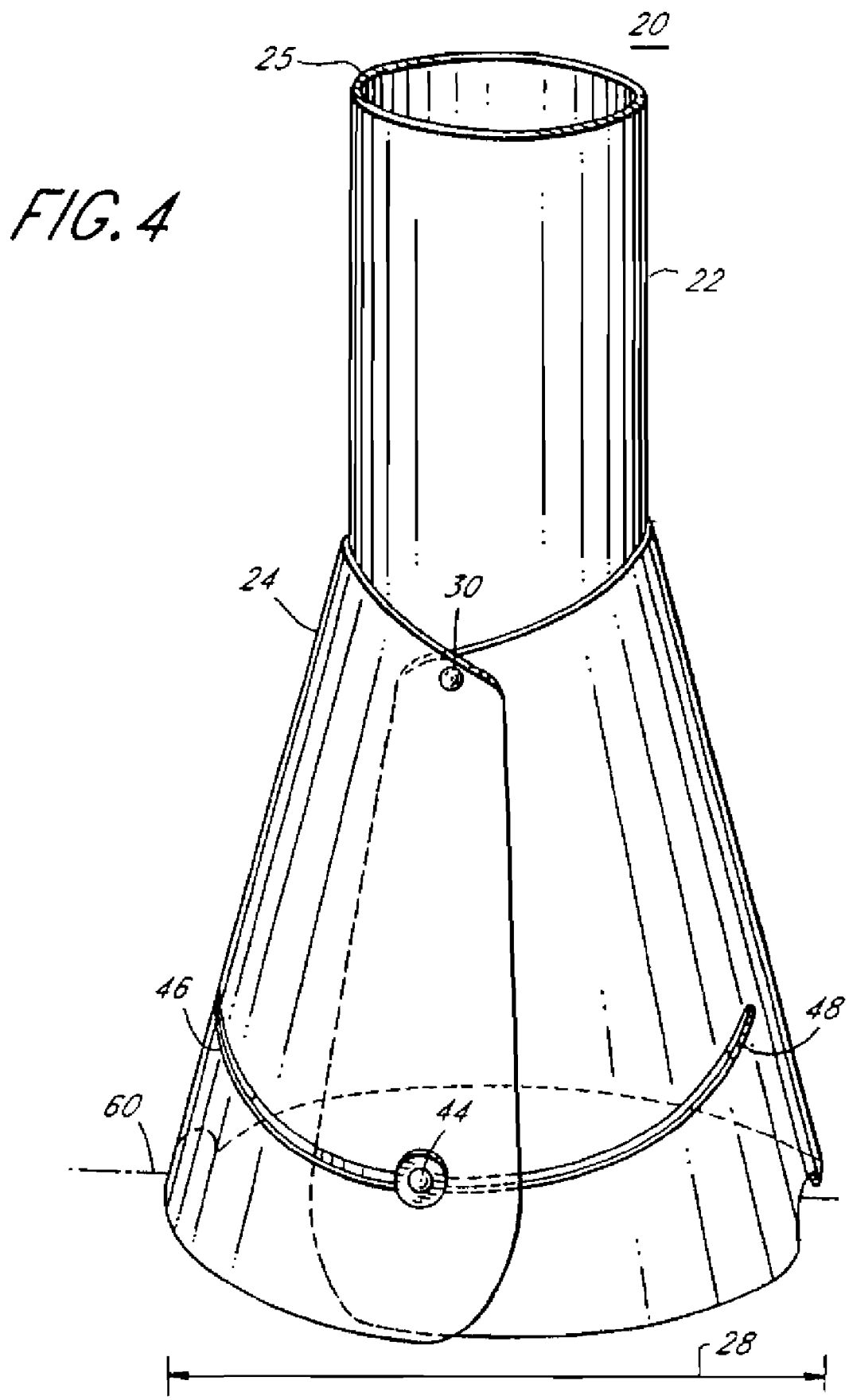

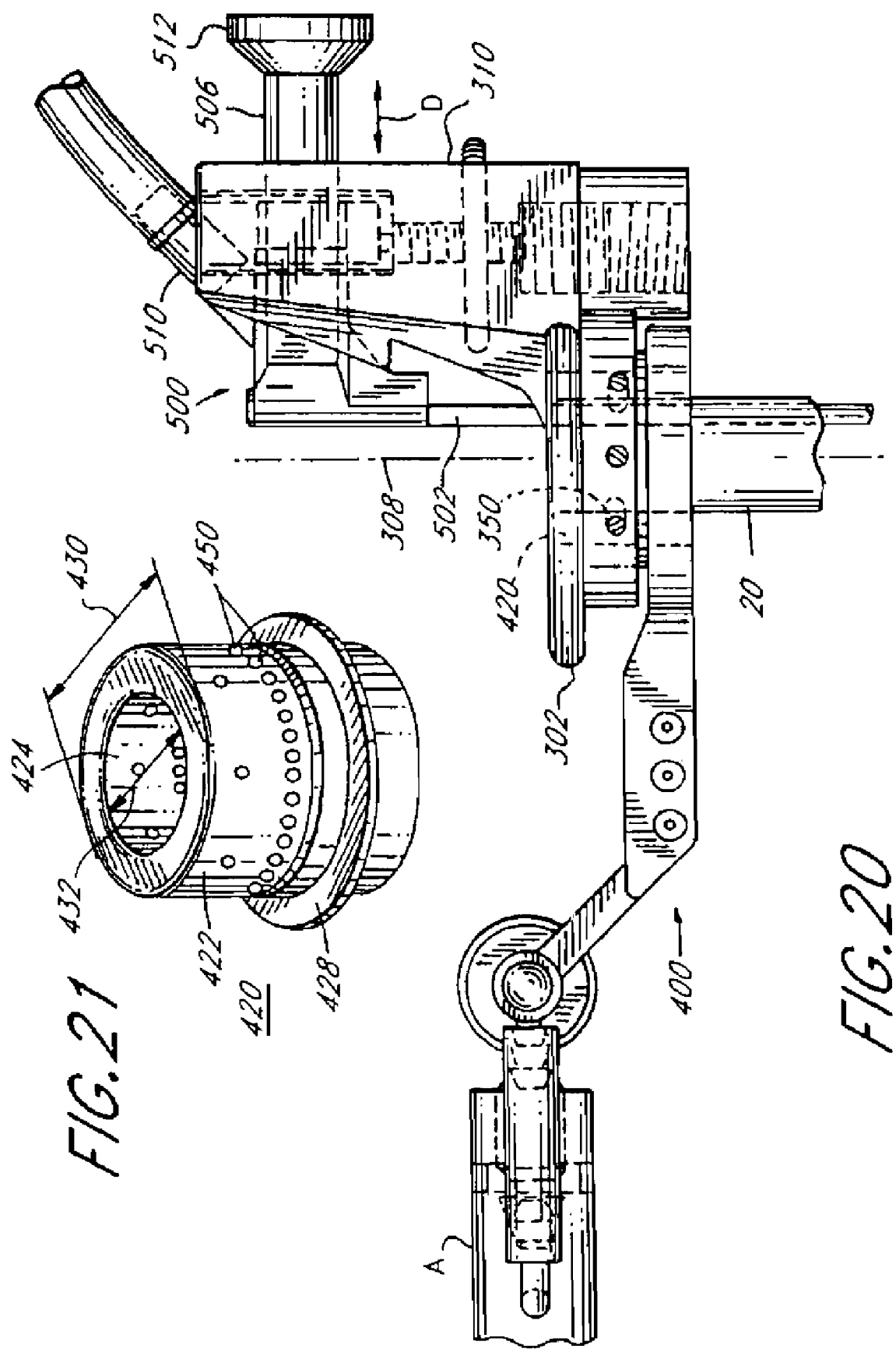

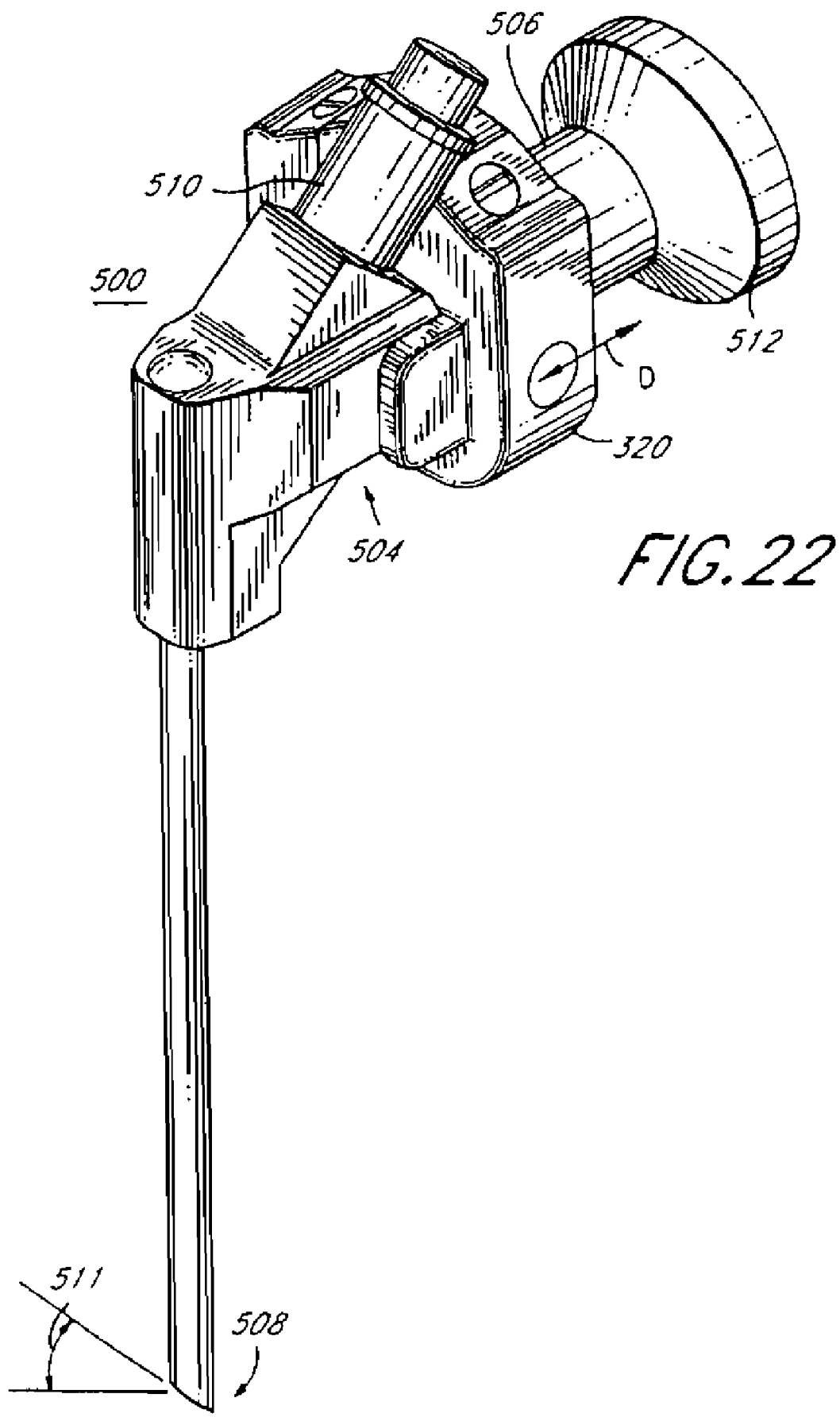

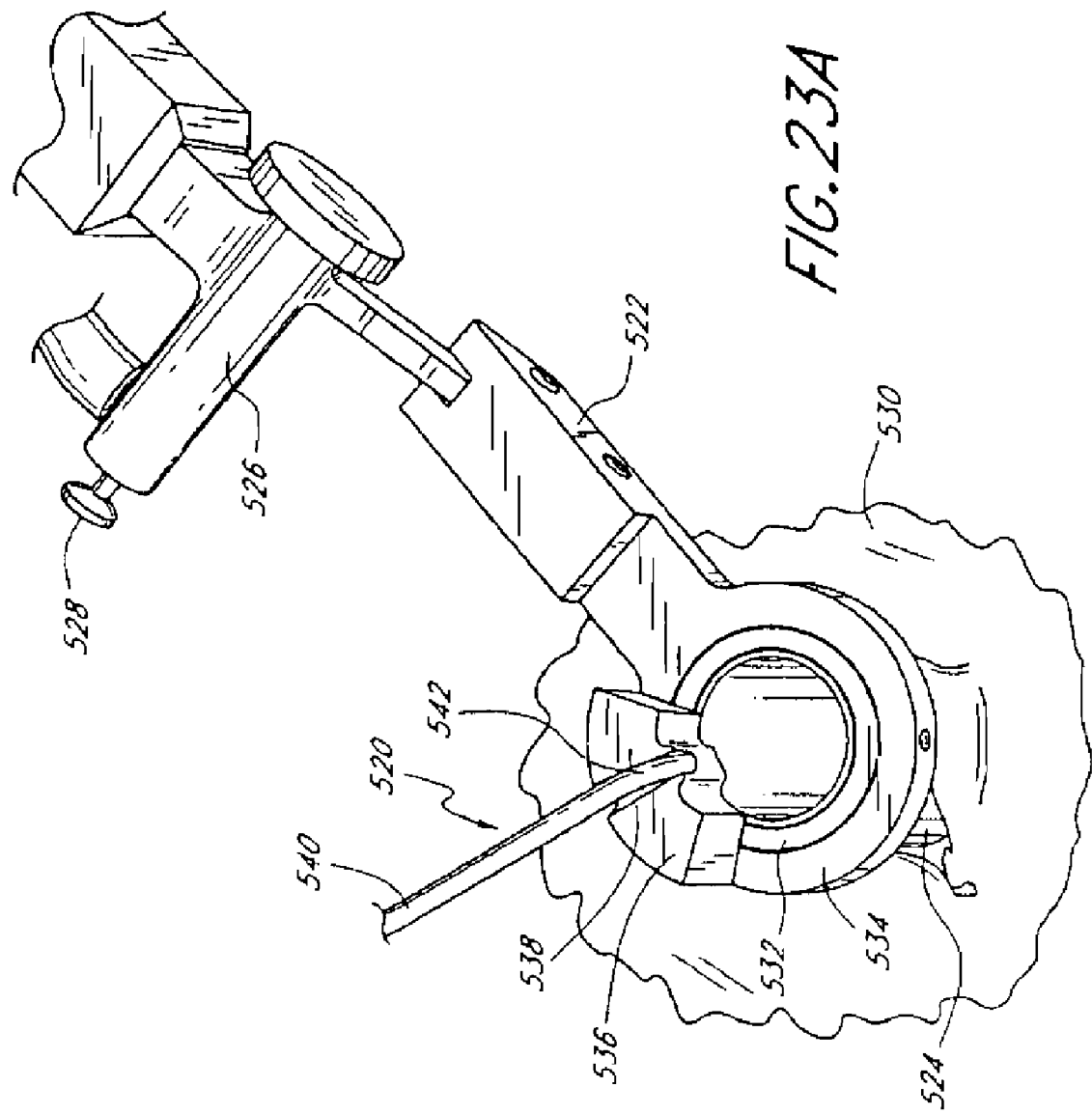

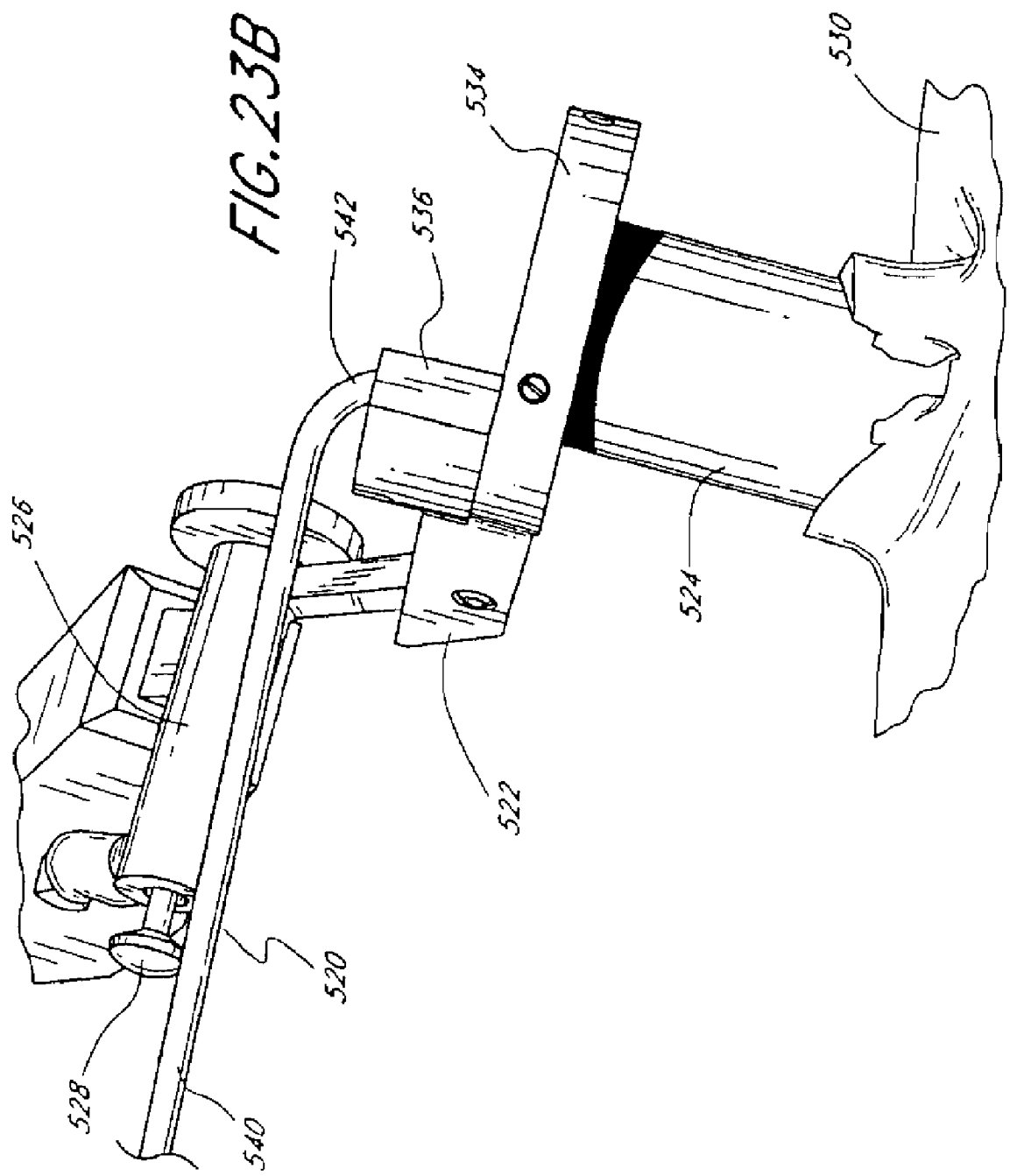

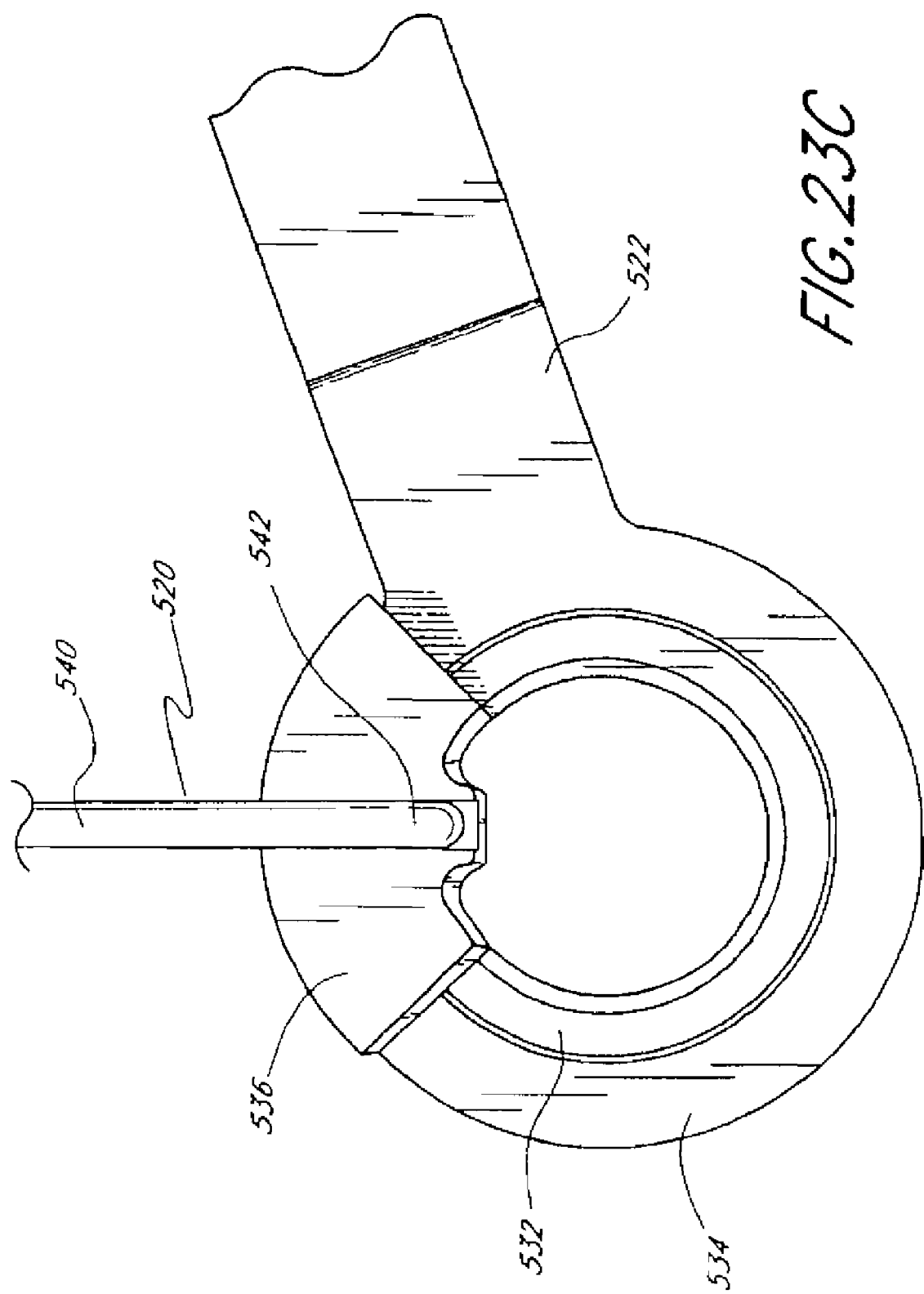

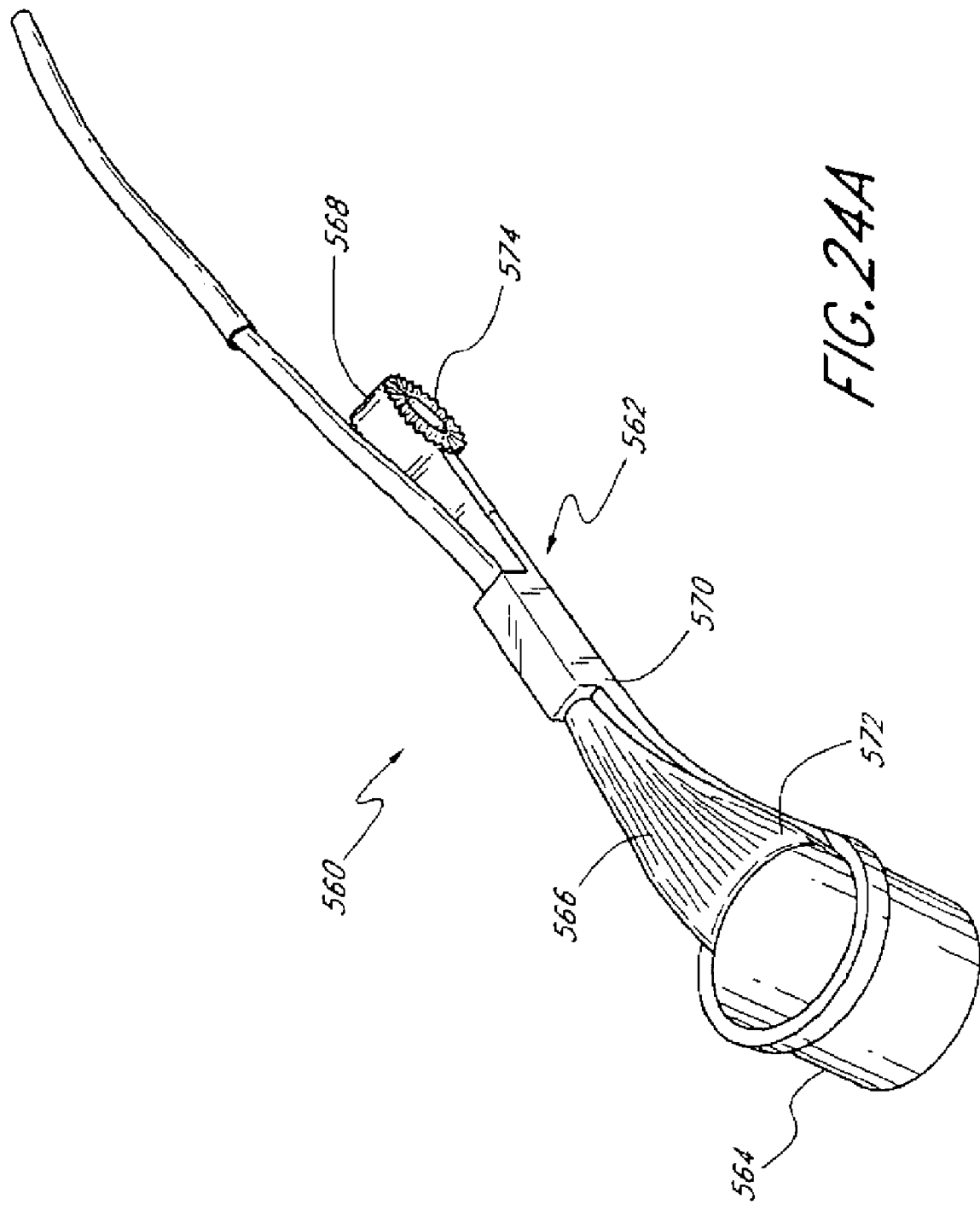

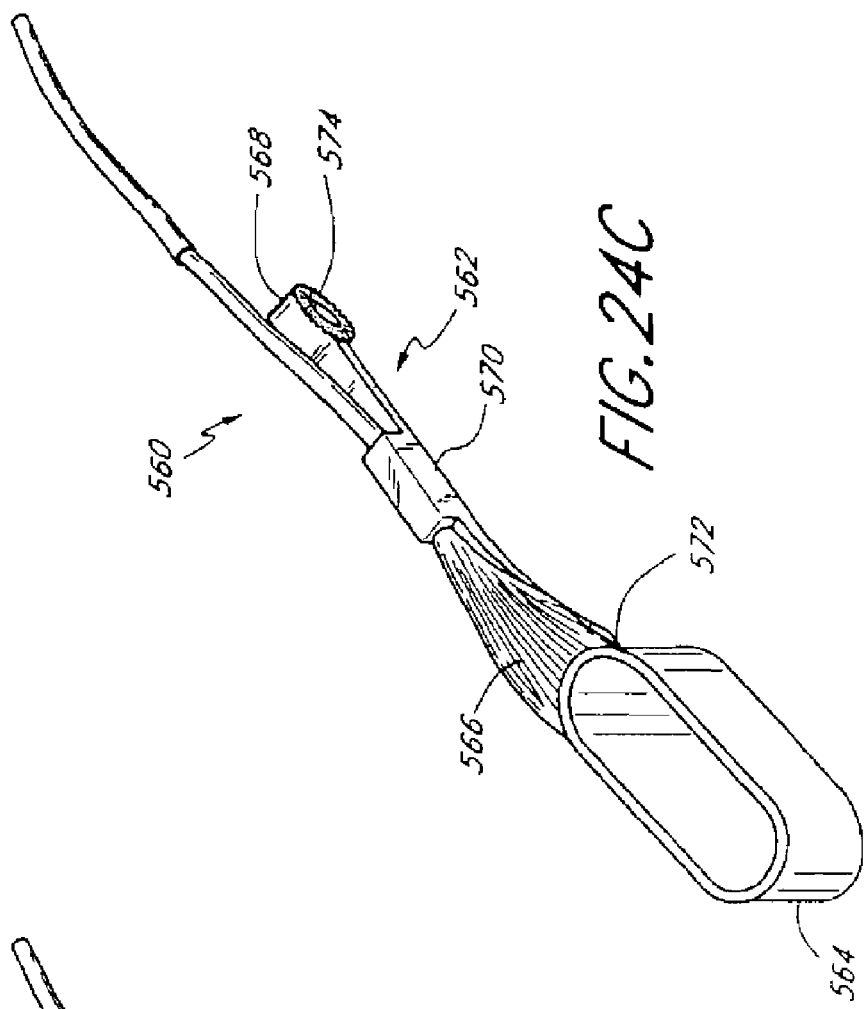
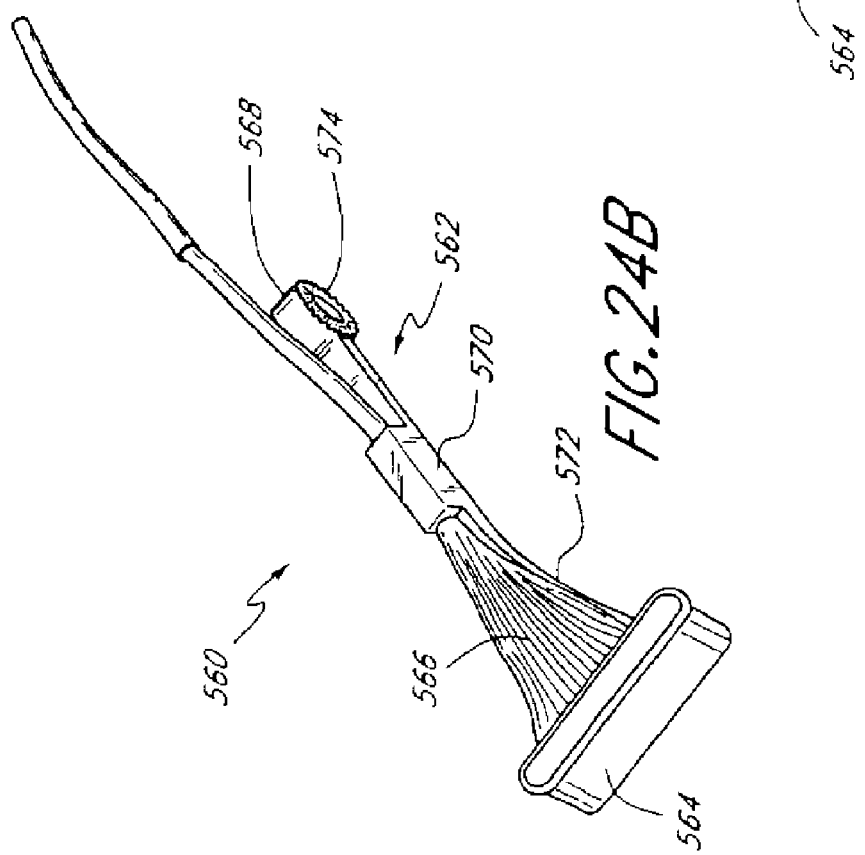

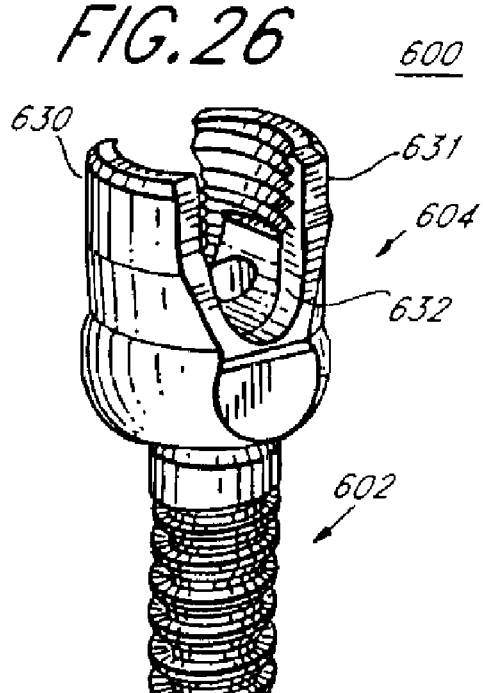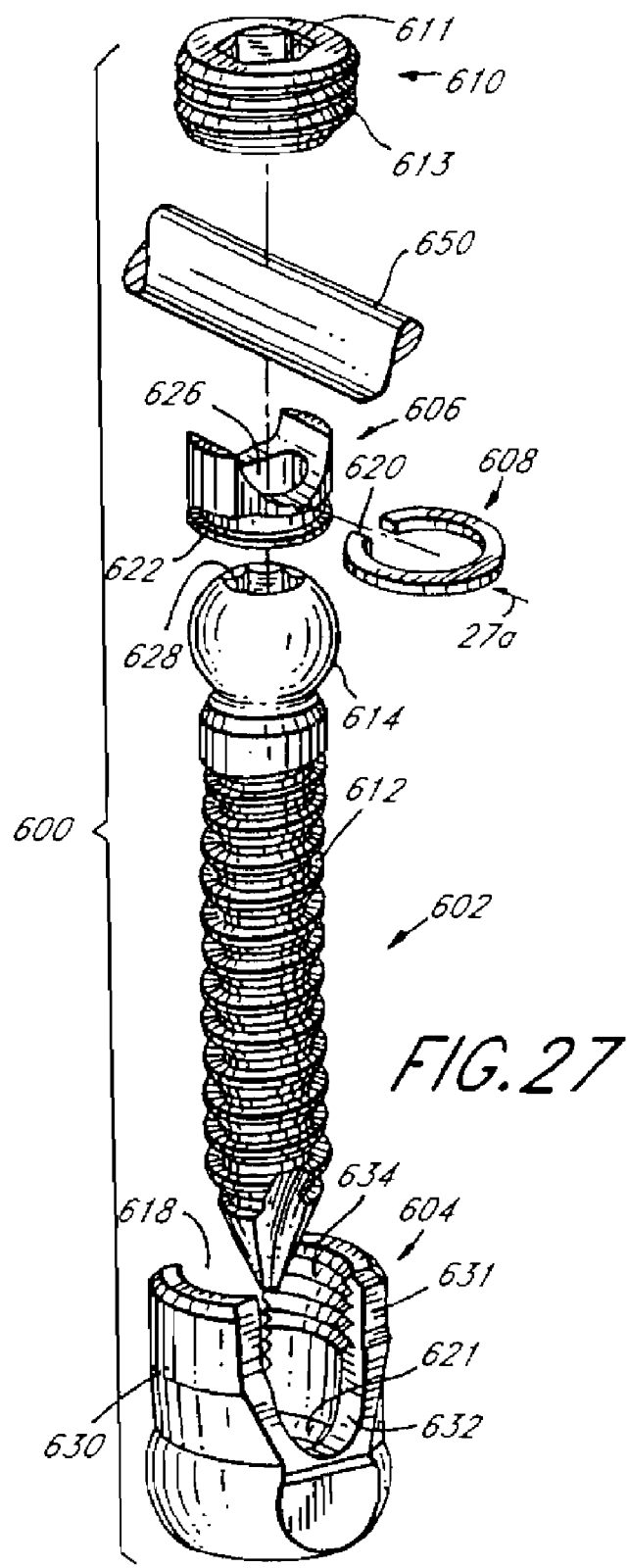

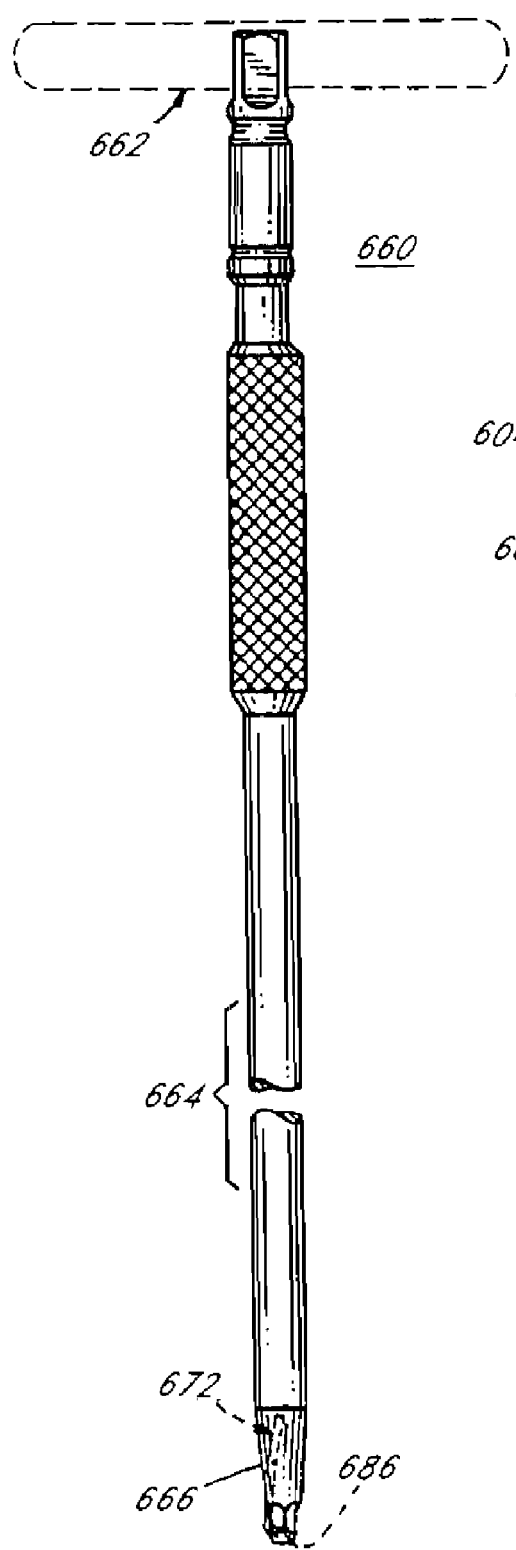
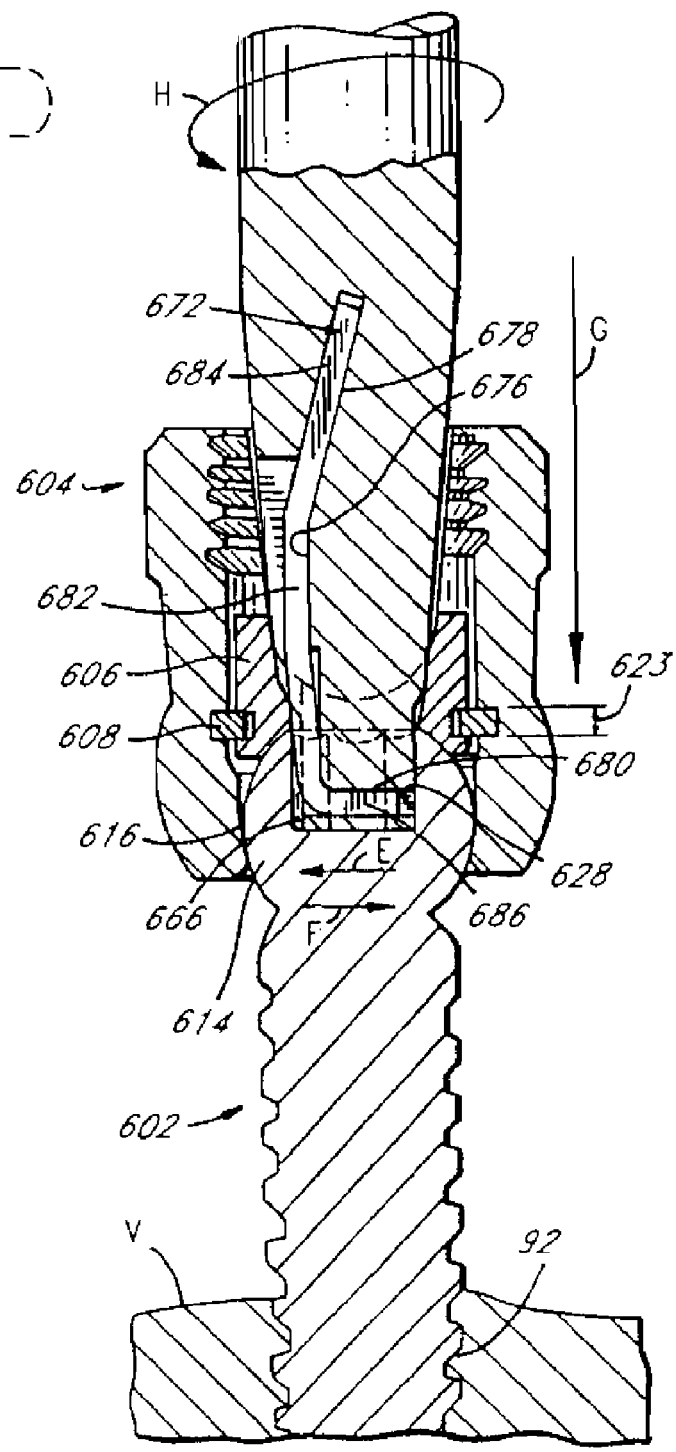
FIG.28
FIG.29

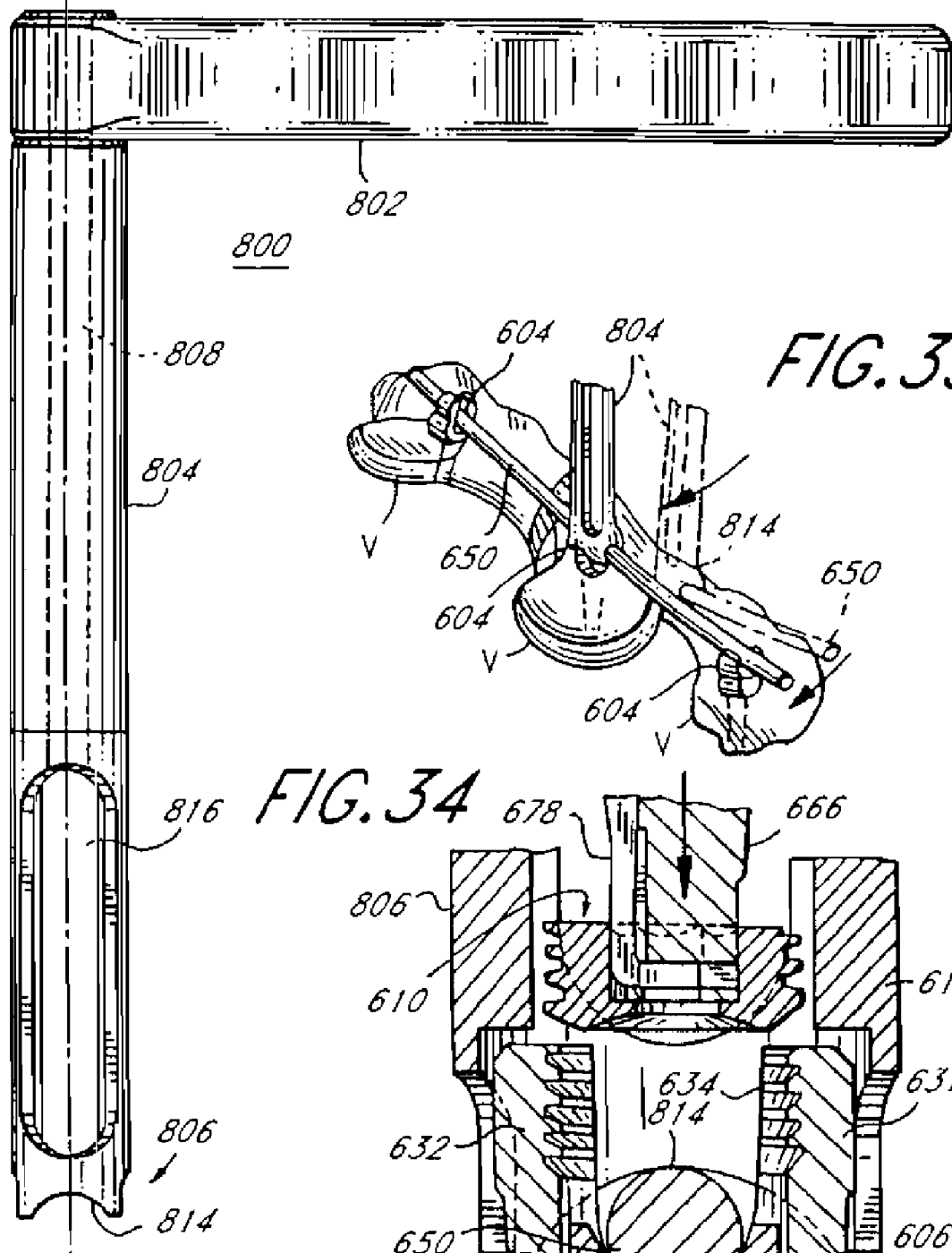
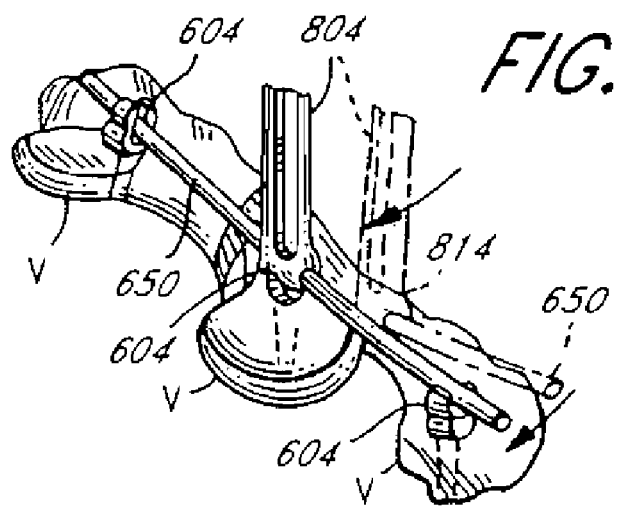
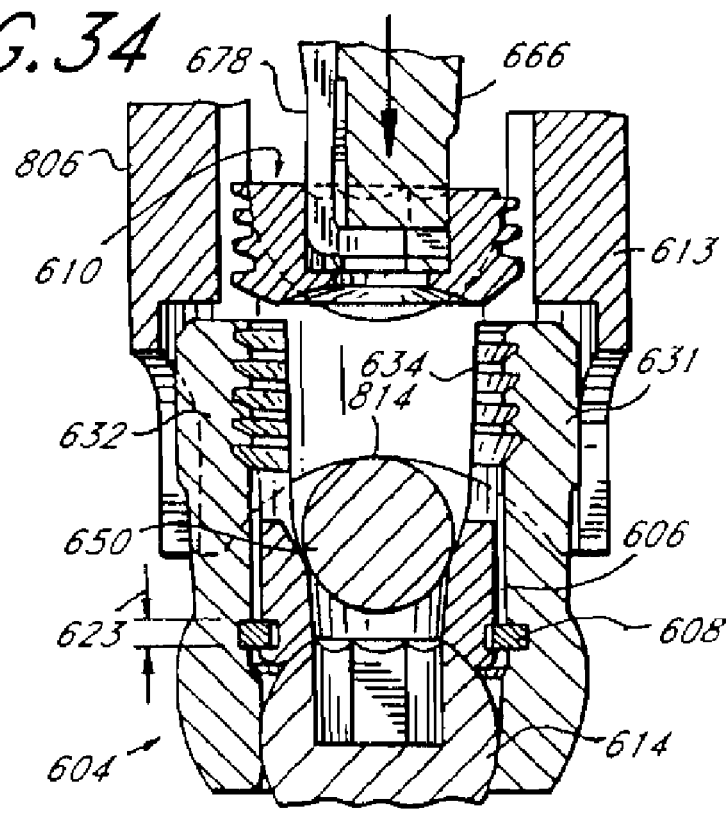

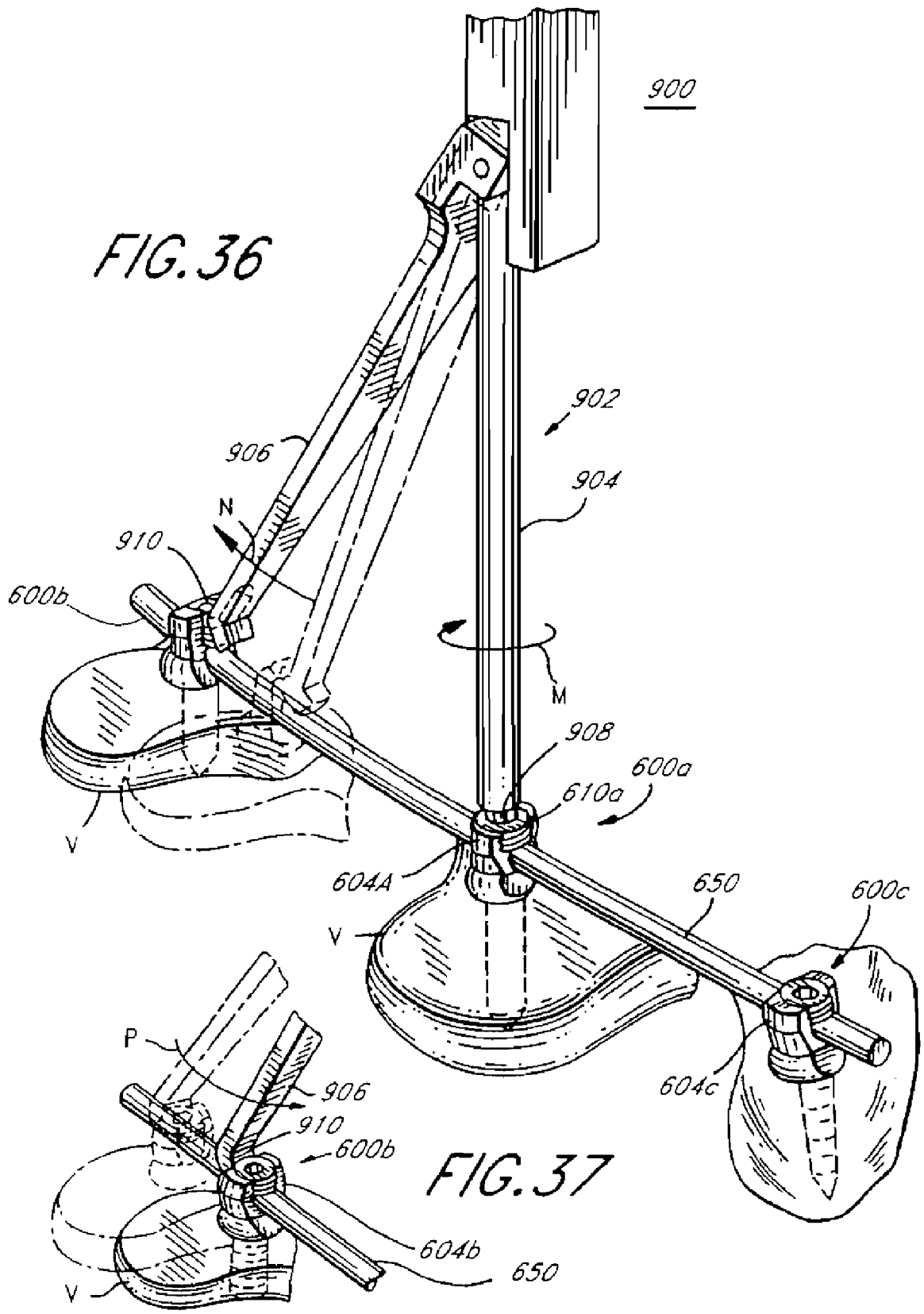

METHODS AND APPARATUSES FOR PERCUTANEOUS IMPLANT DELIVERY

CROSS REFERENCE TO RELATED APPLICATIONS

This application claims the benefit of U.S. Provisional Application No. 60/590,986, filed Jul. 23, 2004, the entire disclosure of which is hereby expressly incorporated by reference herein.

BACKGROUND OF THE INVENTION

1. Field of the Invention

This application relates to surgical methods and apparatuses, and in particular to methods and apparatuses that employ percutaneous and minimally invasive access to treat a patient's spine.

2. Description of the Related Art

Spine surgery presents significant difficulties to the physician attempting to reduce chronic back pain or correct spinal deformities without introducing additional trauma due to the spine surgery itself. In order to access the vertebrae to perform spinal procedures, the physician typically makes large incisions and cuts or strips muscle tissue surrounding the spine. In addition, care must be taken not to injure nerve tissue in the area. Consequently, traditional spine surgery carries high risks of scarring, pain, significant blood loss, and extended recovery times.

Apparatuses for performing minimally invasive techniques have been proposed to reduce the trauma of spine surgery by reducing the size of the incision and the degree of muscle stripping in order to access the vertebrae. One such apparatus provides a constant diameter cannula that is made narrow in order to provide a small entry profile. As a result of the small diameter, the cannula provides minimal space for the physician to observe the anatomy and manipulate surgical instruments in order to perform the required procedures. For example, a narrow cannula is typically insufficient to perform one level spinal fixation procedures, which sometimes involve visualization of two vertebrae and introduction of screws, rods, and other large spinal fixation devices.

SUMMARY OF THE INVENTION

Accordingly, there is a need in the art for systems and methods for treating the spine that combine techniques performed percutaneously and techniques performed through an access device.

In one method, the spine of a patient is treated. A guidewire is advanced through an incision in the skin of the patient to a target location of a vertebra. An implant is advanced over the guidewire to the target location of the vertebra. The implant is coupled with the vertebra at the target location. An elongate body that has a proximal end and a distal end is advanced until the distal end is adjacent the target location. The elongate body has an inner surface that defines a passage that extends therethrough. A procedure is performed at the target location.

In one application, percutaneous access is provided to a vertebral target site. A guidewire is advance to the target site. Instruments are used to deliver a cannulated marker to a pedicle within a patient. Additional cannulated markers are placed in adjacent pedicles. Thereafter, an access device is inserted into the patient to provide access to the cannulated markers. The access device is inserted into the patient in a first configuration having a first cross-sectional area at a distal portion thereof. The access device is actuated to a second configuration having an enlarged cross-sectional area at the distal portion thereof, such that the distal portion extends across at least one marker. The markers are then removed and replaced with fasteners. A spanning member, such as a fixation element or a flexible member, is then secured to the fasteners.

In another embodiment, percutaneous instruments are used to deliver a cannulated screw portion of a fastener to a pedicle within a patient. The fastener comprises an elongate engagement portion and a housing portion. Additional elongate engagement portions are placed in adjacent pedicles. Thereafter, an access device is inserted into the patient and actuated such that the distal portion of the access device extends across at least one elongate engagement portion. Housing portions are inserted through the access device and coupled with corresponding elongate engagement portions. A spanning member, such as fixation element or a flexible member, is then secured to the fasteners.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 2 is a perspective view of one embodiment of an access device in a reduced profile configuration.

FIG. 3 is a perspective view of the access device of FIG. 2 in a first enlarged configuration.

FIG. 4 is a perspective view of the access device of FIG. 2 in a second enlarged configuration.

FIG. 20 is a side view of the endoscope mount platform of FIG. 18 illustrated with one embodiment of an indexing arm and one embodiment of an endoscope.

FIG. 21 is a perspective view of one embodiment of an indexing collar of the endoscope mount platform FIG. 18.

FIG. 22 is a perspective view of one embodiment of an endoscope.

FIG. 23A is a top perspective view of one embodiment of an access system.

FIG. 23B is a side perspective view of the access system of FIG. 23A.

FIG. 23C is a top view of the access system of FIG. 23A.

FIG. 24A is a perspective view of one embodiment of a lighting element.

FIG. 24B is a perspective view of another embodiment of a lighting element.

FIG. 24C is a perspective view of another embodiment of a lighting element.

FIG. 26 is a perspective view of one embodiment of a fastener.

FIG. 27 is an exploded perspective view of the fastener of FIG. 26.

FIG. 27A is an enlarged side view of one embodiment of a biasing member illustrated in FIG. 27 taken from the perspective of the arrow 27A.

FIG. 28 is a perspective view of one embodiment of a surgical instrument.

FIG. 29 is an enlarged sectional view of the fastener of FIGS. 26-27 coupled with the surgical instrument of FIG. 28, illustrating one stage of one application for treating the spine of a patient.

FIG. 32 is a side view of one embodiment of another surgical instrument.

FIG. 33 is a perspective view similar to FIG. 31 illustrating the apparatuses of FIGS. 26 and 32, in one stage of one application for treating the spine of a patient.

FIG. 34 is an enlarged sectional view of the apparatus of FIGS. 26 and 32, illustrating one stage of one application for treating the spine of a patient.

FIG. 36 is an enlarged view in partial section illustrating one stage of one application for treating the spine of a patient.

FIG. 37 is a partial view of illustrating one stage of one application for treating the spine of a patient.

FIG. 71 also illustrates a housing configured to be coupled with the fastener during a procedure.

Figure 1:
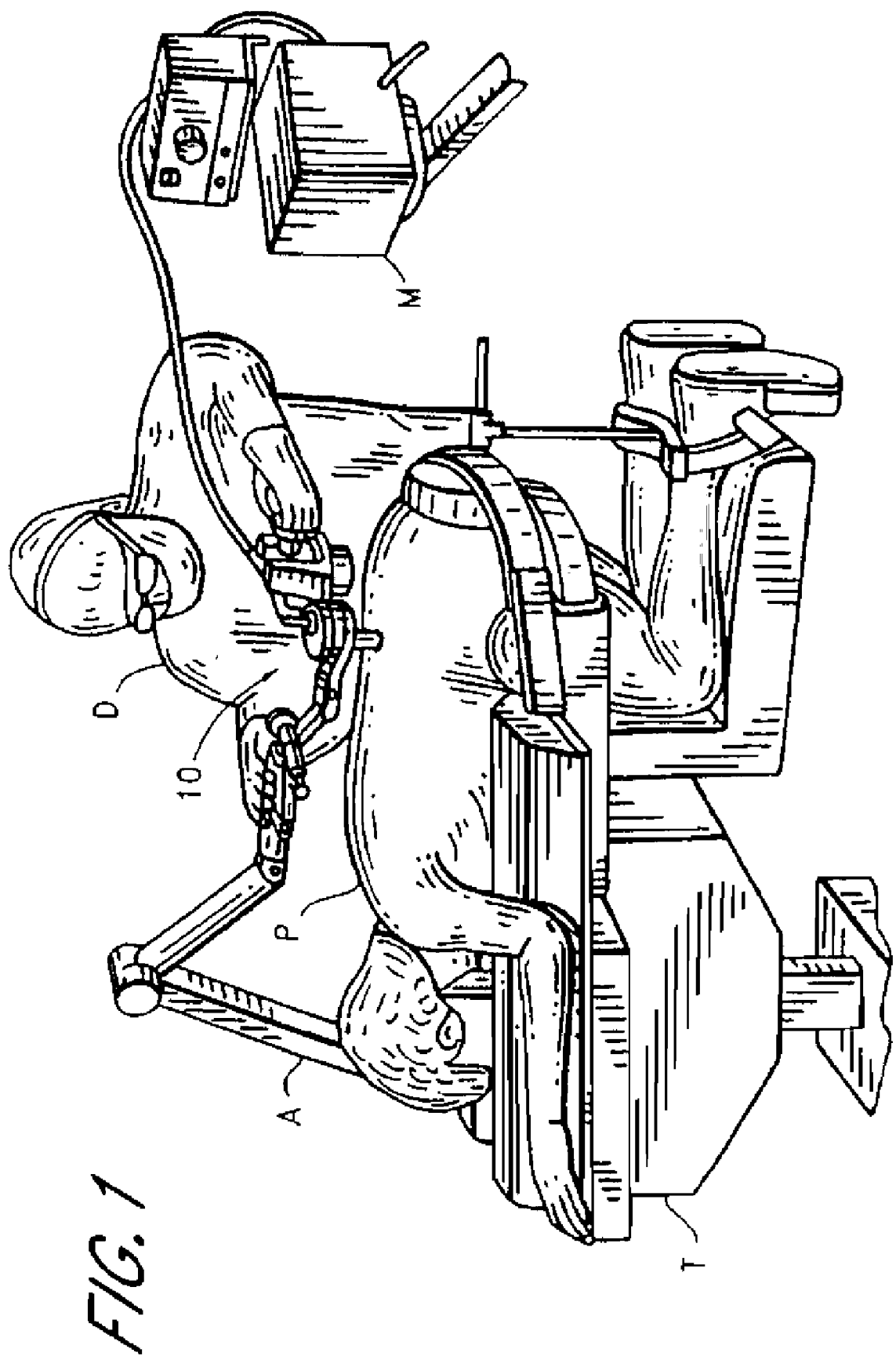
FIG. 1 is a perspective view of one embodiment of a surgical system and one application for treating the spine of a patient.
Figure 6:
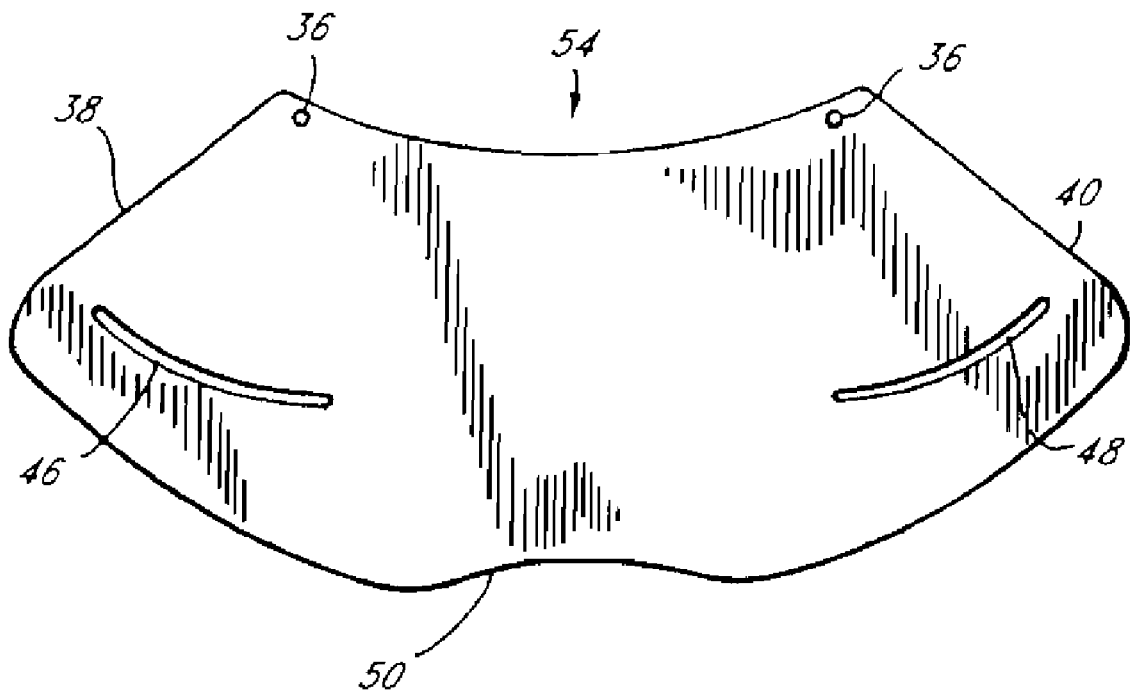
FIG. 6 is a view of another embodiment of a skirt portion of an access device.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention.

DETAILED DESCRIPTION OF THE PREFERRED EMBODIMENT

As should be understood in view of the following detailed description, this application is primarily directed to apparatuses and methods providing access to the spine of a patient and for treating the spine in a minimally invasive manner. As further explained below, minimally invasive procedures lessen trauma (e.g., by reducing incision sizes and reducing the amount of tissue disrupted) than open procedures with similar operative goals. Accordingly, a number of minimally invasive retractors or access devices are discussed herein. In some cases it is beneficial to further reduce trauma to the patient by reducing the amount of time that access devices are deployed within the patient. This may be achieved by performing some of the steps of a spine surgical procedure before or after deployment of a retractor or other similar access device.

I. Systems for Performing Procedures at a Surgical Location

Various embodiments of apparatuses and procedures described herein will be discussed in terms of minimally invasive procedures and apparatuses, e.g., of endoscopic apparatuses and procedures. However, various embodiments may find use in conventional, open, and mini-open procedures. As used herein, the term "proximal," as is traditional, refers to the end portion of an apparatus that is closest to the operator, while the term "distal" refers to the end portion that is farthest from the operator.

FIG. 1 shows one embodiment of a surgical system 10 that can be used to perform a variety of methods or procedures. In one embodiment, as discussed more fully below, the patient P is placed in the prone position on operating table T, taking care that the abdomen is not compressed and physiological lordosis is preserved. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006. The mechanical support arm A is sometimes referred to as a "flex arm." As discussed in greater detail below, the mechanical support arm A is coupled with at least one of an access device and a viewing element.

The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device also can retract tissue to provide greater access to the surgical location. The term "retractor" is used in its ordinary sense to mean a device that can displace tissue and is a broad term and it includes structures having an elongated dimension and defining a passage, e.g., a cannula or a conduit, to retract tissue.

Visualization of the surgical site may be achieved in any suitable manner, e.g., by direct visualization, or by use of a viewing element, such as an endoscope, a camera, loupes, a microscope, or any other suitable viewing element, or a combination of the foregoing. The term "viewing element" is used in its ordinary sense to mean a device useful for viewing and is a broad term and it also includes elements that enhance viewing, such as, for example, a light source or lighting element. In one embodiment, the viewing element provides a video signal representing images, such as images of the surgical site, to a monitor M. The viewing element may be an endoscope and camera that captures images to be displayed on the monitor M whereby the physician D is able to view the surgical site as the procedure is being performed. The endoscope and camera will be described in greater detail herein.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra (e) within the cervical, thoracic, and lumbar regions of the spine. The procedures may be directed toward surgery involving one or more vertebral levels. Some embodiments are useful for anterior and/or lateral procedures. A retroperitoneal approach can also be used with some embodiments. In one retroperitoneal approach, an initial transverse incision is made just left of the midline, just above the pubis, about 3 centimeters in length. The incision can be carried down through the subcutaneous tissues to the anterior rectus sheath, which is incised transversely and the rectus is retracted medially. At this level, the posterior sheath, where present, can be incised. With blunt finger dissection, the retroperitoneal space can be entered. The space can be enlarged with blunt dissection or with a retroperitoneal balloon dissector. The peritoneal sack can be retracted, e.g., by one of the access devices described herein.

It is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly useful for minimally invasive procedures, e.g., arthroscopic procedures. As discussed more fully below, one embodiment of an apparatus described herein provides an access device that is expandable, e.g., including an expandable distal portion. In addition to providing greater access to a surgical site than would be provided with a device having a constant cross-section from proximal to distal, the expandable distal portion prevents or substantially prevents the access device, or instruments extended therethrough to the surgical site, from dislodging or popping out of the operative site.

A. Systems and Devices for Establishing Access

In one embodiment, the system 10 includes an access device that provides an internal passage for surgical instruments to be inserted through the skin and muscle tissue of the patient P to the surgical site. The access device preferably has a wall portion defining a reduced profile, or low-profile, configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the access device therein.

The wall portion of the access device preferably can be subsequently expanded to an enlarged configuration, by moving against the surrounding muscle tissue to at least partially define an enlarged surgical space in which the surgical procedures will be performed. In a sense, it acts as its own dilator. The access device may also be thought of as a retractor, and may be referred to herein as such. Both the distal and proximal portion may be expanded, as discussed further below. However, the distal portion preferably expands to a greater extent than the proximal portion, because the surgical procedures are to be performed at the surgical site, which is adjacent the distal portion when the access device is inserted into the patient.

While in the reduced profile configuration, the access device preferably defines a first unexpanded configuration. Thereafter, the access device can enlarge the surgical space defined thereby by engaging the tissue surrounding the access device and displacing the tissue outwardly as the access device expands. The access device preferably is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein, as will be described below. The surgical site preferably is at least partially defined by the expanded access device itself. During expansion, the access device can move from a first overlapping configuration to a second overlapping configuration in some embodiments.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician D may remain substantially stable during such distal movement. In one embodiment, the distal portion is a separate component that is pivotally or movably coupled to the proximal portion. In another embodiment, the distal portion is flexible or resilient in order to permit such relative movement.

1. Access Devices

One embodiment of an access device is illustrated in FIGS. 2-6 and designated by reference number 20. In one embodiment, the access device 20 includes a proximal wall portion 22 that has a tubular configuration, and a distal wall portion that has an expandable skirt portion 24. The skirt portion 24 preferably is enlargeable from a reduced profile configuration having an initial dimension 26 (illustrated in FIG. 2) and corresponding cross-sectional area, to an enlarged configuration having a second dimension 28 (illustrated in FIG. 4) and corresponding cross-sectional area. In one embodiment, the skirt portion 24 is coupled to the proximal wall portion 22 with a rivet 30, pin, or similar connecting device to permit movement of the skirt portion 24 relative to the proximal wall portion 22.

In the illustrated embodiment, the skirt portion 24 is manufactured from a resilient material, such as stainless steel. The skirt portion 24 preferably is manufactured so that it normally assumes an expanded configuration as illustrated in FIG. 4. With reference to FIG. 3, the skirt portion 24 may assume an intermediate dimension 34 and corresponding cross-sectional area, which is greater than the initial dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 can depend upon several factors, such as the rigidity of the skirt portion 24, the surrounding tissue, and whether such surrounding tissue has relaxed or tightened during the course of the procedure. An outer sleeve 32 (illustrated in dashed line in FIG. 2) may be provided. Preferably, the outer sleeve surrounds the access device 20 and maintains the skirt portion 24 in the reduced profile configuration prior to insertion into the patient. The outer sleeve 32 may be made of plastic. Where provided, the outer sleeve 32 preferably is configured to be easily deployed. For example, a release device may be provided that releases or removes the outer sleeve 32 upon being operated by the user. In one embodiment, a braided polyester suture is embedded within the sleeve 32, aligned substantially along the longitudinal axis thereof. In use, when the suture is withdrawn, the outer sleeve 32 is torn, allowing the access device 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 preferably is sufficiently rigid that it is capable of displacing the tissue surrounding the skirt portion 24 as it expands. Depending upon the resistance exerted by surrounding tissue, the skirt portion 24 preferably is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion preferably creates a stable configuration that is at least temporarily stationary in the patient. This arrangement preferably frees the physician from the need to actively support the access device 20, e.g., prior to adding an endoscope mount platform 300 and a support arm 400 (see FIGS. 21-22).

Figure 5:
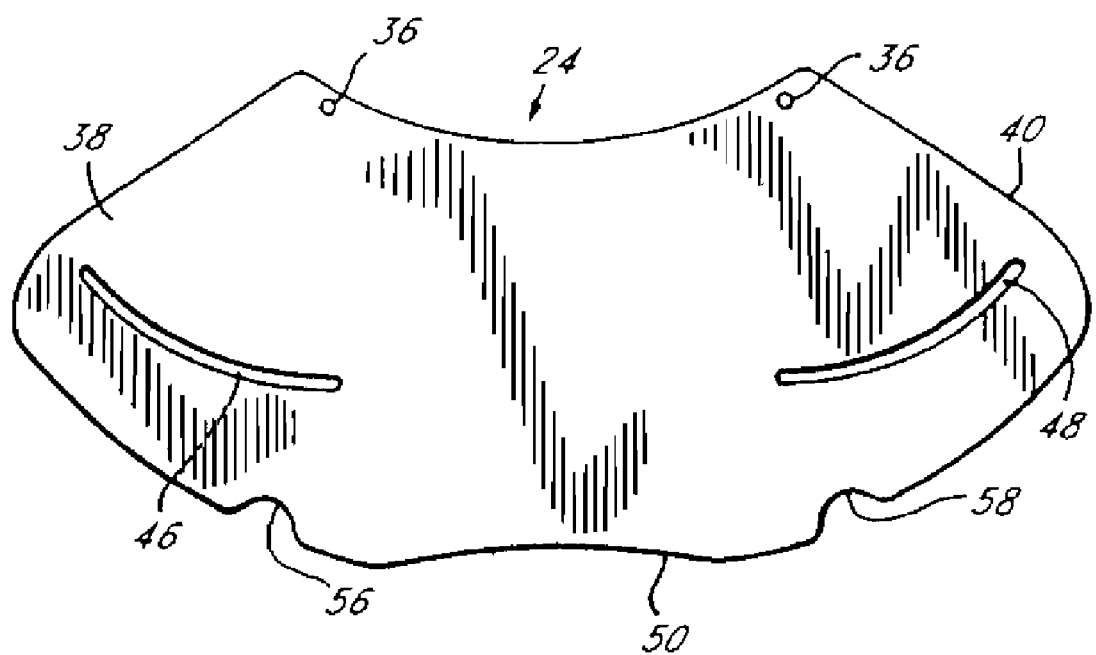
FIG. 5 is a view of one embodiment of a skirt portion of an access device.
Figure 7:
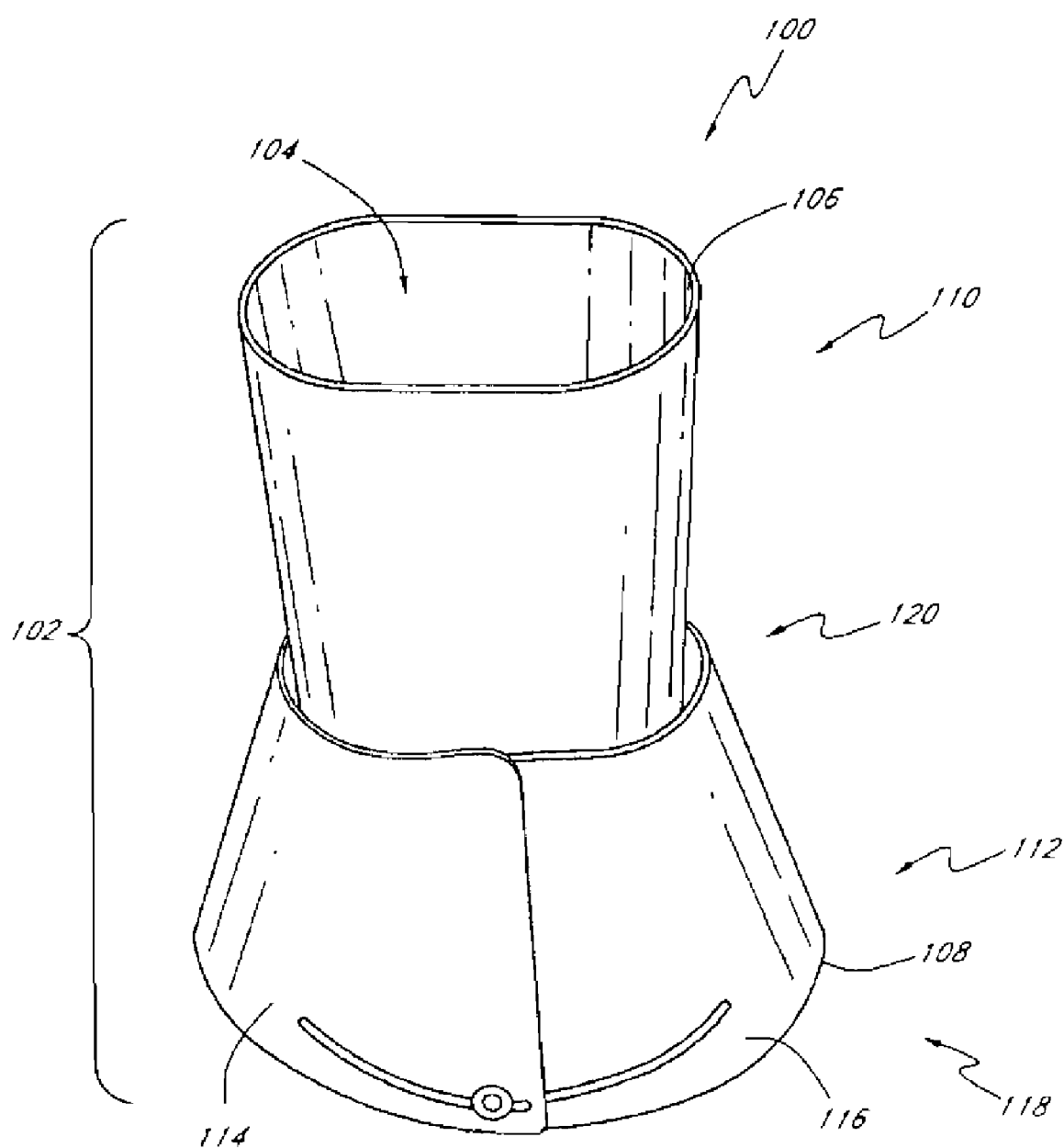
FIG. 7 is a perspective view of another embodiment of an access device.
Figure 8:
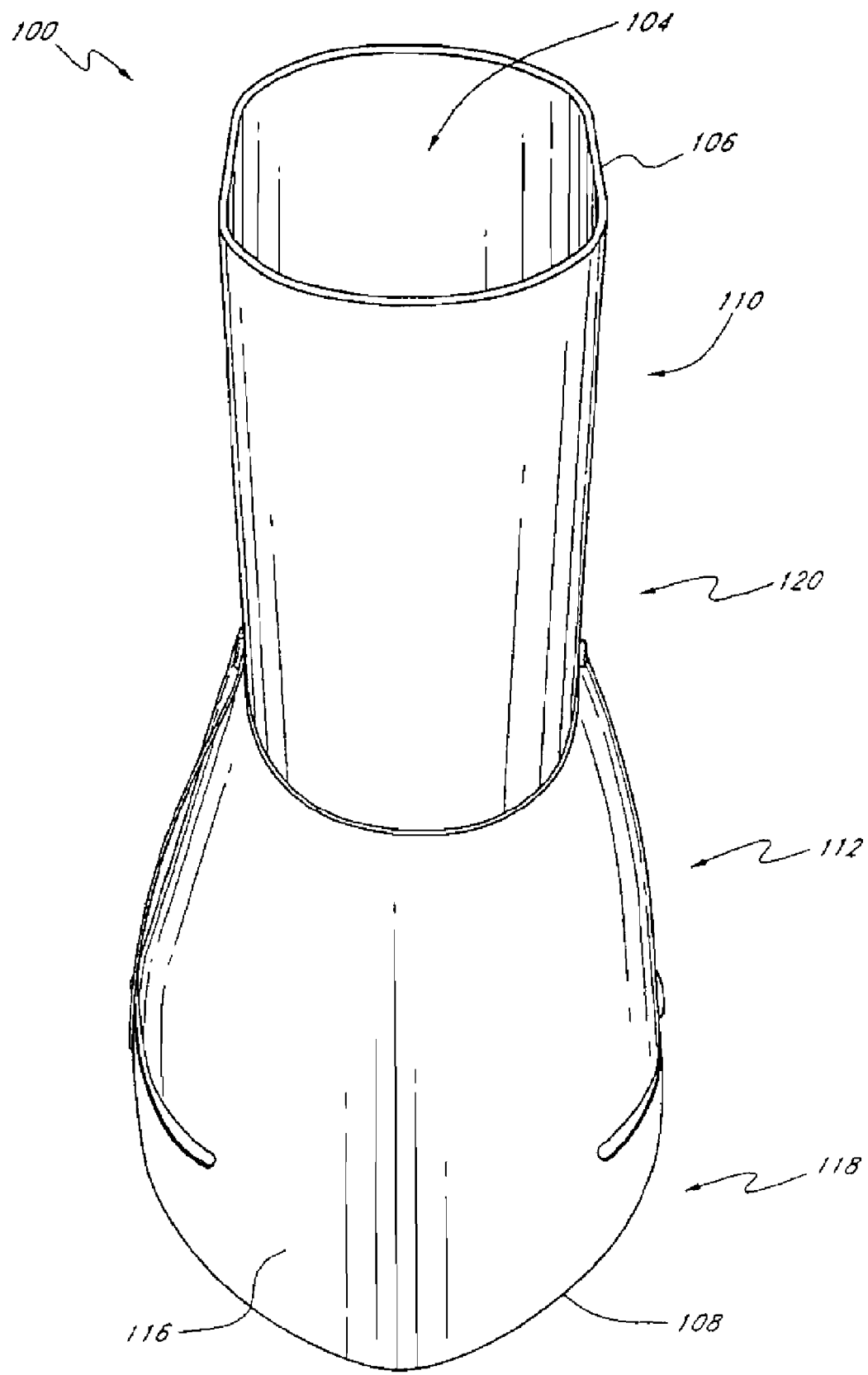
FIG. 8 is a side view of the access device of FIG. 7.
Figure 9:
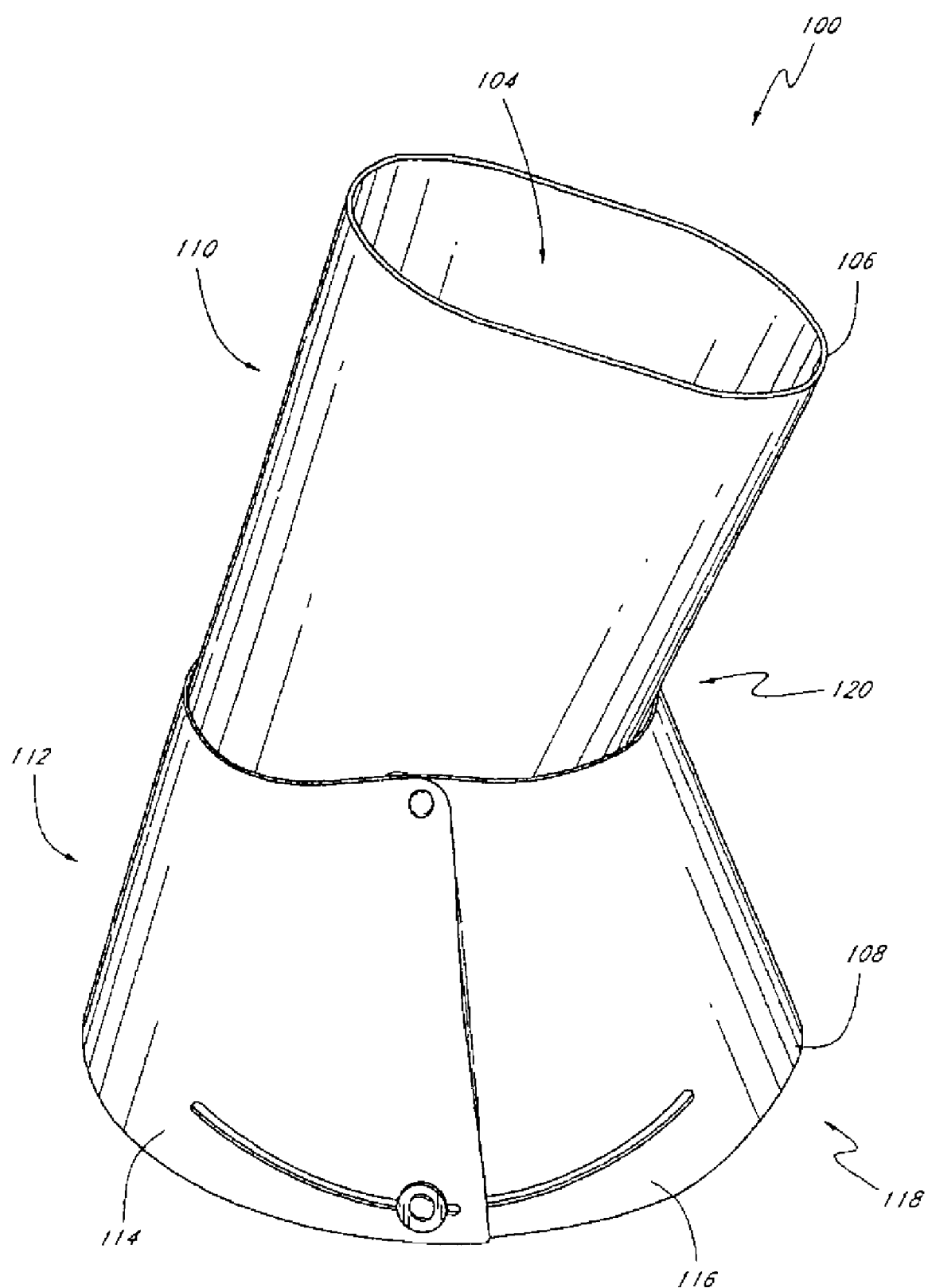
FIG. 9 is a front view of the access device of FIG. 7.
Figure 10:
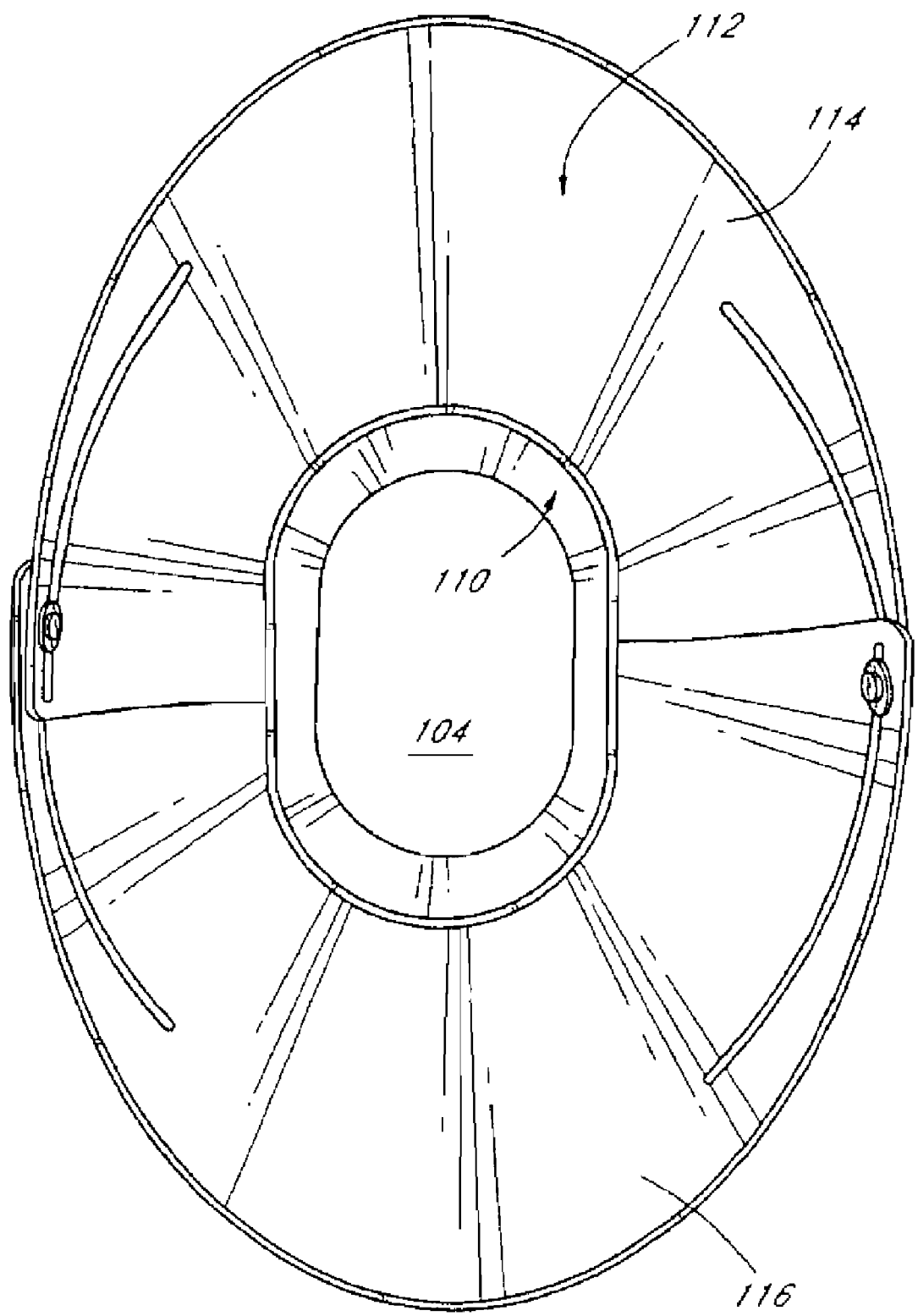
FIG. 10 is a bottom view of the access device of FIG. 7.
Figure 11:
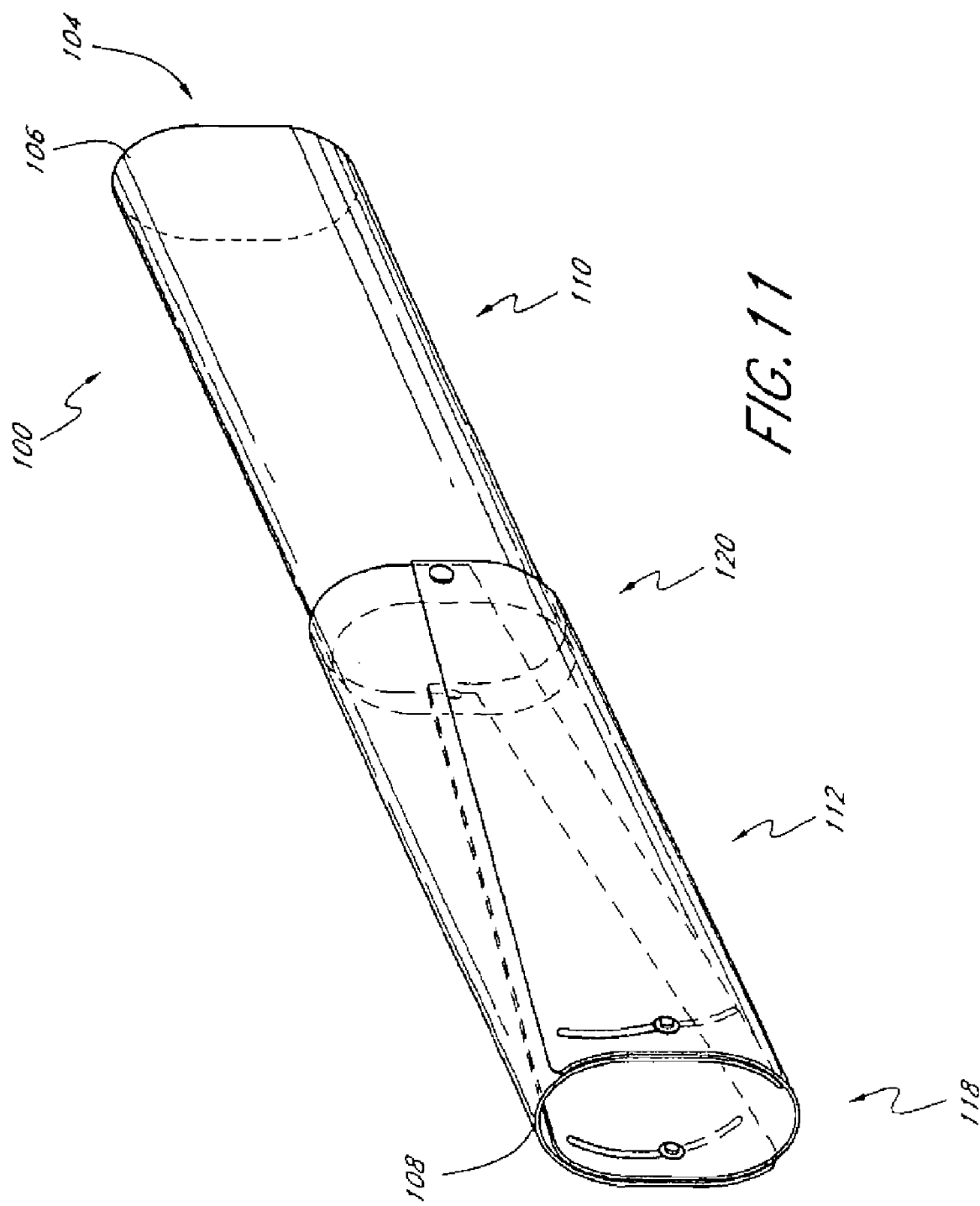
FIG. 11 is a perspective view of the access device of FIG. 7 in a first configuration.
Figure 12:
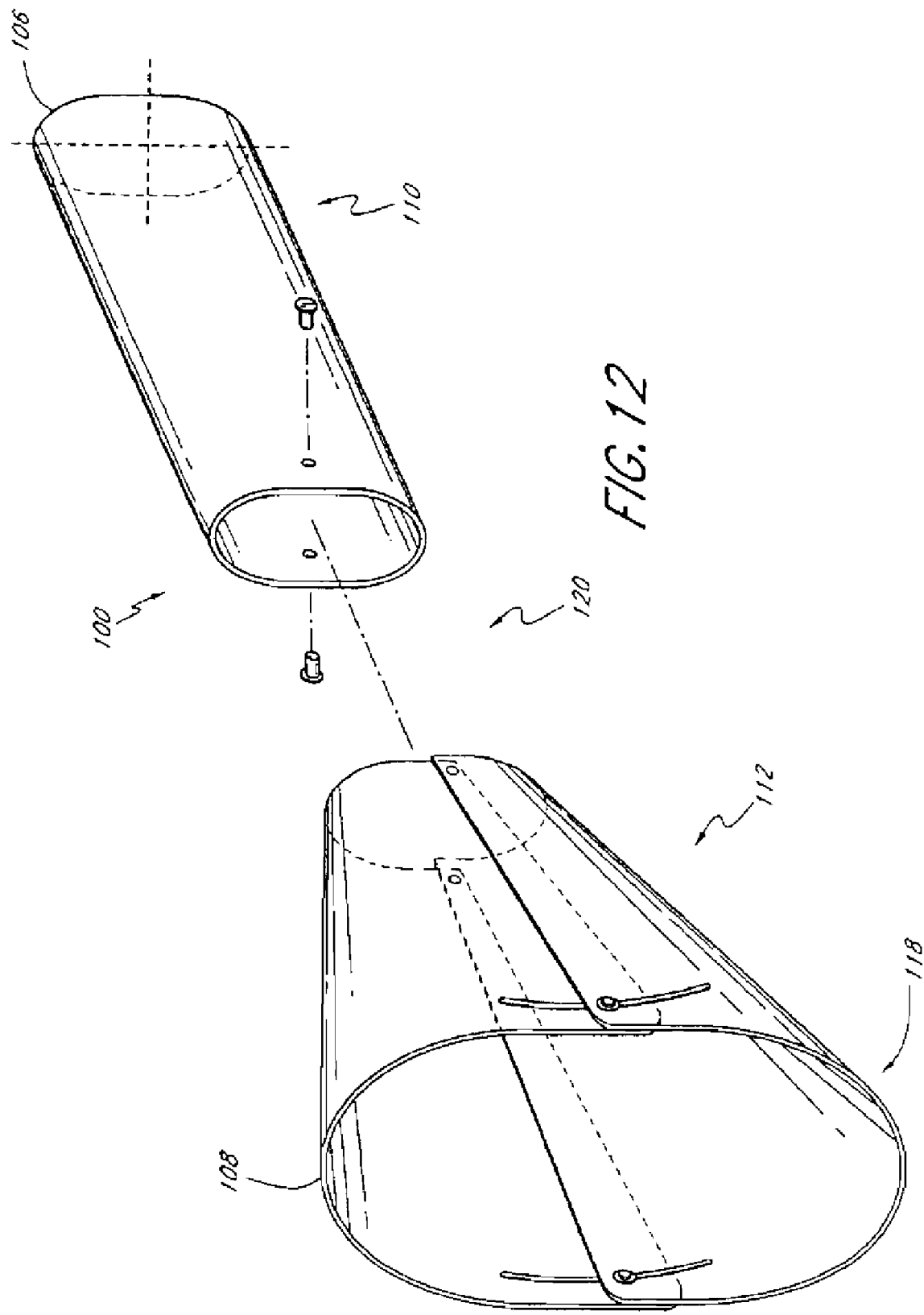
FIG. 12 is an exploded perspective view of the access device of FIG. 7 in a second configuration.

One embodiment of the skirt portion 24 of the access device 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. The unrestricted shape of the skirt portion 24 is a circular shape in one embodiment and is an oblong shape in another embodiment. In another embodiment, the skirt portion 24 has an oval shape, wherein the dimension 28 defines a longer dimension of the skirt portion 24 and would be about 85 mm. In another embodiment, the skirt portion 24 has an oval shape and the dimension 28 defines a longer dimension of the skirt portion 24 of about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 preferably is coupled to the proximal wall portion 22 with a pivotal connection, such as rivet 30. A pair of rivet holes 36 can be provided in the skirt portion 24 to receive the rivet 30. The skirt portion 24 also has two free ends 38 and 40 in one embodiment that are secured by a slidable connection, such as a second rivet 44 (not shown in FIG. 5, illustrated in FIGS. 2-4). A pair of complementary slots 46 and 48 preferably are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. The likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span three or more vertebrae, e.g., L4, L5, and S1. This arrangement enables multi-level procedures, such as multilevel fixation procedures alone or in combination with a variety of other procedures, as discussed below. Other embodiments include a single slot rather than the slots 46, 48, or more than two slots.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58, are provided, as illustrated in FIG. 5. When the skirt portion 24 is assembled, the notched portions 56 and 58 are generally across from each other. When the skirt portion 24 is applied to a patient, the notched portions 56, 58 are oriented in the cephcaudal direction (indicated by a dashed line 60 in FIG. 4). In this arrangement, instruments and implants, such as an elongated member 650 used in a fixation procedure (described in detail below), may extend beyond the area enclosed by the skirt portion 24 without moving or raising the skirt portion 24, e.g., by allowing the elongated member 650 (or other implant or instrument) to pass under the skirt portion 24. The notched portions 56, 58 also enable the elongated member 650 (or other implant or instrument) to extend beyond the portion of the surgical space defined within the outline of the distal end of the skirt portion 24. The notched portions 56, 58 are optional, as illustrated in connection with another embodiment of an access device 54, illustrated in FIG. 6, and may be eliminated if, for example, the physician deems the notches to be unnecessary for the procedures to be performed. For example, in some fixation procedures such extended access is not needed, as discussed more fully below. As illustrated in FIG. 4, the skirt portion 24 may be expanded to a substantially conical configuration having a substantially circular or elliptical profile.

Furthermore, it is contemplated that the skirt portion 24 of the access device 20 can include a stop that retains the skirt portion in an expanded configuration, as shown in U.S. patent application Ser. No. 10/361,887, filed Feb. 10, 2003, now U.S. Application Patent Publication No. U.S. 2003/153927 A1, which is hereby incorporated by reference in its entirety herein.

With reference to FIGS. 7-12, another embodiment of an access device 100 comprises an elongate body 102 defining a passage 104 and having a proximal end 106 and a distal end 108. The elongate body 102 has a proximal portion 110 and a distal portion 112. The proximal portion 110 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The proximal portion 110 comprises an oblong, generally oval shaped cross section over the elongated portion. It will be apparent to those of skill in the art that the cross section can be of any suitable oblong shape. The proximal portion 110 can be any desired size. The proximal portion 110 can have a cross-sectional area that varies from one end of the proximal portion to another end. For example, the cross-sectional area of the proximal portion can increase or decrease along the length of the proximal portion 110. Preferably, the proximal portion 110 is sized to provide sufficient space for inserting multiple surgical instruments through the elongate body 102 to the surgical location. The distal portion 112 preferably is expandable and comprises first and second overlapping skirt members 114, 116. The degree of expansion of the distal portion 112 is determined by an amount of overlap between the first skirt member 114 and the second skirt member 116 in one embodiment.

The elongate body 102 of the access device 100 has a first location 118 distal of a second location 120. The elongate body 102 preferably is capable of having a configuration when inserted within the patient wherein the cross-sectional area of the passage 104 at the first location 118 is greater than the cross-sectional area of the passage 104 at the second location 120. The passage 104 preferably is capable of having an oblong shaped cross section between the second location 120 and the proximal end 106. In some embodiments the passage 104 preferably is capable of having a generally elliptical cross section between the second location 120 and the proximal end 106. Additionally, the passage 104 preferably is capable of having a non-circular cross section between the second location 120 and the proximal end 106. Additionally, in some embodiments, the cross section of the passage 104 can be symmetrical about a first axis and a second axis, the first axis being generally normal to the second axis. Other embodiments that can have an oblong cross-section are discussed below in connection with FIGS. 67-95.

In another embodiment, an access device comprises an elongate body defining a passage and having a proximal end and a distal end. The elongate body can be a unitary structure and can have a generally uniform cross section from the proximal end to the distal end. In one embodiment, the elongate body preferably has an oblong or generally oval shaped cross section along the entire length of the elongate body. The passage can have a generally elliptical cross section between the proximal end and the distal end. The elongate body preferably has a relatively fixed cross-sectional area along its entire length. In one embodiment, the elongate body is capable of having a configuration when inserted within the patient wherein the cross-sectional area of the passage at a first location is equal to the cross-sectional area of the passage at a second location. The passage preferably is capable of having an oblong shaped cross section between the first and second locations. The cross section of the passage can be of any suitable oblong shape and the elongate body can be any desired size. Preferably, the elongate body is sized to provide sufficient space for inserting multiple surgical instruments sequentially or simultaneously through the elongate body to the surgical location.

In one embodiment, the access device has a uniform, generally oblong shaped cross section and is sized or configured to approach, dock on, or provide access to, anatomical structures. The access device preferably is configured to approach the spine from a posterior position or from a postero-lateral position. A distal portion of the access device can be configured to dock on, or provide access to, posterior portions of the spine for performing spinal procedures, such as, for example, fixation, fusion, or any other procedure described herein. In one embodiment, the distal portion of the access device has a uniform, generally oblong shaped cross section and is configured to dock on, or provide access to, generally posterior spinal structures. Generally posterior spinal structures can include, for example, one or more of the transverse process, the superior articular process, the inferior articular process, and the spinous process. In some embodiments, the access device can have a contoured distal end to facilitate docking on one or more of the posterior spinal structures. Accordingly, in one embodiment, the access device has a uniform, generally oblong shaped cross section with a distal end sized, configured, or contoured to approach, dock on, or provide access to, spinal structures from a posterior or postero-lateral position.

Further details and features pertaining to access devices and systems are described in U.S. patent application Ser. No. 09/772,605, filed Jan. 30, 2001, application Ser. No. 09/906, 463, filed Jul. 16, 2001, application Ser. No. 10/361,887, filed Feb. 10, 2003, application Ser. No. 10/280,489, filed Oct. 25, 2002, and application Ser. No. 10/678,744 filed Oct. 2, 2003, which are incorporated by reference in their entireties herein.

2. Dilators and Expander Devices

According to one application or procedure, an early stage involves determining a point in the skin of the patient at which to insert the access device 20. The access point preferably corresponds to a posterior-lateral aspect of the spine. Manual palpation and Anterior-Posterior (AP) fluoroscopy may be used to determine preferred or optimal locations for forming an incision in the skin of the patient. In one application, the access device 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, preferably minimizing damage to the structure of surrounding tissue and muscles. A first dilator can be placed over the guide wire to expand the opening. The guide wire may then be removed. A second dilator, slightly larger than the first dilator, is placed over the first dilator to expand the opening further. Once the second dilator is in place, the first dilator may be removed. This process of (1) introducing a next-larger-sized dilator coaxially over the previous dilator and (2) optionally removing the previous dilator(s) when the next-larger-sized dilator is in place continues until an opening of the desired size is created in the skin, muscle, and subcutaneous tissue. According to one application, the desired opening size is about 23 mm. (Other dimensions of the opening, e.g., about 20 mm, about 27 mm, about 30 mm, etc., are also useful with this apparatus in connection with spinal surgery, and still other dimensions are contemplated.)

Figure 13:
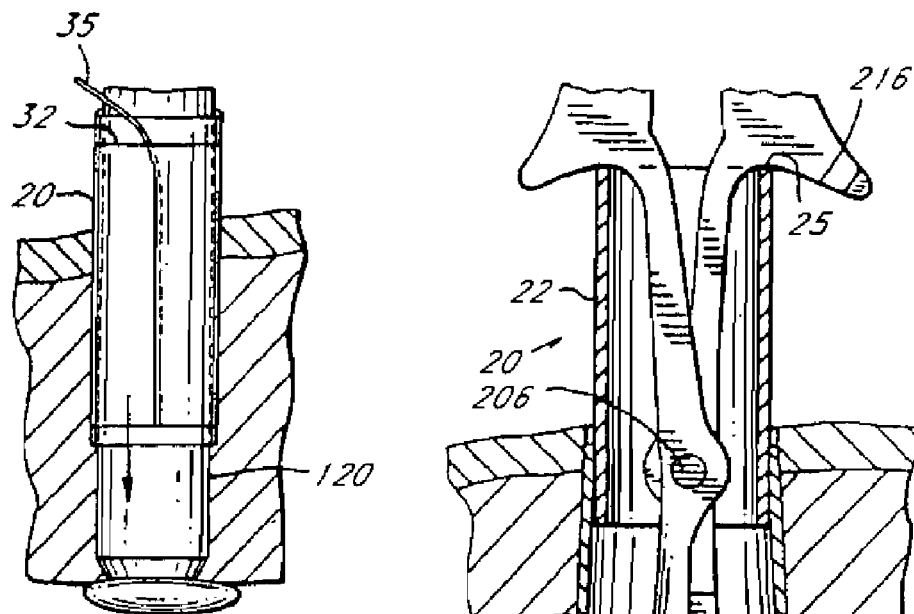
FIG. 13 is a sectional view illustrating one stage of one application for treating the spine of a patient.

FIG. 13 shows that following placement of a dilator 120, which is the largest dilator in the above-described dilation process, the access device 20 is introduced in its reduced profile configuration and positioned over the dilator 120. The dilator 120 is subsequently removed from the patient, and the access device 20 remains in position.

Once positioned in the patient, the access device 20 may be enlarged to provide a passage for the insertion of various surgical instruments and to provide an enlarged space for performing the procedures described herein. As described above, the access device may achieve the enlargement in several ways. In one embodiment, a distal portion of the access device may be enlarged, and a proximal portion may maintain a constant diameter. The relative lengths of the proximal portion 22 and the skirt portion 24 may be adjusted to vary the overall expansion of the access device 20. Alternatively, such expansion may extend along the entire length of the access device 20. In one application, the access device 20 may be expanded by removing a suture 35 and tearing the outer sleeve 32 surrounding the access device 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 preferably allow the access device 20 to resist closing to the reduced profile configuration of FIG. 2 and to at least temporarily resist being expelled from the incision. These characteristics create a stable configuration for the access device 20 to remain in position in the body, supported by the surrounding tissue. It is understood that additional support may be needed, especially if an endoscope is added.

According to one embodiment of a procedure, the access device 20 may be further enlarged at the skirt portion 24 using an expander apparatus to create a surgical access space. An expander apparatus useful for enlarging the access device has a reduced profile configuration and an enlarged configuration. The expander apparatus is inserted into the access device in the reduced profile configuration, and subsequently expanded to the enlarged configuration. The expansion of the expander apparatus also causes the access device to be expanded to the enlarged configuration. In some embodiments, the expander apparatus may increase the diameter of the access device along substantially its entire length in a generally conical configuration. In other embodiments, the expander apparatus expands only a distal portion of the access device, allowing a proximal portion to maintain a relatively constant diameter.

In addition to expanding the access device, in some embodiments the expander apparatus may also be used to position the distal portion of the access device at the desired location for the surgical procedure. The expander can engage an interior wall of the access device to move the access device to the desired location. For embodiments in which the distal portion of the access device is relatively movable with respect to the proximal portion, the expander apparatus is useful to position the distal portion without substantially disturbing the proximal portion.

Figure 15:
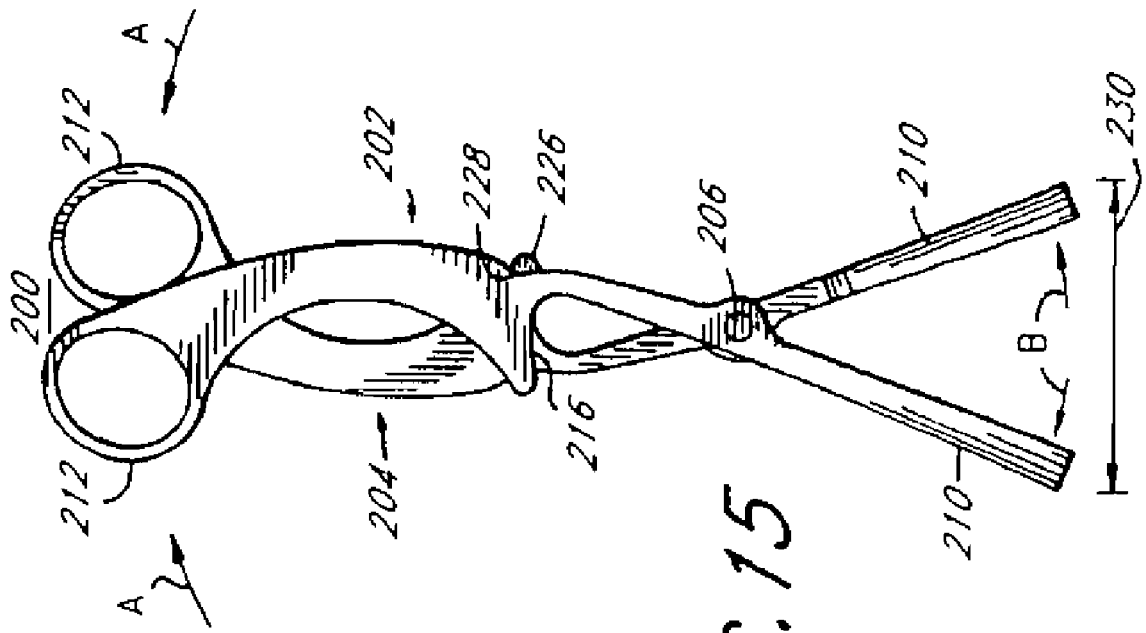
FIG. 15 is a side view of the expander apparatus of FIG. 14 in an expanded configuration.
Figure 14:
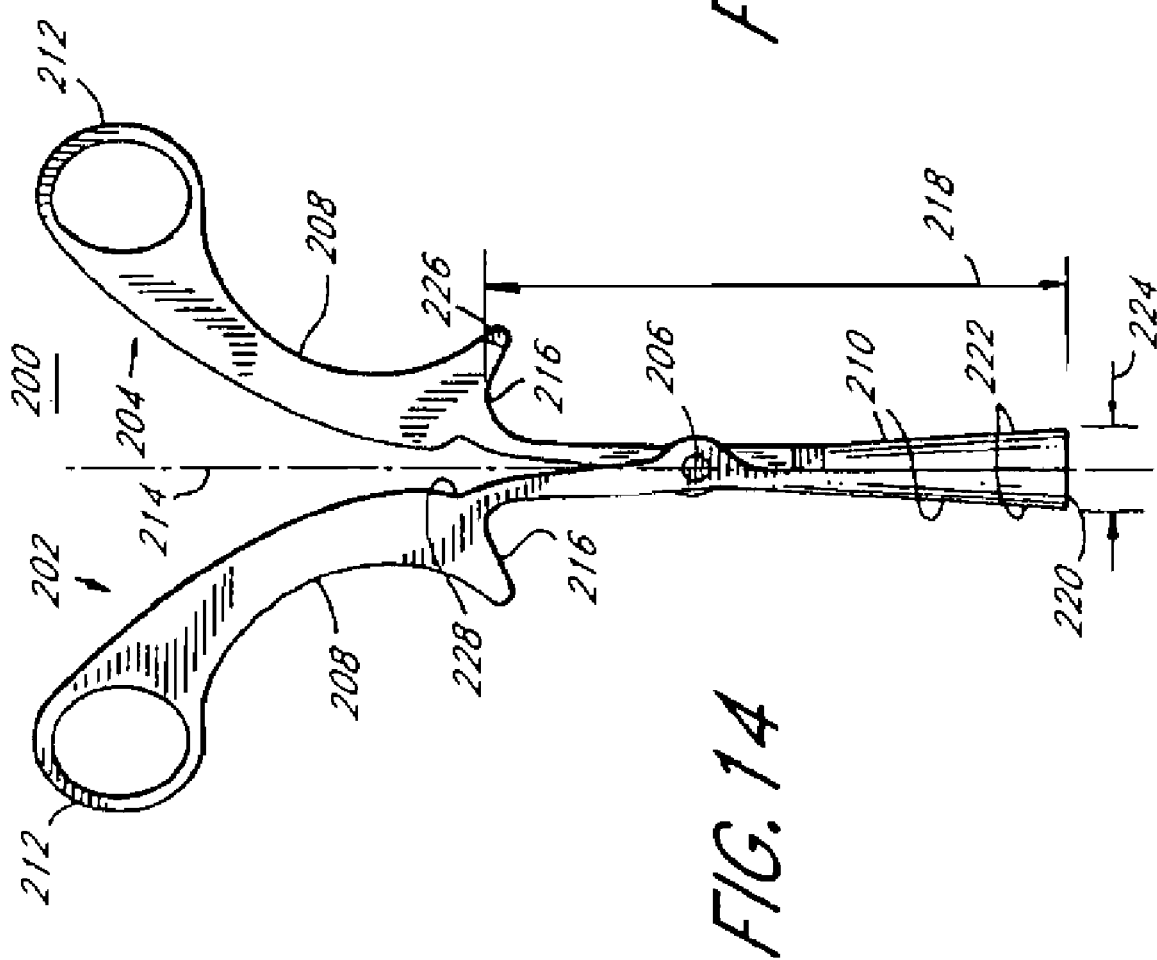
FIG. 14 is a side view of one embodiment of an expander apparatus in a reduced profile configuration.
Figure 18:
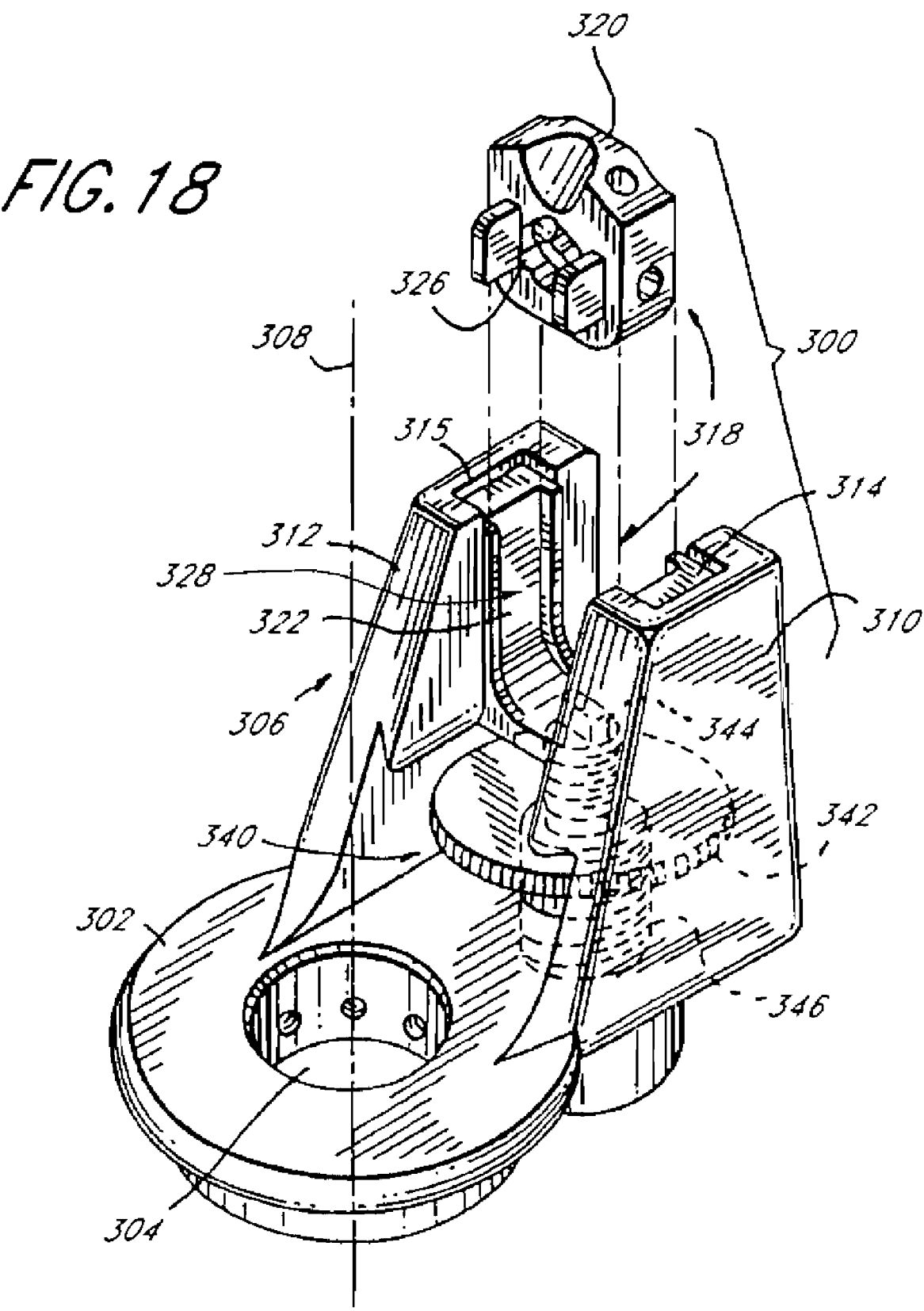
FIG. 18 is an exploded perspective view of one embodiment of an endoscope mount platform.

In some procedures, an expander apparatus is used to further expand the skirt portion 24 towards the enlarged configuration (illustrated in FIG. 4). The expander apparatus is inserted into the access device, and typically has two or more members that are movable to engage the interior wall of the skirt portion 24 and apply a force sufficient to further expand the skirt portion 24. FIGS. 14 and 15 show one embodiment of an expander apparatus 200 that has a first component 202 and a second component 204. The first component 202 and the second component 204 of the expander apparatus 200 are arranged in a tongs-like configuration and are pivotable about a pin 206. The first and second components 202 and 204 can be constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 preferably is dimensioned to engage the proximal end 25 of the access device 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the length of the access device 20, which in turn is a function of the depth of the body structures beneath the skin surface at which the surgical procedure is to be performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by arrows A in FIG. 15, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the access device 20 beyond its designed dimension, and to minimize trauma to the underlying tissue. Further features related to the expander apparatus are described in U.S. Pat. No. 6,652,553, issued Nov. 25, 2003, which is incorporated by reference in its entirety herein.

When the access device 20 is inserted into the patient and the outer sleeve 32 is removed, the skirt portion 24 expands to a point where the outward resilient expansion of the skirt portion 24 is balanced by the force of the surrounding tissue. The surgical space defined by the access device 20 may be sufficient to perform any of a number of surgical procedures or combination of surgical procedures described herein. However, if it is desired to expand the access device 20 further, the expander apparatus 200, or a similar device, may be inserted into the access device 20 in the reduced profile configuration until the shoulder portions 216 are in approximation with the proximal end 25 of the skirt portion 24 of the access device 20, as shown in FIG. 16.

Figure 16:
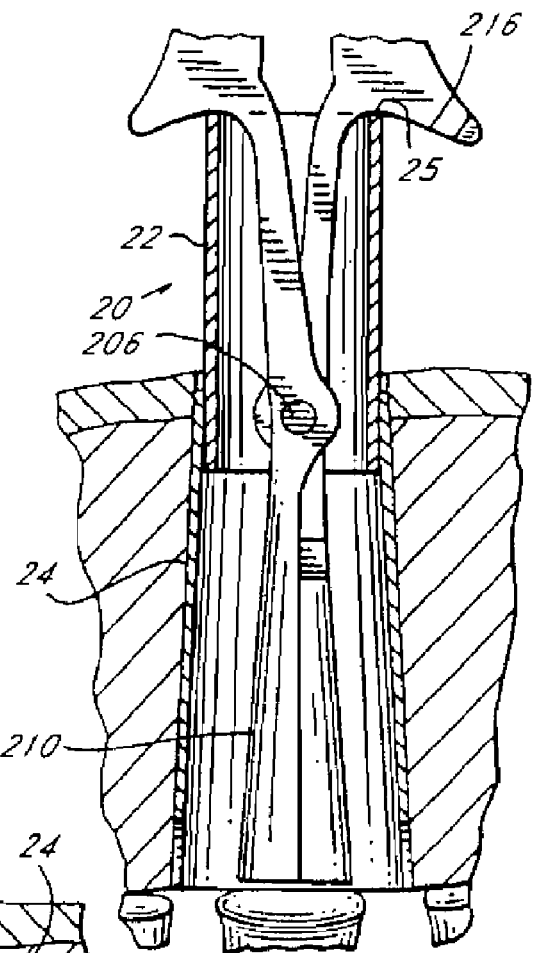
FIG. 16 is a sectional view of the expander apparatus of FIGS. 14-15 inserted into the access device of FIG. 2, which has been inserted into a patient.
Figure 17:
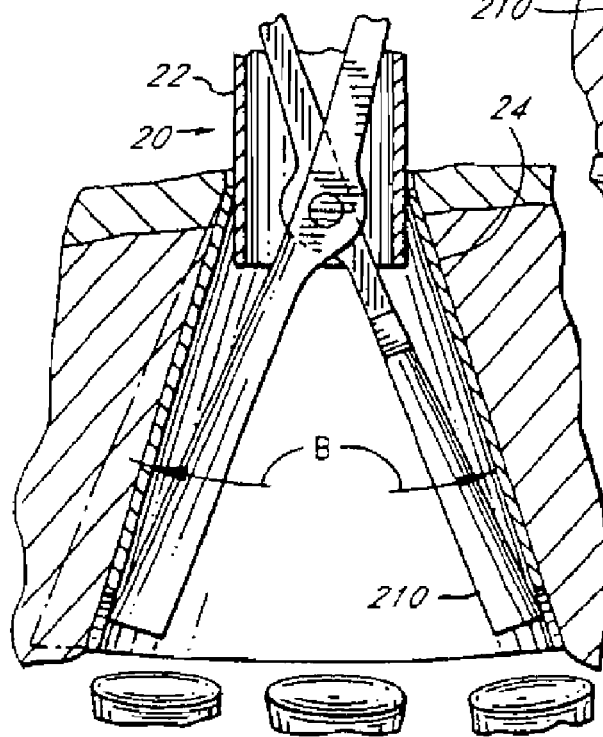
FIG. 17 is a sectional view of the expander apparatus of FIGS. 14-15 inserted into the access device of FIG. 2 and expanded to the expanded configuration to retract tissue.

FIG. 16 shows the expander apparatus 200 inserted in the access device 20 in the reduced profiled configuration. Expansion of the expander apparatus 200 is achieved by approximating the handle portions 212 (not shown in FIG. 16), which causes the distal portions 210 of the expander apparatus 200 to move to a spaced apart configuration. As the distal portions 210 move apart and contact the inner wall of the skirt portion 24, the rivet 44 is allowed to slide within the slots 46 and 48 of the skirt portion 24, thus permitting the skirt portion 24 to expand. When the distal portions 210 reach the maximum expansion of the skirt portion 24 (illustrated by a dashed line in FIG. 17), the tab 226 and shoulder portion 228 of the expander apparatus 200 come into engagement to prevent further expansion of the tongs-like portions (as illustrated in FIG. 15). Alternatively, the access device 20 may be expanded with another device that can selectively have a reduced profile configuration and an expanded configuration, e.g., a balloon or similar device.

An optional step in the procedure is to adjust the location of the distal portion of the access device 20 relative to the body structures to be operated on. For example, the expander apparatus 200 may also be used to engage the inner wall of the skirt portion 24 of the access device 20 in order to move the skirt portion 24 of the access device 20 to the desired location. For an embodiment in which the skirt portion 24 of the access device 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the access device, as described below.

B. Systems and Devices for Stabilization and Visualization

Some procedures can be conducted through the access device 20 without any additional peripheral components being connected thereto. In other procedures it may be beneficial to provide at least one of a support device and a viewing element. As discussed more fully below, support devices can be advantageously employed to provide support to peripheral equipment and to surgical tools of various types. Various embodiments of support devices and viewing elements are discussed herein below.

1. Support Devices

One type of support device that can be coupled with the access device 20 is a device that supports a viewing element. In one embodiment, an endoscope mount platform 300 and indexing arm 400 support an endoscope 500 on the proximal end 25 of the access device 20 for remotely viewing the surgical procedure, as illustrated in FIGS. 18-21. The endoscope mount platform 300 may also provide several other functions during the surgical procedure. The endoscope mount platform 300 preferably includes a base 302 that extends laterally from a central opening 304 in a generally ring-shaped configuration. In one application, the physician views the procedure primarily by observing a monitor, when inserting surgical instruments into the central opening 304. The base 302 advantageously enables the physician by providing a visual indicator (in that it may be observable in the physician's peripheral vision) as well as tactile feedback as instruments are lowered towards the central opening 304 and into the access device 20.

The endoscope mount platform 300 preferably has a guide portion 306 at a location off-set from the central opening 304 that extends substantially parallel to a longitudinal axis 308. The base 302 can be molded as one piece with the guide portion 306. The base 302 and guide portion 306 may be constructed with a suitable polymer, such as, for example, polyetheretherketone (PEEK).

The guide portion 306 includes a first upright member 310 that extends upward from the base 302 and a second upright member 312 that extends upward from the base 302. In one embodiment, the upright members 310, 312 each have a respective vertical grooves 314 and 315 that can slidably receive an endoscopic mount assembly 318.

Figure 25:
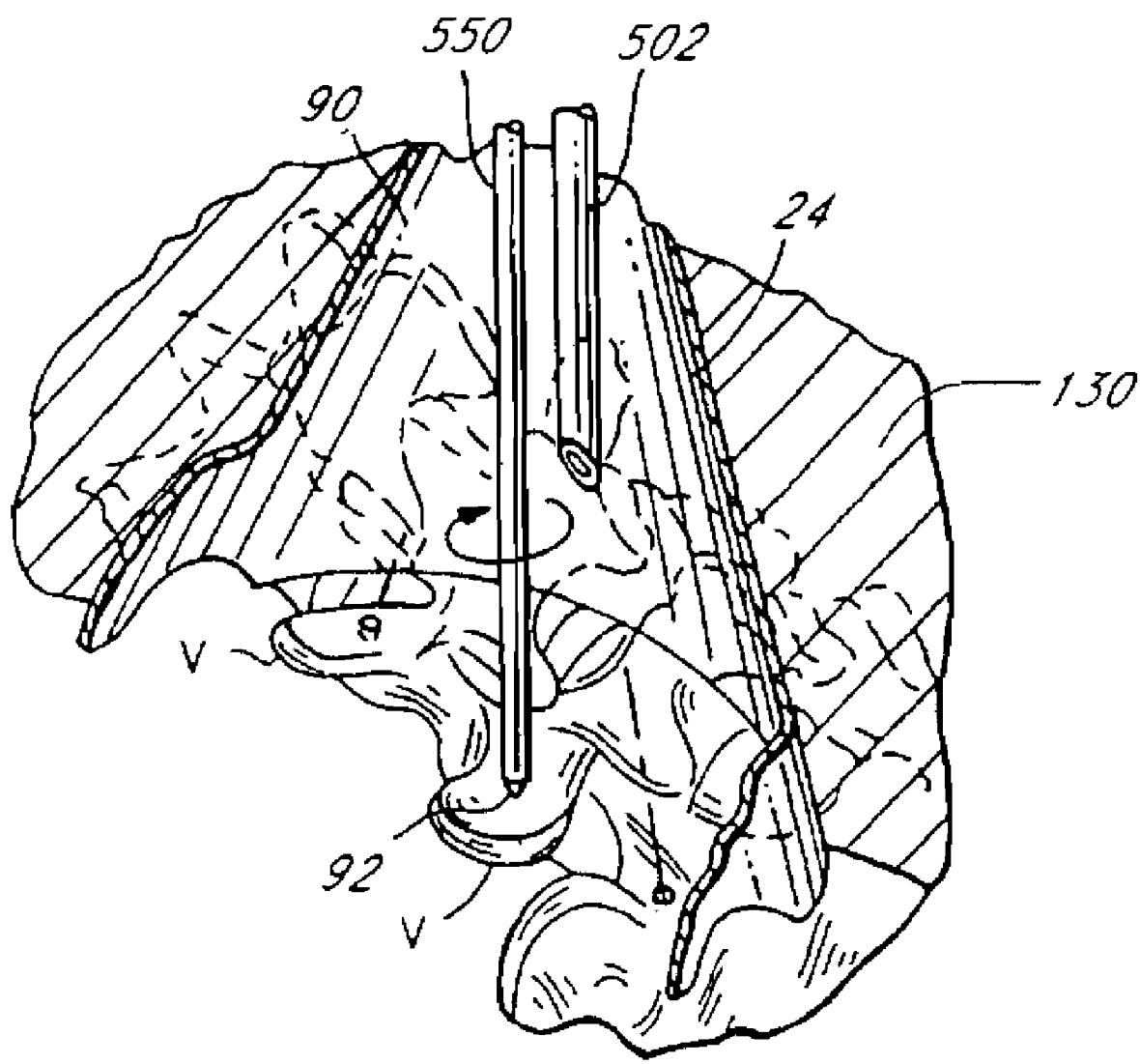
FIG. 25 is a partial sectional view of one stage of one application of a method for treating the spine of a patient.

The endoscope 500 (not shown in FIG. 18) can be movably mounted to the endoscope mount platform 300 with the endoscope mount assembly 318 in one embodiment. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the access device 20 substantially parallel to longitudinal axis 308 into the patient's body 130, as shown in FIG. 25.

The endoscope mount 320 is removably positioned in a recess 328 defined in the substantially "U"-shaped saddle unit 322. In one embodiment, the saddle unit 322 is selectively movable in a direction parallel to the longitudinal axis 308 in order to position the endoscope 500 at the desired height within the access device 20. The movement of the endoscope 500 by way of the saddle unit 322 also advantageously enables the physician to increase visualization of a particular portion of the surgical space defined by the access device, e.g., by way of a zoom feature, as required for a given procedure or a step of a procedure.

In one embodiment, an elevation adjustment mechanism 340, which may be a screw mechanism, is positioned on the base 302 between the upright members 310 and 312. The elevation adjustment mechanism 340 can be used to selectively move a viewing element, e.g., the endoscope 500 by way of the saddle unit 322. In one embodiment, the elevation adjustment mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 preferably has a first end received in a rectangular opening in the saddle unit 322, which inhibits rotational movement of the spindle 344. The second end of the spindle 344 has an external thread that cooperates with an internal thread formed in a bore within the thumb wheel 342. Rotation of the thumb wheel 342 relative to the spindle 344, causes relative axial movement of the spindle unit 344 along with the saddle unit 322. Further details and features related to endoscope mount platforms are described in U.S. Pat. No. 6,361,488, issued Mar. 26, 2002; U.S. Pat. No. 6,530,880, issued Mar. 11, 2003, and U.S. patent application Ser. No. 09/940,402, filed Aug. 27, 2001, published as Publication No. 2003/0040656 on Feb. 27, 2003, which are incorporated by reference in their entireties herein.

Figure 19:
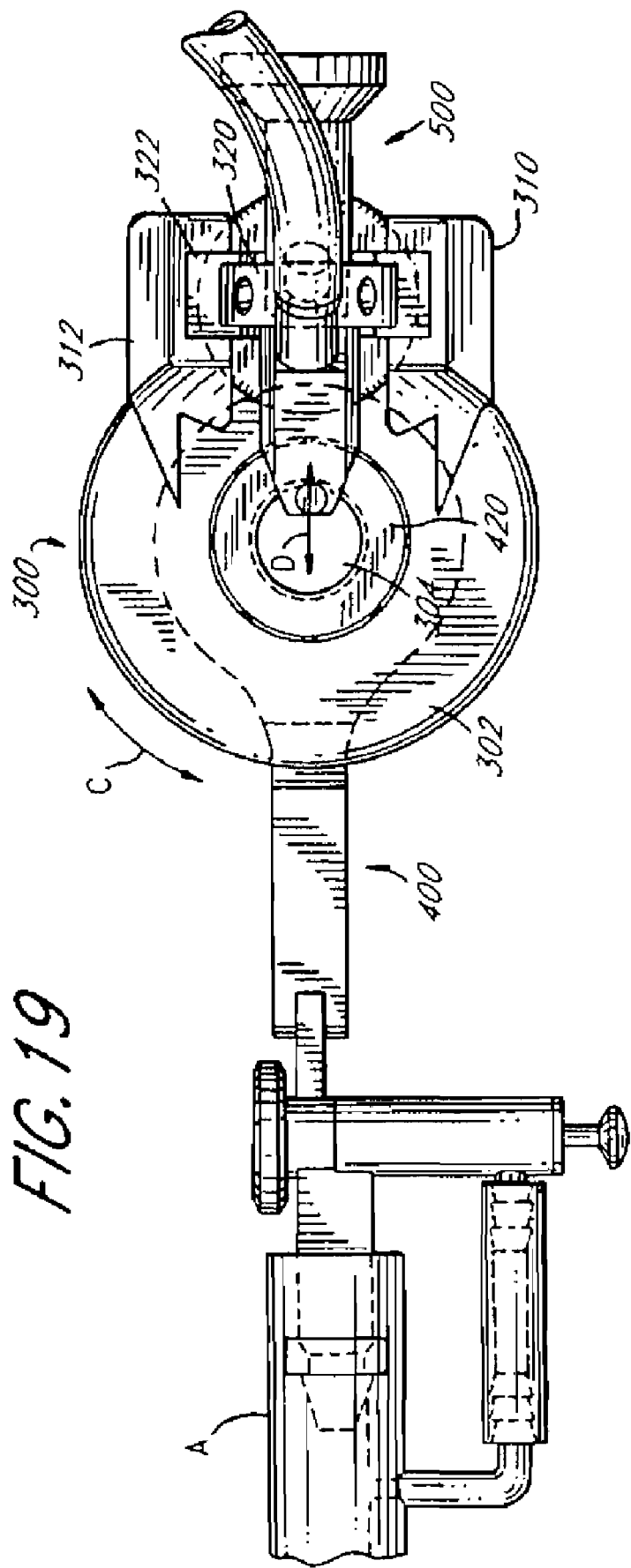
FIG. 19 is a top view of the endoscope mount platform of FIG. 18 coupled with one embodiment of an indexing arm and one embodiment of an endoscope.

FIGS. 19-21 show that the endoscope mount platform 300 is mountable to the support arm 400 in one embodiment. The support arm 400, in turn, preferably is mountable to a mechanical support, such as mechanical support arm A, discussed above in connection with FIG. 1. The support arm 400 preferably rests on, or is otherwise coupled to, the proximal end 25 of the access device 20. In one embodiment, the support arm 400 is coupled with an indexing collar 420, which is configured to be received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

In one embodiment, a plurality of collars 420 may be provided to make the surgical system 10 modular in that different access devices 20 may be used with a single endoscope mount platform 300. For example, access devices 20 of different dimensions may be supported by providing indexing collars 420 to accommodate each access device size while using a single endoscope mount platform 300. The central opening 304 of the endoscope mount platform 300 can have a constant dimension, e.g., a diameter of about 32.6 mm. An appropriate indexing collar 420 is selected, e.g., one that is appropriately sized to support a selected access device 20. Thus, the outer wall 422 and the outer diameter 430 are unchanged between different indexing collars 420, although the inner wall 424 and the inner diameter 432 vary to accommodate differently sized access devices 20.

The indexing collar 420 can be mounted to the proximal portion of the access device 20 to allow angular movement of the endoscope mount platform 300 with respect thereto about the longitudinal axis 308 (as indicated by an arrow C in FIG. 19). The outer wall 422 of the index collar 420 includes a plurality of hemispherical recesses 450 that can receive one or more ball plungers 350 on the endoscope mount platform 300 (indicated in dashed line). This arrangement permits the endoscope mount platform 300, along with the endoscope 500, to be fixed in a plurality of discrete angular positions.

Further details and features related to support arms and indexing collars are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001, published as Publication No. 2003/0040656 on Feb. 27, 2003, which are incorporated by reference in their entireties herein.

2. Viewing Elements

As discussed above, a variety of viewing elements and visualization techniques are embodied in variations of the surgical system 10. One viewing element that is provided in one embodiment is an endoscope.

FIG. 22 shows one embodiment of the endoscope 500 that has an elongated configuration that extends into the access device 20 in order to enable viewing of the surgical site. In particular, the endoscope 500 has an elongated rod portion 502 and a body portion 504. The rod portion 502 extends generally perpendicularly from the body portion 504. In one embodiment, the rod portion 502 of endoscope 500 has a diameter of about 4 mm and a length of about 106 mm. Body portion 504 may define a tubular portion 506 configured to be slidably received in the bore 326 of endoscope mount 320 as indicated by an arrow D. The slidable mounting of the endoscope 500 on the endoscope mount platform 300 permits the endoscope 500 to adjust to access device configurations that have different diameters. Additional mobility of the endoscope 500 in viewing the surgical site may be provided by rotating the endoscope mount platform 300 about the central axis 308 (as indicated by arrow C in FIG. 19).

The rod portion 502 supports an optical portion (not shown) at a distal end 508 thereof. In one embodiment, the rod portion 502 defines a field of view of about 105 degrees and a direction of view 511 of about 25-30 degrees. An eyepiece 512 preferably is positioned at an end portion of the body portion 504. A suitable camera (not shown) preferably is attached to the endoscope 500 adjacent the eyepiece 512 with a standard coupler unit. A light post 510 can supply illumination to the surgical site at the distal end portion 508. A preferred camera for use in the system and procedures described herein is a three chip unit that provides greater resolution to the viewed image than a single chip device.

FIGS. 23A, 23B, 23C, 24A, 24B, and 24C illustrate other embodiments of support devices and viewing elements. FIGS. 23A, 23B, and 23C illustrate one embodiment of a lighting element 520 coupled with a support arm 522 compatible with an access device 524 having a proximal portion with a generally circular cross section. In other embodiments, support arms can be configured to be coupled with access devices having proximal portions with generally oblong or oval cross sections.

The support arm 522 preferably is coupled with the access device 524 to provide support for the access device 524 during a procedure. As shown in FIGS. 23A, 23B, and 23C, the support arm 522 comprises a pneumatic element 526 for maintaining the support arm 522 in a desired position. Depressing a button 528 coupled with a valve of the pneumatic element 526 releases pressure and allows the support arm 522 and access device 524 to be moved relative the patient 530. Releasing the button 528 of the pneumatic element 526 increases pressure and maintains the access device 524 and support arm 522 in the desired position. The support arm 522, as shown, is configured for use with a mechanical arm using a suction, or a vacuum to maintain the access device in a desired location. One of skill in the art will recognize that various other support arms and mechanical arms can be used. For example, commercially available mechanical arms having clamping mechanisms can be used as well as suction or pressure based arms.

The support arm 522 can comprise an inner ring portion 532 and an outer ring portion 534 for surrounding the access device 524 at its proximal end. In the illustrated embodiment, the inner and outer ring portions 532, 534 are fixed relative each other. In other embodiments the inner and outer ring portions 532, 534 can move relative each other. The support arm 522 preferably comprises a lighting element support portion 536. In the illustrated embodiment, the lighting element support portion 536 extends above upper surfaces of the inner and outer ring portions 532, 534. The lighting element support portion 536 can extend from the inner ring portion 532, the outer ring portion 534, or both. The lighting element support portion 536 can have a notch or groove 538 for receiving and supporting the lighting element 520. Additionally, the lighting element support portion 536 can have one or more prongs extending at least partially over the lighting element 520 to hold it in place.

In the illustrated embodiment, the lighting element 520 has an elongated proximal portion 540 and a curved distal portion 542. The proximal portion 540 of the lighting element 520 preferably is coupled with a light source (not shown). The curved distal portion of the lighting element 520 in one embodiment extends only a short distance into the access device and is configured to direct light from the light source down into the access device 524. In another embodiment, the lighting element 520 can be provided such that it does not extend into the access device. In such an embodiment, the right portions 532 and 534 only partially surround the proximal end of the access device 524. Providing a lighting element 520 for use with the access device 524 preferably allows a user to see down into the access device 524 to view a surgical location. Accordingly, use of a lighting element 520 in some cases, enables the user to perform a procedure, in whole or in part, without the use of an endoscope. In one embodiment, the lighting element 520 enables a surgeon to perform the procedure with the use of microscopes or loupes.

FIGS. 24A, 24B, and 24C illustrate other embodiments of visualization elements. As shown in FIG. 24A, a lighting element 560 comprises a support member 562, an access device insert 564, and fiber optic elements 566. The support member 562 has a proximal end 568, a central portion 570, and a distal end 572. The proximal end 568 preferably has a coupling portion 574 for coupling the support member 562 to a support arm or other support system (not shown). The central portion 570 preferably is coupled with the fiber optic elements 566 to provide support there to. The distal end 572 preferably is coupled with the access device insert 564.

In the illustrated embodiment, the access device insert 564 is configured to be inserted in an access device having a proximal portion with a generally circular cross section. The access device insert 564 is coupled with the fiber optic elements 566. The fiber optic elements 566 extend down into the access device insert 564 so that the ends of the fiber optic elements 566 can direct light down inside an access device along side portions there of.

FIGS. 24B and 24C illustrate other embodiments of visualization elements similar to the embodiment described with reference to FIG. 24A. In the illustrated embodiments, the access device inserts 564 are configured to be inserted into access devices having proximal portions with generally oblong, or oval, cross sections. As shown in FIG. 24B, the access device insert 564 has a generally oblong or oval shaped cross section. The access device insert 564 is coupled with the fiber optic elements 566 along a longer side surface of the access device insert 564. As shown in FIG. 24C, the access device insert 564 has a generally oblong or oval shaped cross section. The access device insert 564 is coupled with the fiber optic elements 566 along a shorter side surface of the access device insert 564. Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

C. Apparatuses and Methods for Performing Spinal Procedures

The surgical assembly 10 described above can be deployed to perform a wide variety of surgical procedures on the spine. In many cases, the procedures are facilitated by inserting the access device and configuring it to provide greater access to a surgical location, as discussed above and by mounting the support arm 400 and the endoscope mount platform 300 on the proximal portion, e.g., on the proximal end 25, of the access device 20 (FIGS. 1 and 22). As discussed above, visualization of the surgical location is enhanced by mounting a viewing element, such as the endoscope 500, on the endoscope mount platform 300. Having established increased access to and visualization of the surgical location, a number of procedures may be effectively performed.

Generally, the procedures involve inserting one or more surgical instruments into the access device 20 to manipulate or act on the body structures that are located at least partially within the operative space defined by the expanded portion of the access device 20. FIG. 25 shows that in one method, the skirt portion 24 of access device 20 at least partially defines a surgical site or operative space 90 in which the surgical procedures described herein may be performed. Depending upon the overlap of the skirt portion, the skirt portion may define a surface which is continuous about the perimeter or which is discontinuous, having one or more gaps where the material of the skirt portion does not overlap.

One procedure performable through the access device 20, described in greater detail below, is a two-level spinal fusion and fixation. Surgical instruments inserted into the access device may be used for debridement and decortication. In particular, the soft tissue, such as fat and muscle, covering the vertebrae may be removed in order to allow the physician to visually identify the various "landmarks," or vertebral structures, which enable the physician to determine the location for attaching a fastener, such a fastener 600, discussed below, or other procedures, as will be described herein. Enabling visual identification of the vertebral structures enables the physician to perform the procedure while viewing the surgical area through the endoscope, microscope, loupes, or other viewing element, or in a conventional, open manner.

Tissue debridement and decortication of bone are completed using one or more of a debrider blades, a bipolar sheath, a high speed burr, and any other conventional manual instrument. The debrider blades are used to excise, remove and aspirate the soft tissue. The bipolar sheath is used to achieve hemostasis through spot and bulk tissue coagulation. Additional features of debrider blades and bipolar sheaths are described in U.S. Pat. No. 6,193,715, assigned to Medical Scientific, Inc., which is incorporated by reference in its entirety herein. The high speed burr and conventional manual instruments are also used to continue to expose the structure of the vertebrae.

1. Fixation Systems and Devices

Having increased visualization of the pertinent anatomical structure, various procedures may be carried out on the structures. In one procedure, one or more fasteners are attached to adjacent vertebrae V. As discussed in more detail below, the fasteners can be used to provide temporary or permanent fixation and to provide dynamic stabilization of the vertebrae V. These procedures may combined with other procedures, such as procedures employing other types of implant, e.g., procedures employing fusion devices, prosthetic disc components, or other suitable implants. In some procedures, fasteners are attached to the vertebrae before or after fusion devices are inserted between the vertebrae V. Fusion systems and devices are discussed further below.

In one application, the desired location and orientation of the fastener is determined before the fastener is applied to the vertebra. The desired location and orientation of the fastener may be determined in any suitable manner. For example, the pedicle entry point of the L5 vertebrae may be located by identifying visual landmarks alone or in combination with lateral and A/P fluoroscopy, as is known in the art. With continued reference to FIG. 25, an entry point 92 into the vertebra V is prepared. In procedure, the entry point 92 may be prepared with an awl 550. The entry point 92 corresponds to the pedicle in one procedure. The entry point 92 may be prepared in any suitable manner, e.g., employing a bone probe, a tap, and a sounder to create and verify the integrity of the prepared vertebra. The sounder, as is known in the art, determines whether the hole that is made is surrounded by bone on all sides, and can be used to confirm that there has been no perforation of the pedicle wall.

After the hole in the pedicle beneath the entry point 92 is prepared, a fastener may be advanced into the hole. Prior to advancing the fastener, or at any other point during the procedure, it may be desirable to adjust the location of the distal portion of the access device 20. The distal portion of the access device 20 may be adjusted by inserting the expander apparatus 200 into the access device 20, expanding the distal portions 210, and contacting the inner wall of the skirt portion 24 to move the skirt portion 24 to the desired location. This step may be performed while the endoscope 500 is positioned within the access device 20, and without substantially disturbing the location of the proximal portion of the access device 20 to which the endoscope mount platform 300 may be attached.

FIGS. 26-27 illustrate one embodiment of a fastener 600 that is particularly applicable in procedures involving fixation. The fastener 600 preferably includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole that extends away from the entry point 92 into the vertebrae, as will be described below. The substantially spherical joint portion 614 is received in a substantially annular, partly spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604 until the joint portion 614 engages the annular recess 616. The screw portion 602 is retained in the housing 604 by the spacer member 606 and by the biasing member 608. The biasing member 608 provides a biasing force to drive the spacer member 606 into frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 preferably is selected such that biasing force prevents unrestricted movement of the housing 604 relative to the screw portion 602. However, in some embodiments the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27A illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 that is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright members 630 and 631. Elongated member 650 preferably is configured to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

Additional features of the fastener 600 are also described in U.S. patent application Ser. No. 10/075,668, filed Feb. 13, 2002, published as U.S. Application Publication No. 2003/0153911A1 on Aug. 14, 2003, and application Ser. No. 10/087,489, filed Mar. 1, 2002, published as U.S. Application Publication No. 2003/0167058A1 on Sep. 4, 2003, which are incorporated by reference in their entireties herein.

According to one application, the fastener 600 is inserted into the access device 20 and guided to the prepared hole at the entry point 92 in the vertebrae. The fastener 600 preferably is simultaneously supported and advanced into the hole so that the fastener 600 is secured in the in the hole beneath the entry point 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

The distal tool portion 666, as illustrated in greater detail in FIG. 29 includes a substantially hexagonal outer periphery that is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel or a groove is provided in the tip portion 666 for receiving the spring member 672. The channel or groove includes a medial longitudinal notch portion 676, a proximal, angled channel portion 678, and a distal substantially transverse channel portion 680. The spring member 672 is preferably manufactured from stainless steel and has a medial portion 682, proximal portion 684, and a transverse distal portion 686. The medial portion 682 is partially received in the longitudinal notch portion 676. The proximal portion 684 preferably is angled with respect to the medial portion 682 and is fixedly received in the angled channel portion 678. The transverse distal portion 686 preferably is slidably received in the transverse channel 680. The medial portion 682 of the spring member 672 is partially exposed from the distal tip portion 666 and normally is biased in a transverse outward direction with respect to the longitudinal axis (indicated by arrow E), in order to supply bearing force against the wall of the recess 628. Alternatively, the distal tip portion of the screwdriver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666. Other means may be provided for temporarily but securely coupling the fastener 600 with the screwdriver distal tip 666.

The insertion of the fastener 600 into the prepared hole that extends into the vertebrae from the entry point 92 may be achieved by insertion of screwdriver 660 into access device 20 (indicated by arrow G). This procedure may be visualized by the use of the endoscope 500 in conjunction with fluoroscopy, or by way of any other suitable viewing element. The screw portion 602 is threadedly advanced by the endoscopic screwdriver 660 into the prepared hole that extends beneath the entry point 92 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the access device 20. An alternative method may use a guidewire, which is fixed in the hole beneath the entry point 92, and a cannulated screw which has an internal lumen and is guided over the guidewire into the hole beneath the entry point 92. Where a guidewire system is used, the screwdriver also would be cannulated so that the screwdriver would fit over the guidewire.

For a two-level fixation, it may be necessary to prepare several holes and attach several fasteners 600. Preferably, the access device 20 is sized to provide simultaneous access to all vertebrae in which the surgical procedure is being performed. In some cases, however, additional enlargement or repositioning of the distal portion of the access device 20 may be helpful in providing sufficient access to the outer vertebrae, e.g., the L4 and S1 vertebrae. In the illustrated embodiment, the expander apparatus 200 may be repeatedly inserted into the access device 20 and expanded in order to further open or to position the skirt portion 24. In one procedure, additional fasteners are inserted in the L4 and S1 vertebrae in a similar fashion as the fastener 600 inserted into the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In one application, after the fasteners 600 are advanced into the vertebrae, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step is performed, described below.

Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. Pivoting the movable handle 714 towards stationary handle 712 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

In one application, the elongated member 650 is inserted into the access device 20. In one application, the elongated member 650 is manufactured from a biocompatible material and is sufficiently strong to maintain the position of the vertebrae, or other body structures, coupled by the elongate member 650 with little or no relative motion therebetween. In one embodiment, the elongated members 650 are manufactured from Titanium 6/4 or titanium alloy. The elongated member 650 also may be manufactured from stainless steel or any other suitable material. The transverse shape, width (e.g., radii), and lengths of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

Figure 30:
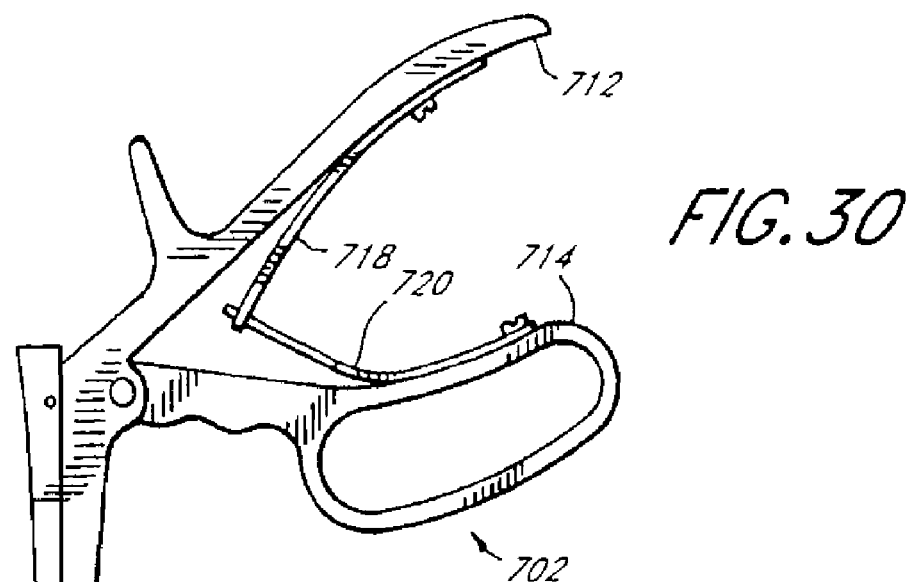
FIG. 30 is side view of one embodiment of another surgical instrument.

In one application, the elongated member 650 is fixed to each of the fasteners 600, and more particularly, to the housings 604 of each fastener 600. The grasper apparatus 700, described above, is also particularly useful for inserting the elongated member 650 into the access device 20 and positioning it with respect to each housing 604. As illustrated in FIG. 30, the jaws 708a and 708b of the grasper apparatus 700 each has shaped (e.g., curved) contact portions 722a and 722b for contacting and holding the outer surface of the elongated member 650.

Figure 31:
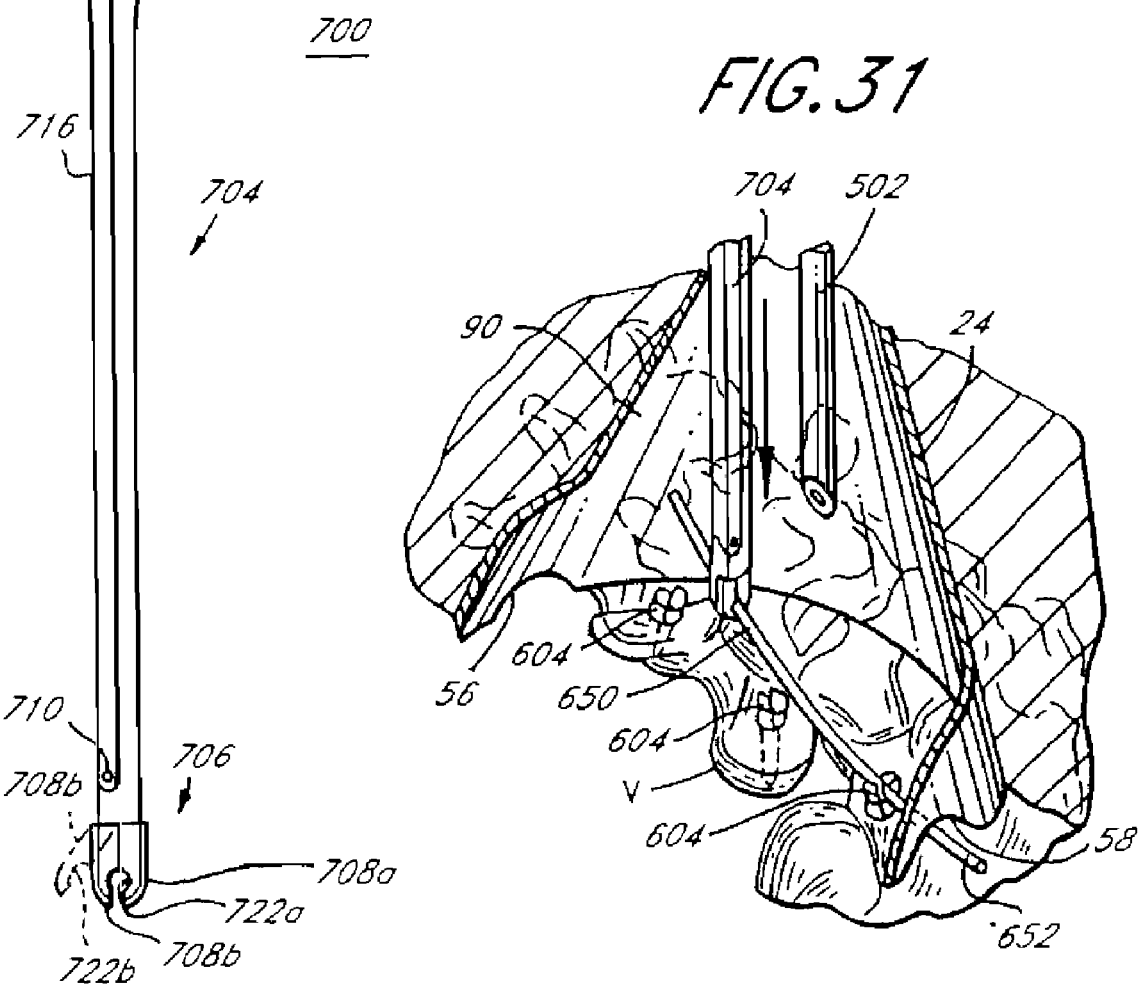
FIG. 31 is a partial sectional view of one stage of one application for treating the spine of a patient.

As illustrated in FIG. 31, the grasper apparatus 700 may be used to insert the elongated member 650 into the operative space 90 defined at least partially by the skirt portion 24 of the access device 20. In some embodiments, the cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housings 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In one embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion 802 extends transverse to the longitudinal axis 810, which allows the physician to adjust the guide apparatus 800 without interfering with the operation of the screwdriver 660.

The distal portion 806 of the apparatus includes several shaped cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location. In the illustrated embodiment, the cut out portions 814 are semicircular, to match the round elongated member 650. However, other shaped cut out portions may be provided to match other shaped elongated members.

As illustrated in FIG. 34, the guide apparatus 800 is used in cooperation with the endoscopic screwdriver 660 to attach the cap screw 610. The distal end of the body portion 804 includes a pair of elongated openings 816. The openings 816 provide a window to enable the physician to endoscopically view the cap screw 610 retained at the distal tip 666 of the endoscopic screw driver 660. Fewer or more than two openings can be provided and the openings 816 need not be elongated.

The guide apparatus 800 and the endoscopic screwdriver 660 cooperate as follows in one application. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
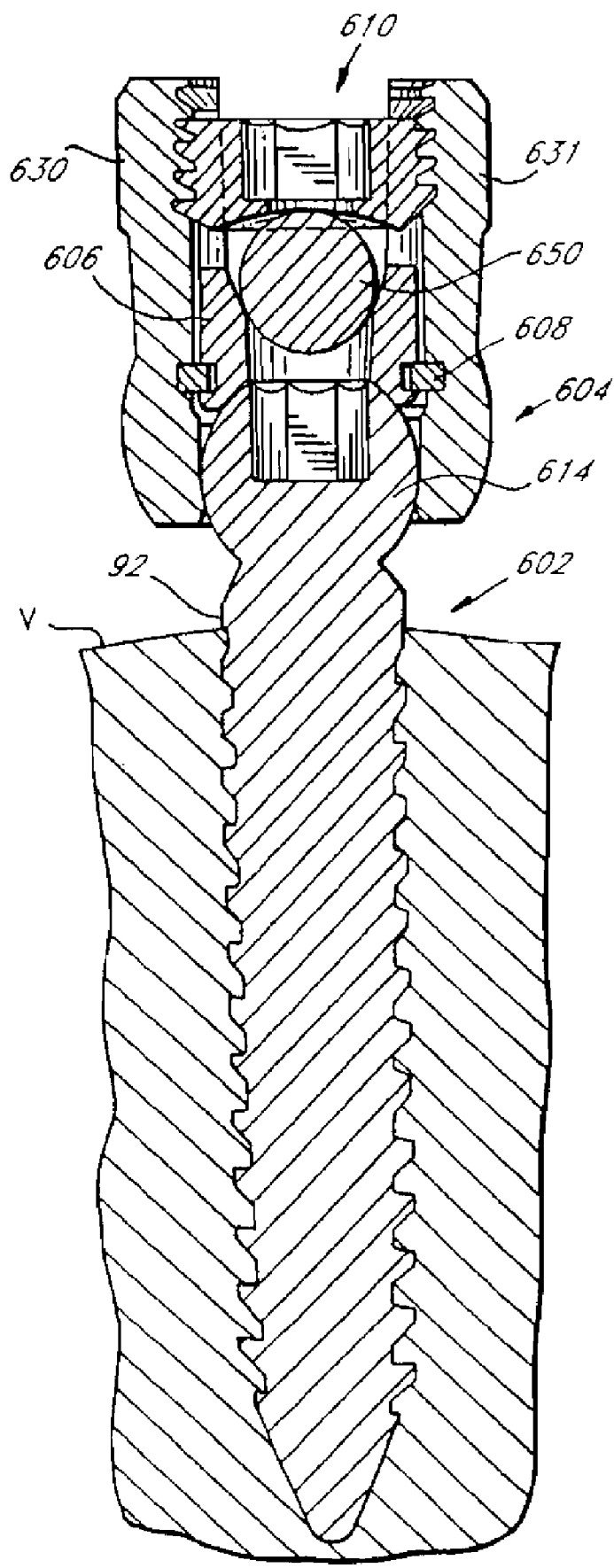
FIG. 35 is an enlarged sectional similar to FIG. 34, illustrating one stage of one application for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as a compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of one embodiment of the compressor-distractor instrument 900 is illustrated in FIG. 36. The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In one embodiment, spacing member 906 comprises a jaw portion that is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis. (Further details and features related to compressor-distractor apparatuses are described in U.S. application Ser. No. 10/178,875, filed Jun. 24, 2002, entitled "Surgical Instrument for Moving Vertebrae," published as U.S. Patent Application Publication No. 2003/0236529A1 on Dec. 25, 2003, which is incorporated by reference in its entirety herein. Additionally, further details related to instrumentation for moving a vertebra are described in U.S. Pat. No. 6,648,888, issued Nov. 18, 2003; PCT Application No. PCT/US02/28106, filed Sep. 5, 2002, titled SURGICAL INSTRUMENT FOR MOVING VERTEBRAE; PCT Application No. PCT/US03/27879, filed Sep. 5, 2003, titled SURGICAL INSTRUMENT FOR MOVING A VERTEBRAE; and PCT Application No. PCT/US03/04361, filed Feb. 13, 2003, titled APPARATUS FOR CONNECTING A LONGITUDINAL MEMBER TO A BONE PORTION, which are hereby incorporated by reference in their entireties herein.)

As illustrated in FIG. 36, the spacer member 906 can be opened with respect to the driver portion 904 to space the vertebrae farther apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 910 of the spacer member 906 engages the housing 604b of the fastener 600b and moves the fastener 600b towards the fastener 600a. When the spacing of the vertebrae is acceptable to the physician, the cap screw 610a is tightened by the driver member 904, thereby fixing the relationship of the housing 604a with respect to the elongated member 650, and thereby fixing the position of the vertebrae, or other bone structures, with respect to one another. In one application, once the elongated member 650 is fixed with respect to the fasteners 600, the fixation portion of the procedure is substantially complete.

2. Fusion Systems and Devices

Although fixation may provide sufficient stabilization, in some cases it is also desirable to provide additional stabilization. For example, where one or more discs has degraded to the point that it needs to be replaced, it may be desirable to position an implant, e.g., a fusion device, a prosthetic disc, a disc nucleus, etc., in the intervertebral space formerly occupied by the disc.

Figure 48:
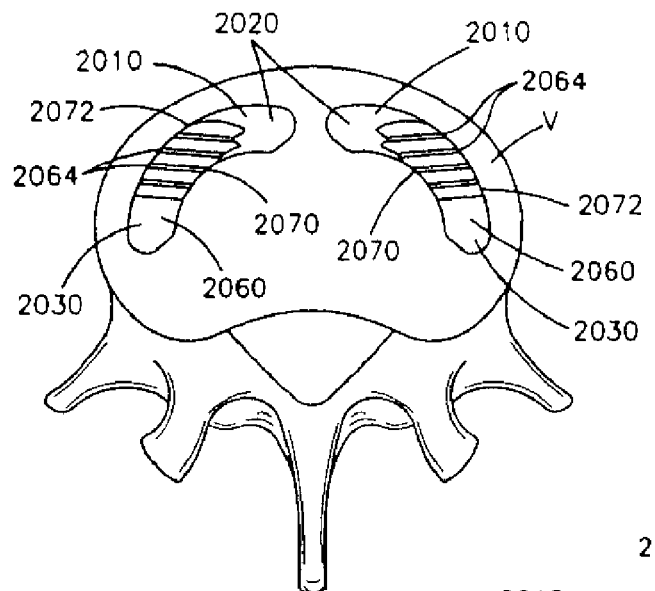
FIG. 48 is a view showing a pair of the spinal implants of FIG. 38 in first relative positions between adjacent vertebrae.
Figure 49:
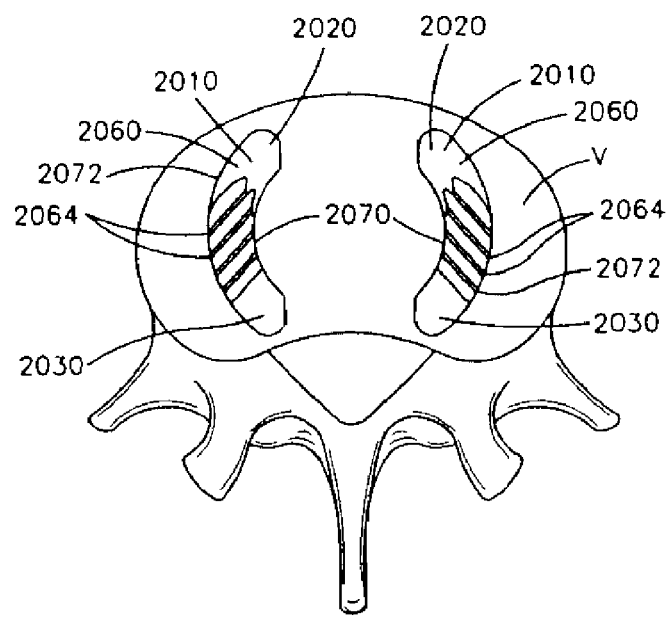
FIG. 49 is a view showing a pair of the spinal implants of FIG. 38 in second relative positions between adjacent vertebrae.

In one application, a fusion device is inserted between adjacent vertebrae V. Portions of the fusion procedure can be performed before, during, or after portions of the fixation procedure. FIGS. 38-42 illustrate one embodiment of a fusion device, referred to herein as a spinal implant 2010, that is inserted between adjacent vertebrae. The spinal implant 2010 preferably is placed between adjacent vertebrae to provide sufficient support to allow fusion of the adjacent vertebrae, as shown in FIGS. 48-49. The spinal implants 2010 are preferably made from an allograft material, though other materials could also be used, including autograft, xenograft, or some non-biologic biocompatible material, such as titanium or stainless steel. Also, where non-biologic materials are used, the implant 2010 may be configured as a cage or other suitable configuration.

Figure 41:
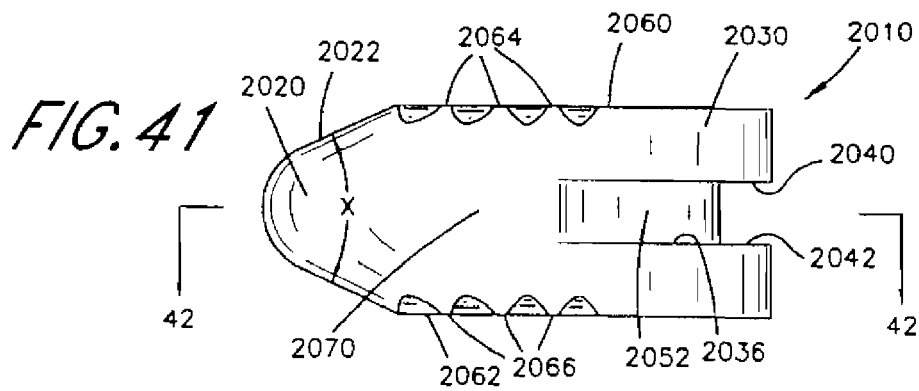
FIG. 41 is a side view of the spinal implant of FIG. 38 showing the first side surface.
Figure 42:
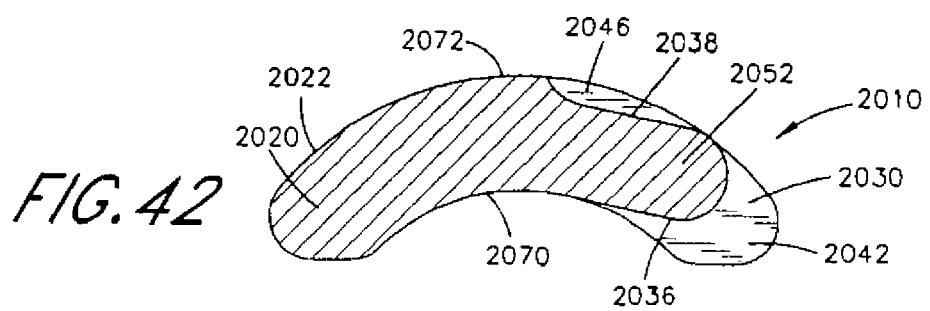
FIG. 42 is a cross-sectional view of the spinal implant taken along the line 42-42 in FIG. 41.

The spinal implant 2010 (FIGS. 38-42) has a first end 2020 for insertion between adjacent vertebrae V. The first end 2020 has a tapered surface 2022 to facilitate insertion of the implant between adjacent vertebrae V. The surface 2022 defines an angle X of approximately 45° as shown in FIG. 41.

Figure 51:
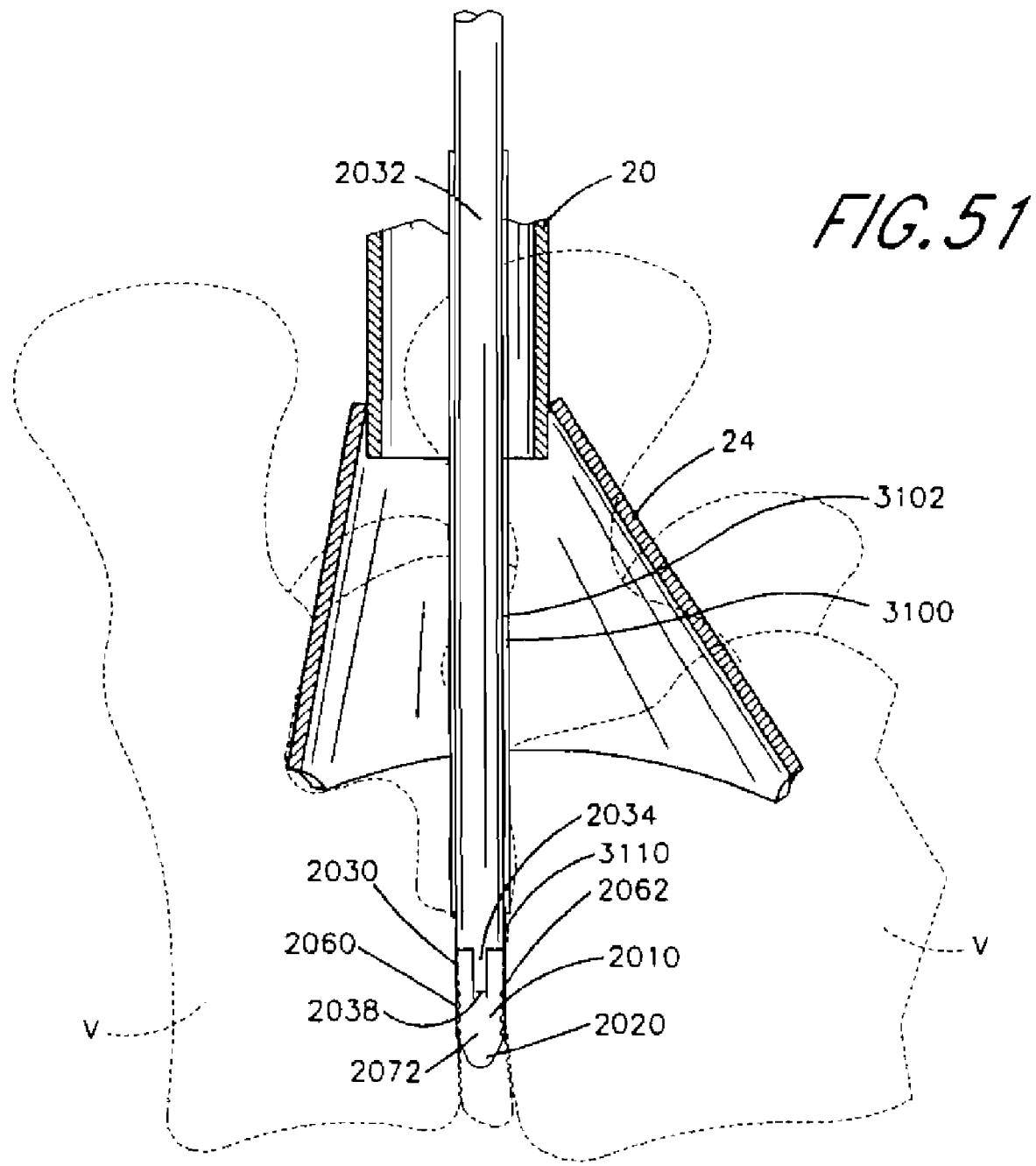
FIG. 51 is a view showing a spinal implant being inserted between the adjacent vertebrae according to one application.
Figure 52:
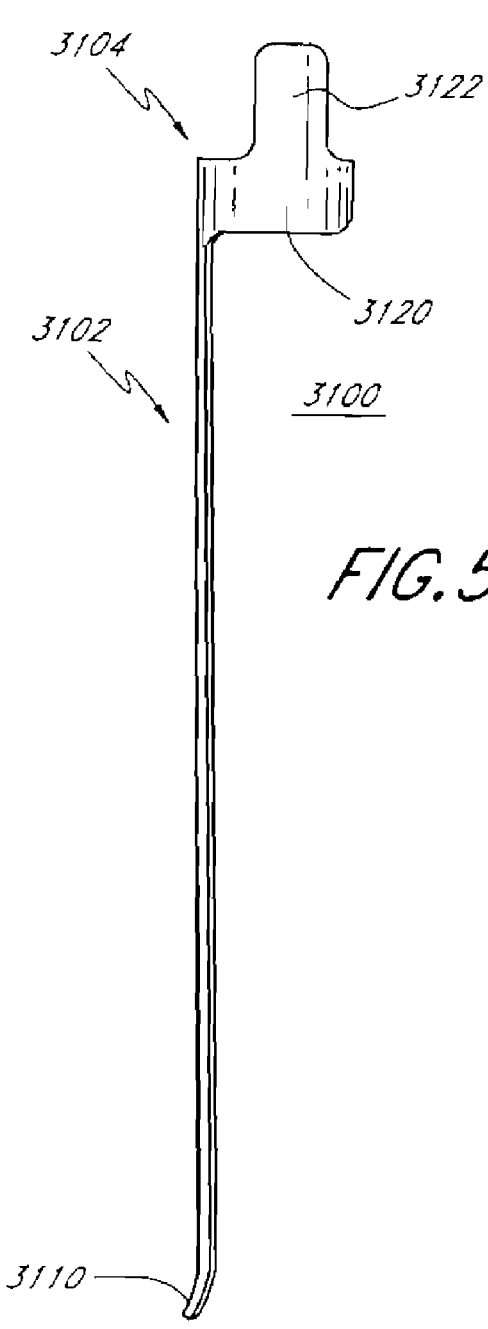
FIG. 52 is a side view of an apparatus according to another embodiment.
Figure 53:
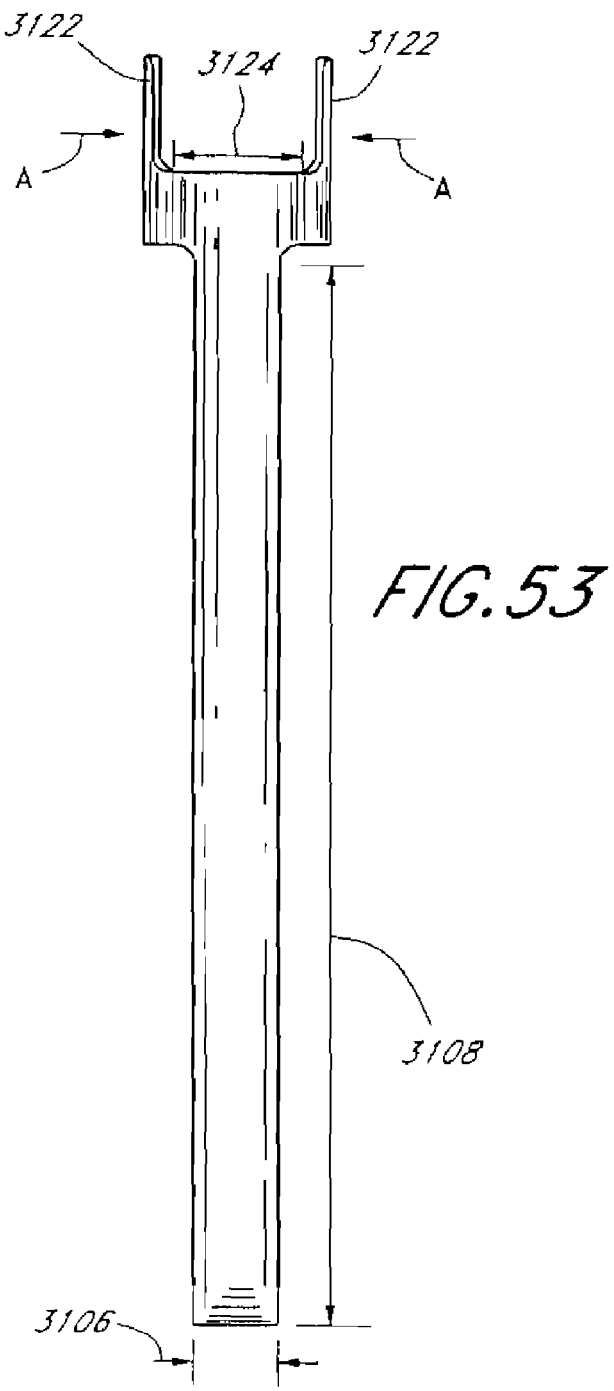
FIG. 53 is a front view of the apparatus of FIG. 52.
Figure 54:
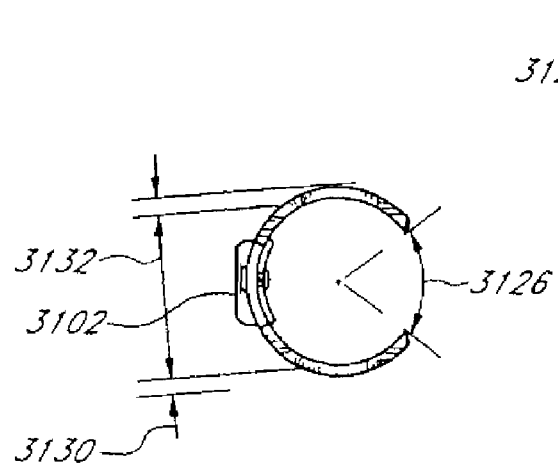
FIG. 54 is a top view of the apparatus of FIG. 52.
Figure 56:
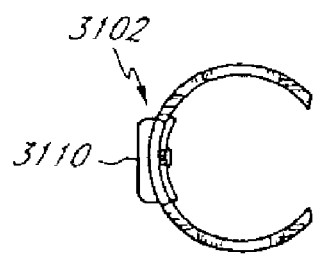
FIG. 56 is a bottom view of the apparatus of FIG. 52.
Figure 55:
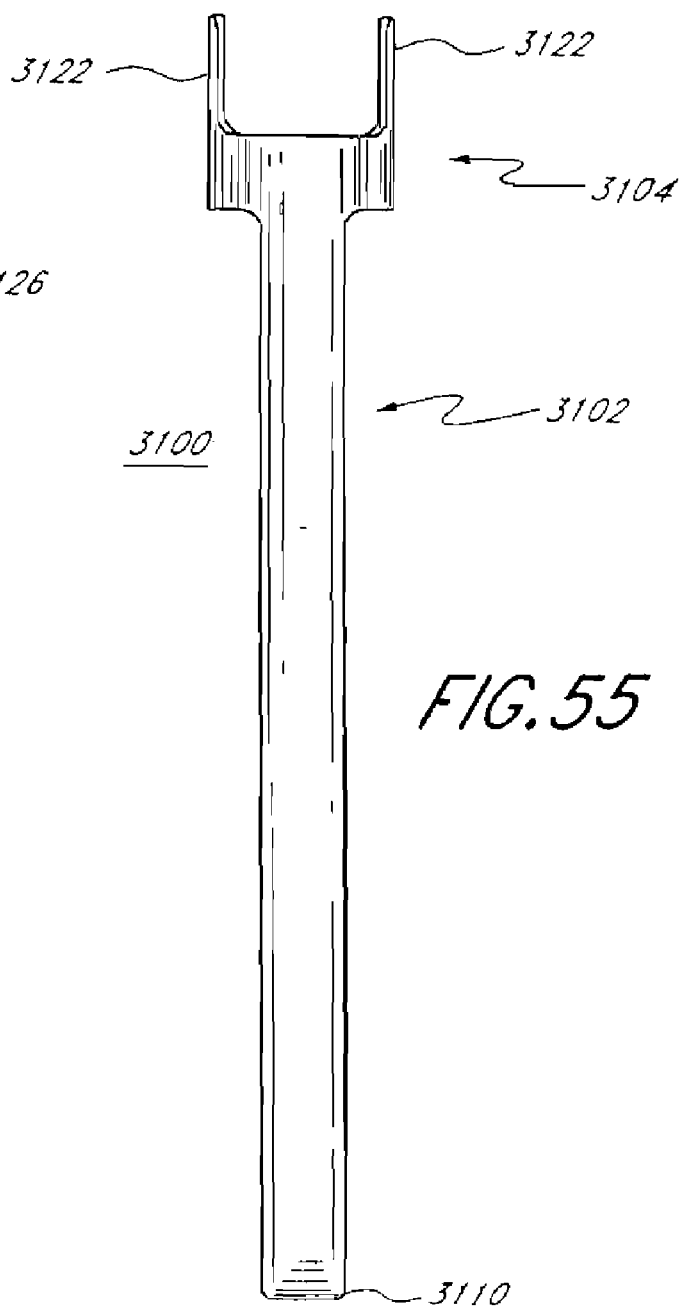
FIG. 55 is a back view of the apparatus of FIG. 52.

The spinal implant 2010 (FIGS. 38-39) has a second end 2030 that is engageable with a tool 2032 (FIG. 51) for inserting the implant between the adjacent vertebrae V. The tool 2032 has a pair of projections 2034, one of which is shown in FIG. 51, that extend into recesses 2036 and 2038 in the end 2030 of the implant 2010. The recesses 2036 and 2038 (FIGS. 38-39) extend from the second end 2030 toward the first end 2020. The recess 2036 (FIG. 41) is defined by an upper surface 2040 and a lower surface 2042 extending generally parallel to the upper surface 2040. The recess 2038 (FIG. 39) has a lower surface 2046 and an upper surface 2048. The upper surface 2048 extends generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 can grip the implant 2010 for inserting the implant between the adjacent vertebrae V.

Figures 38, 39:
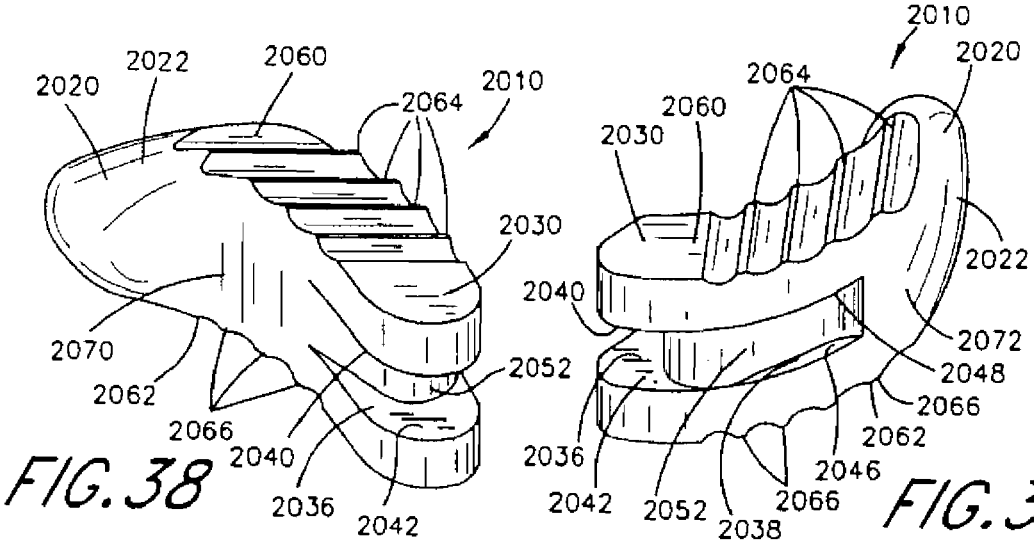
FIG. 38 is a perspective view of a spinal implant or fusion device constructed according to another embodiment showing a first side surface of the spinal implant.
FIG. 39 is a perspective view of the spinal implant of FIG. 38 showing a second side surface of the spinal implant.
Figure 40:
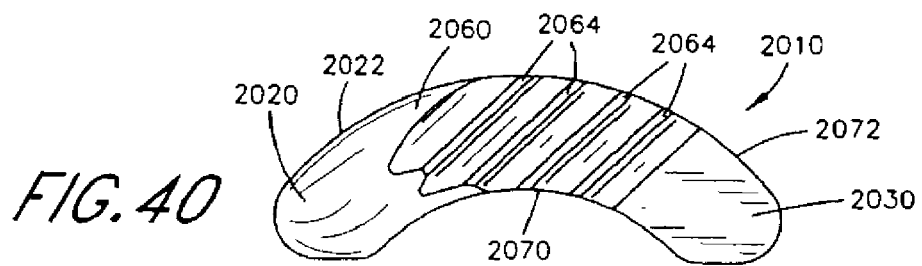
FIG. 40 is a plan view of the spinal implant of FIG. 38 showing an upper surface of the spinal implant.

As viewed in FIGS. 38-41, the implant 2010 has an upper surface 2060 for engaging the upper vertebra V. The implant 2010 has a lower surface 2062, as viewed in FIGS. 38-41, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 38-39 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 extend parallel to each other and extend between the side surfaces 2070 and 2072 and along secant lines of the concentric circles defined by the side surfaces.

The implant 2010 preferably is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters can be used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 48. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that in some embodiments only one implant 2010 may be inserted between the vertebrae V. Furthermore, it is contemplated that the implants 2010 may be inserted between vertebrae using an open procedure.

Figure 50:
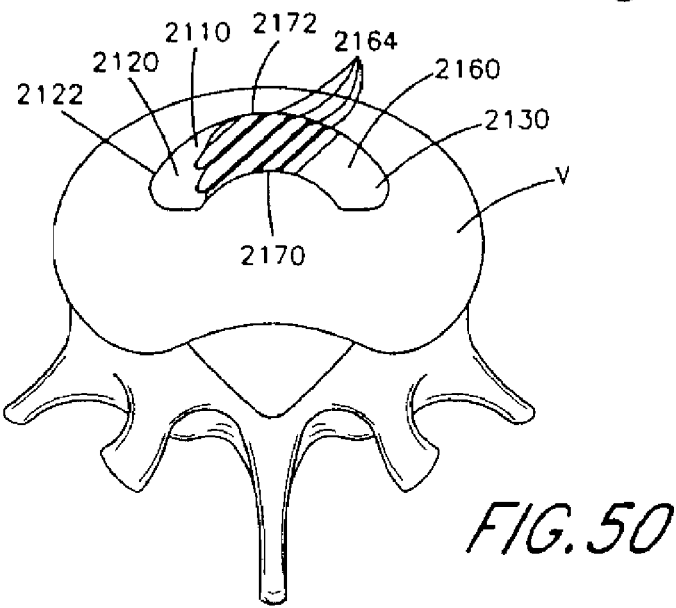
FIG. 50 is a view showing the spinal implant of FIG. 43 between adjacent vertebrae.

Another embodiment of a fusion device or spinal implant 2110 is illustrated in FIGS. 43-47. The spinal implant 2110 is substantially similar to the embodiment disclosed in FIGS. 38-42. The implant 2110 is placed between the adjacent vertebrae V to provide sufficient support to allow fusion of the adjacent vertebrae, as shown in FIG. 50. The spinal implant 2110 is preferably made from an allograft material, though the materials described above in connection with the spinal implant 2010 may also be used. Also, as with the implant 2010, the implant 2110 may be formed as a cage or other suitable configuration.

Figure 65:
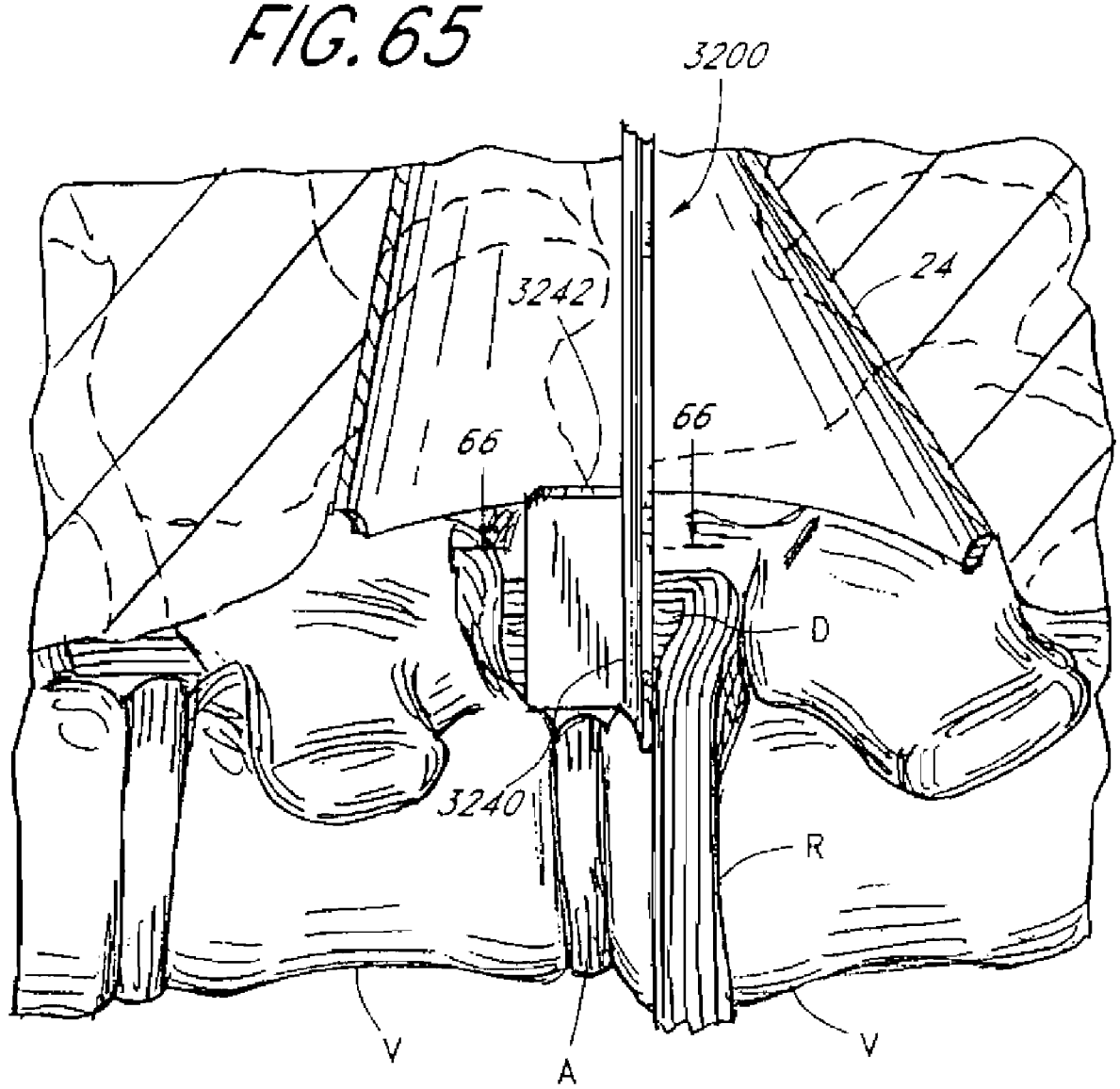
FIG. 65 is a sectional view, similar to FIG. 57, of the apparatus of FIG. 63, used in conjunction with additional structure in a patient.

The spinal implant 2110 (FIGS. 43-47) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 43-44) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 43 and 46) is defined by an upper surface 2140 and a lower surface 2142 extending generally parallel to the upper surface 2140. The recess 2138 (FIG. 44) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 can grip the implant 2110 for inserting the implant between the adjacent vertebrae V.

Figures 43, 44:
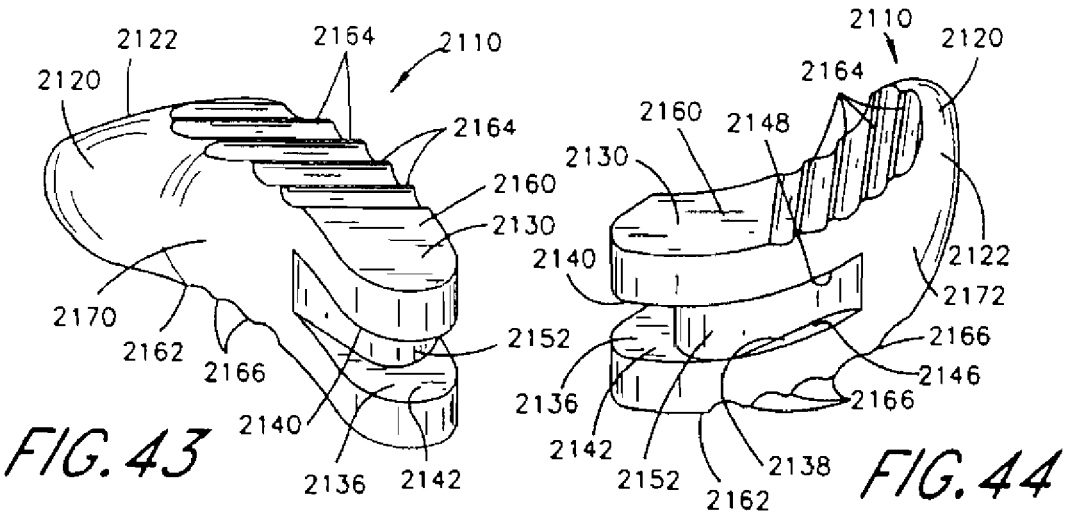
FIG. 43 is a perspective view of another embodiment of a spinal implant constructed according to another embodiment showing a first side surface of the spinal implant.
FIG. 44 is a perspective view of the spinal implant of FIG. 43 showing a second side surface of the spinal implant.
Figure 45:
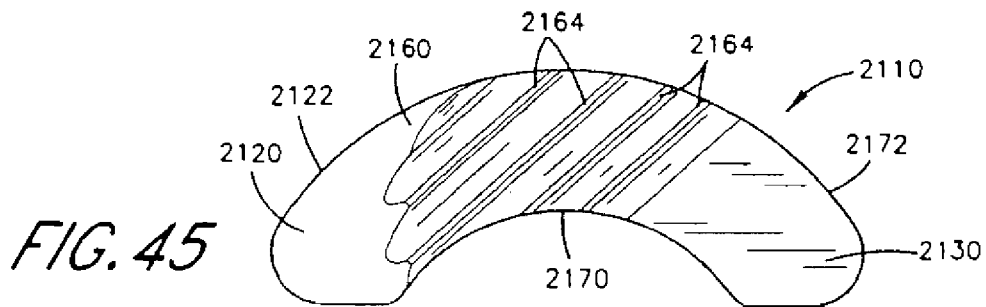
FIG. 45 is a plan view of the spinal implant of FIG. 43 showing an upper surface of the spinal implant.
Figure 46:
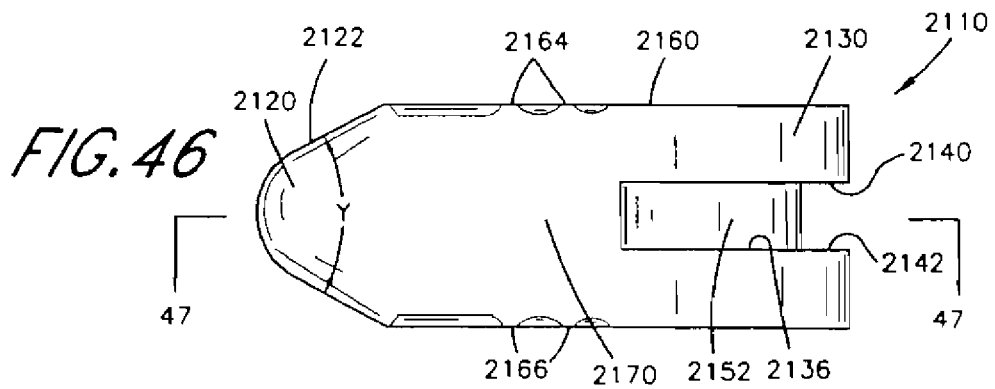
FIG. 46 is a side view of the spinal implant of FIG. 43 showing the first side surface.
Figure 47:
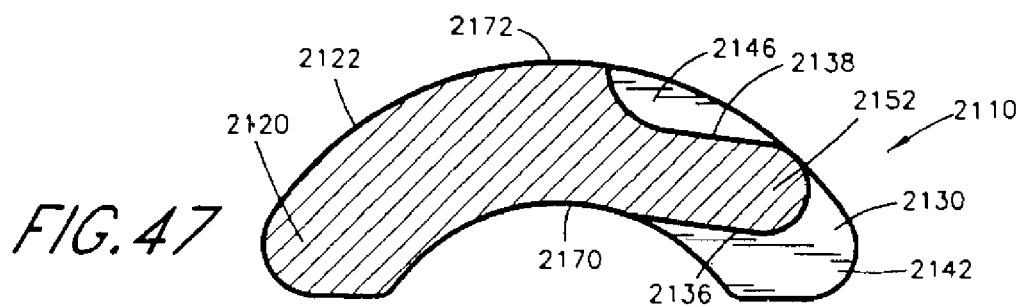
FIG. 47 is a cross-sectional view of the spinal implant taken along the line 47-47 in FIG. 46.

As viewed in FIGS. 43-46, the implant 2110 has an upper surface 2160 for engaging the upper vertebra V. The implant 2110 has a lower surface 2162, as viewed in FIGS. 43-46, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG. 44 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 preferably is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that in some embodiments more than one implant 2110 may be inserted between the vertebrae.

The apparatus or shield 3100 for use in placing the fusion devices or spinal implants between the vertebrae is illustrated in FIGS. 52-56. The apparatus 3100 preferably includes an elongated body portion 3102, which protects the nerve root or dura, and a mounting portion 3104, which allows for the surgeon to releasably mount the apparatus 3100 to the access device 20. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, for example, stainless steel. In the illustrated embodiment, apparatus 3100 is manufactured from stainless steel having a thickness of about 0.02 inches to about 0.036 inches. The elongated body portion 3102 has dimensions that correspond to the depth in the body in which the procedure is being performed, and to the size of the body structure that is to be shielded by elongated body portion 3102. In one embodiment, the elongated body portion 3102 has a width 3106 of about 0.346 inches and a length of about 5.06 inches (FIG. 53), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 preferably allows the apparatus 3100 to be secured to a support structure in any number of ways. In one embodiment, mounting portion 3104 may include a ring portion. With reference to FIGS. 52-56, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the illustrated embodiment, the mounting portion 3104 has a substantially cylindrical configuration in order to be mounted within the interior lumen of the access device 20, as will be described below. The ring portion 3104 has an exterior dimension 3130 of about 0.79 inches, and an interior dimension 3132 of about 0.76 inches. It is understood that the dimensions of the ring portion 3104 can be different, such as, for example, where the access device 20 has a different interior dimension. Moreover, the cylindrical shape of the ring portion 3104 can change, such as, for example, where the apparatus 3100 is used with a support member having a differently shaped internal lumen.

Finger grip portions 3122 preferably extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the access device 20.

The elongated body portion 3102 and the mounting portion 3104 may be manufactured from a single component, such as a sheet of stainless steel, and the mounting portion 3104 may be subsequently formed into a substantially cylindrical shape. In another embodiment, the mounting portion 3104 may be manufactured as a separate component and coupled to the elongated body portion, by techniques such as, for example, welding and/or securement by fasteners, such as rivets.

The access device 20 serves as a stable mounting structure for apparatus 3100. In particular, mounting portion 3104 is releasably mounted to the interior wall of proximal wall portion 22 of access device 20. Elongated body portion 3102 extends distally into the operative site to protect the desired body structure, such as the nerve, as will be described below.

Figure 58:
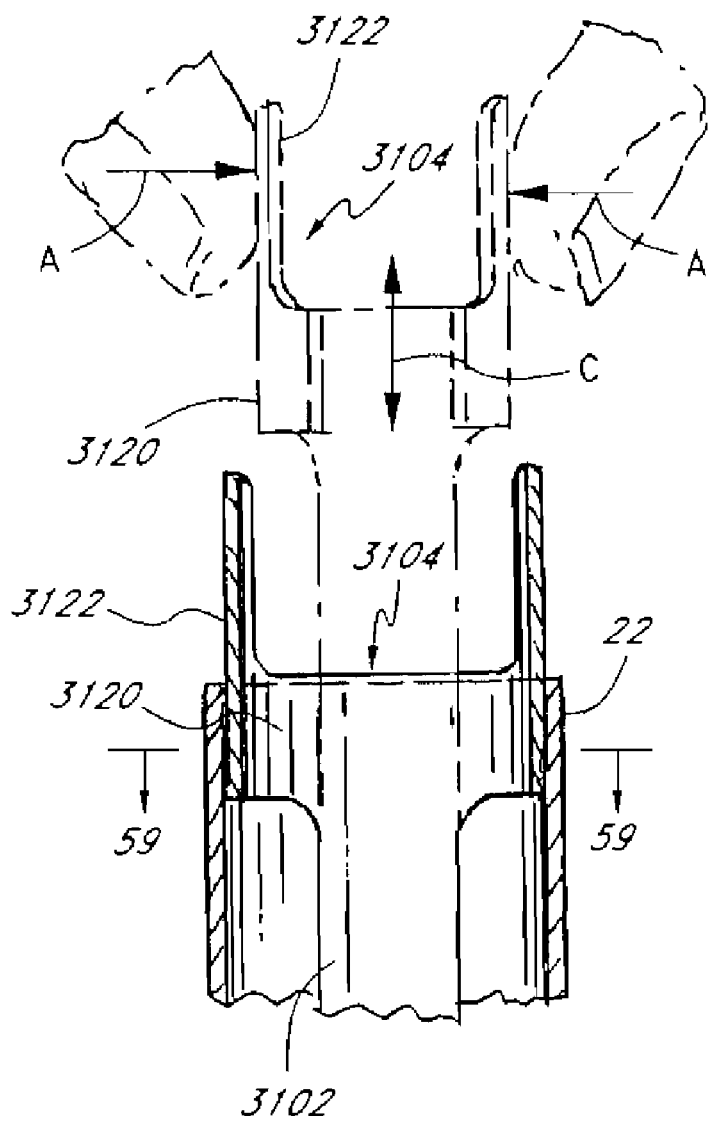
FIG. 58 is a longitudinal sectional view of the apparatus of FIG. 57 taken from line 58-58 of FIG. 57.
Figure 59:
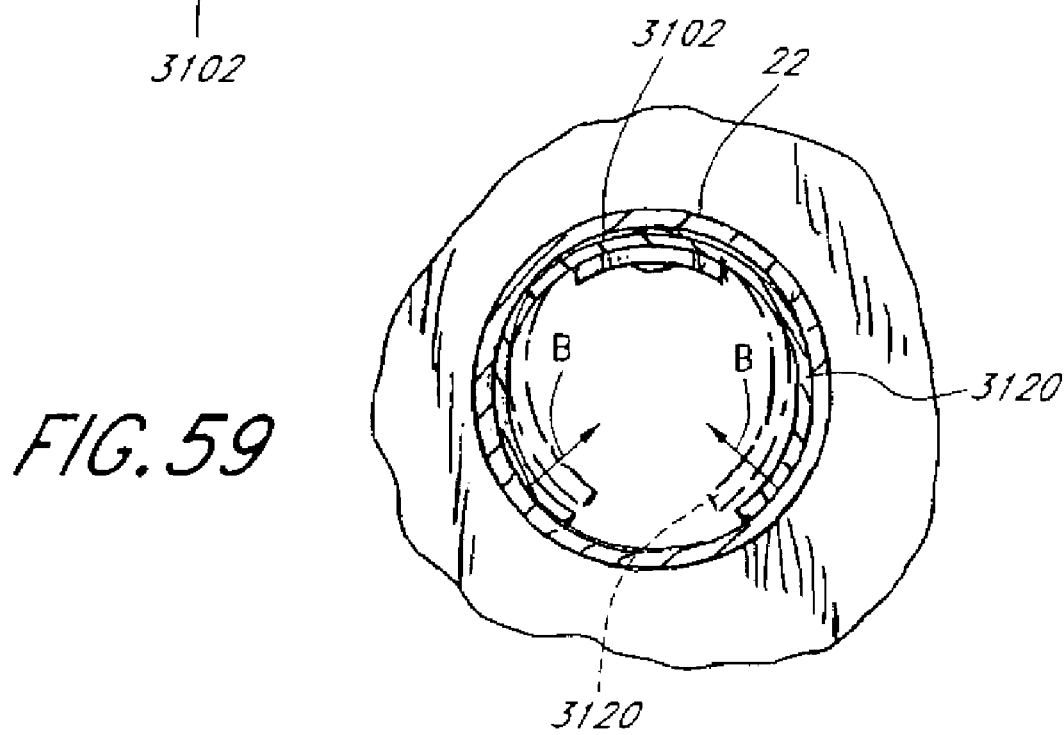
FIG. 59 is a transverse sectional view of the apparatus of FIG. 58 taken from line 59-59 of FIG. 58.

To install the apparatus 3100 within the interior passage of the proximal wall portion 22, the surgeon may apply an inwardly directed force on the ring portion 3120, thereby causing the ring portion to resiliently deform, as illustrated by dashed line and arrows B in FIG. 59. The surgeon subsequently inserts the apparatus 3100 into the interior lumen of the proximal wall portion 22 (as indicated by arrow C) to the position of ring portion 3104 illustrated in solid line in FIG. 58. When the surgeon releases the finger grip portions 3122, the ring portion 3120 resiliently moves towards its undeflected configuration, thereby engaging the interior lumen of the proximal wall portion 22. Advantages of some embodiments include that the mounting portion 3104 is easily removed and/or moved with respect to the access device 20 without disturbing the position of the access device 20 or any other instrumentation.

Figure 57:
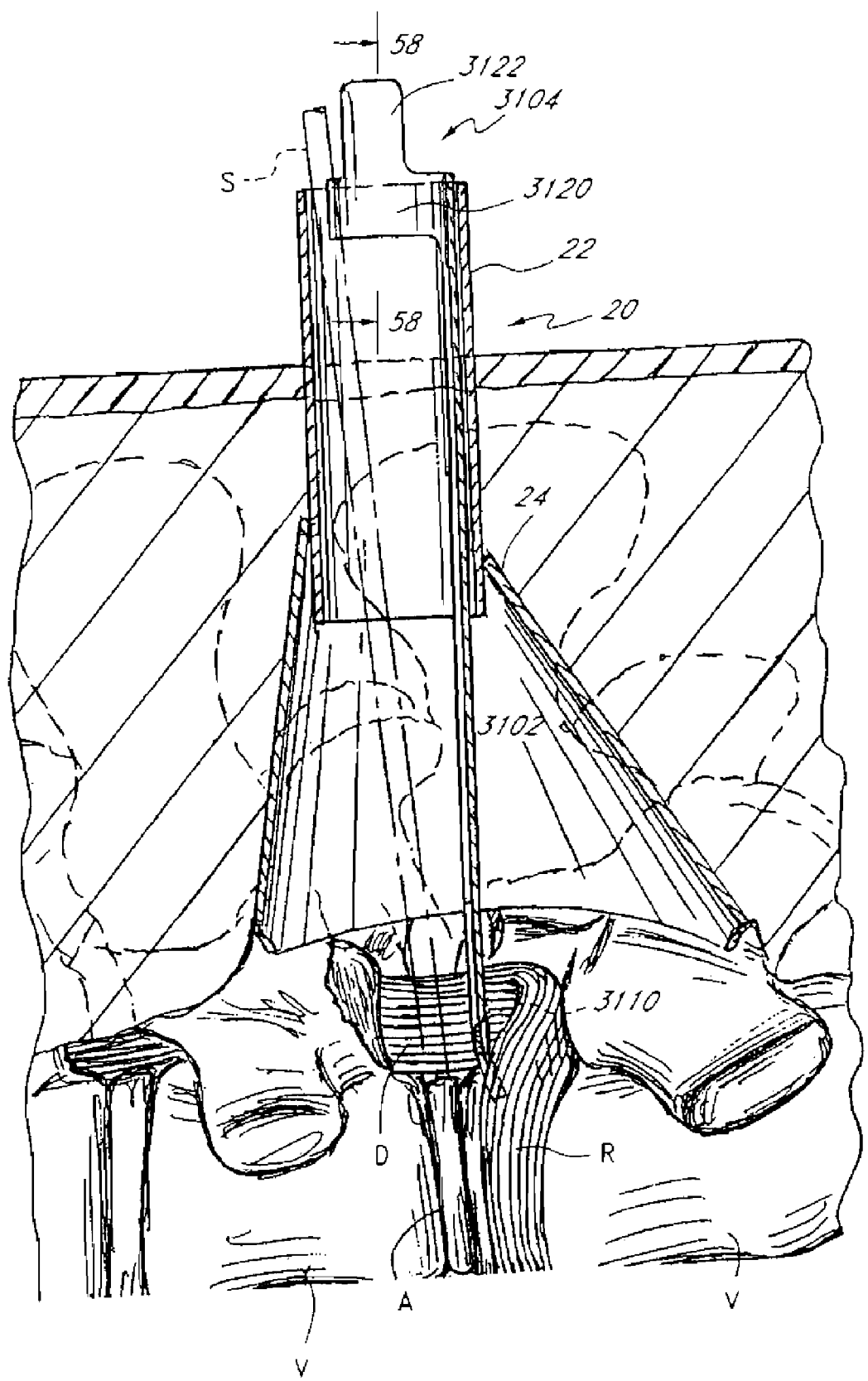
FIG. 57 is a sectional view of the apparatus of FIG. 52, used in conjunction with additional structure in a patient.

As illustrated in FIG. 57, the configuration of the mounting portion 3104 and the elongated body portion 3102 allow the elongated body portion to occupy a small space along the periphery of the proximal wall portion 3122. This allows the apparatus to protect the desired body structure without blocking access for the insertion of other surgical instrumentation, and without blocking visibility by the surgeon during the procedure.

The mounting portion 3104 is one configuration for mounting the apparatus 3100 to the support structure. It is contemplated that the apparatus 3100 may be mounted within the access device 20 in any suitable manner.

When in position, the distal end portion 3110 covers the exiting nerve root R, while exposing the disc annulus A (See FIG. 57). As discussed above, the debridement and decortication of tissue covering the vertebrae, as well as a facetectomy and/or laminectomy if indicated, are preferably performed prior to the insertion of apparatus 3100 into the surgical space. Accordingly, in some embodiments, there is no need to displace or retract tissue, and apparatus 3100 merely covers the nerve root and does not substantially displace the nerve root or any other body tissue. It is understood that the term "cover" as used herein refers to apparatus 3100 being adjacent to the body structure, or in contact with the body structure without applying significant tension or displacement force to the body structure.

Additional surgical instrumentation S may be inserted into the access device to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 60:
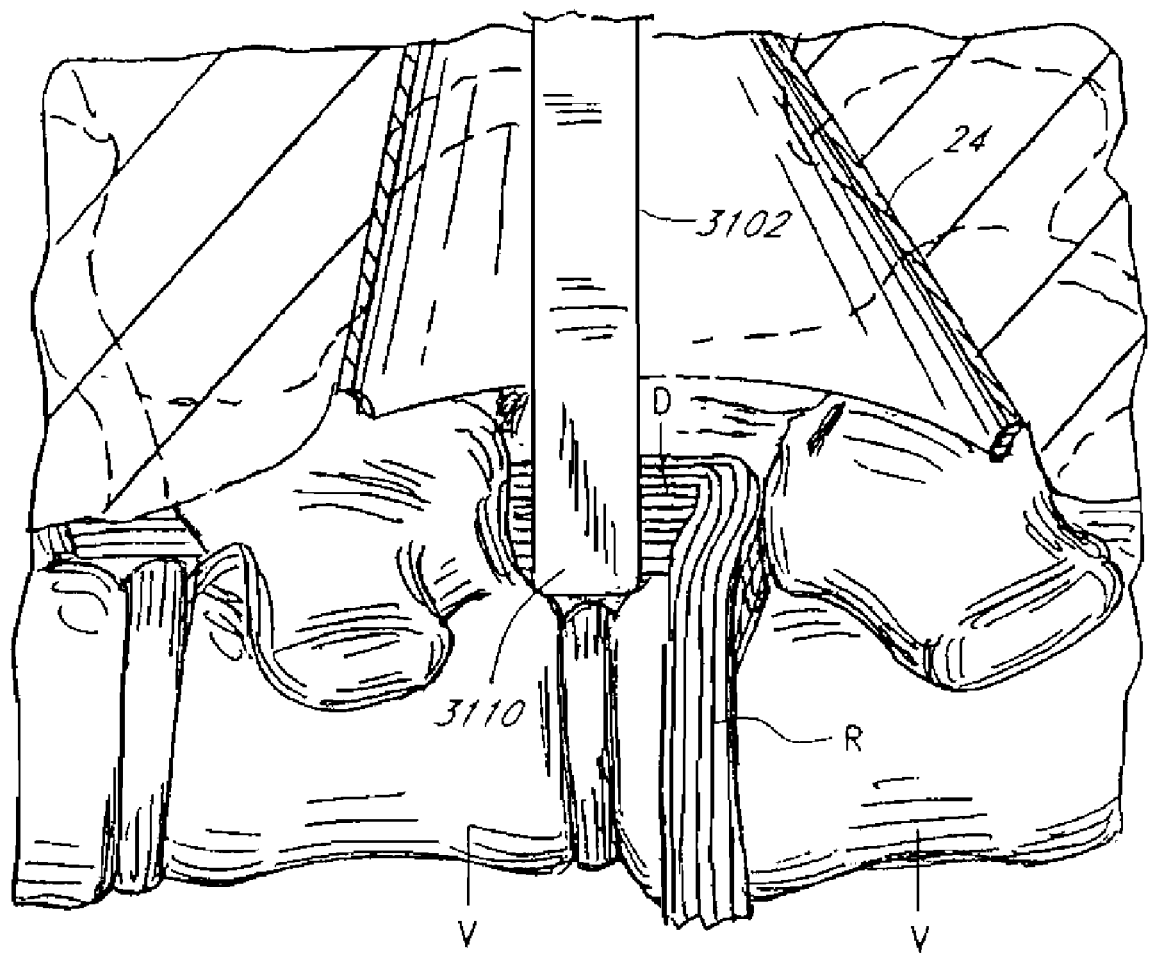
FIG. 60 is a sectional view, similar to FIG. 57, illustrating an alternative position of the apparatus of FIG. 52.

As illustrated in FIG. 60, the elongated body portion 3102 preferably is rotated to protect the spinal cord, or dura D, during the above procedures. The surgeon may change the position of the apparatus 3100 by approximating the finger grips 3122 to release the ring portion from engagement with the inner wall of the proximal wall portion 20, and then re-position the apparatus 3100 without disturbing the access device 20 (as shown in FIG. 58).

Figure 61:
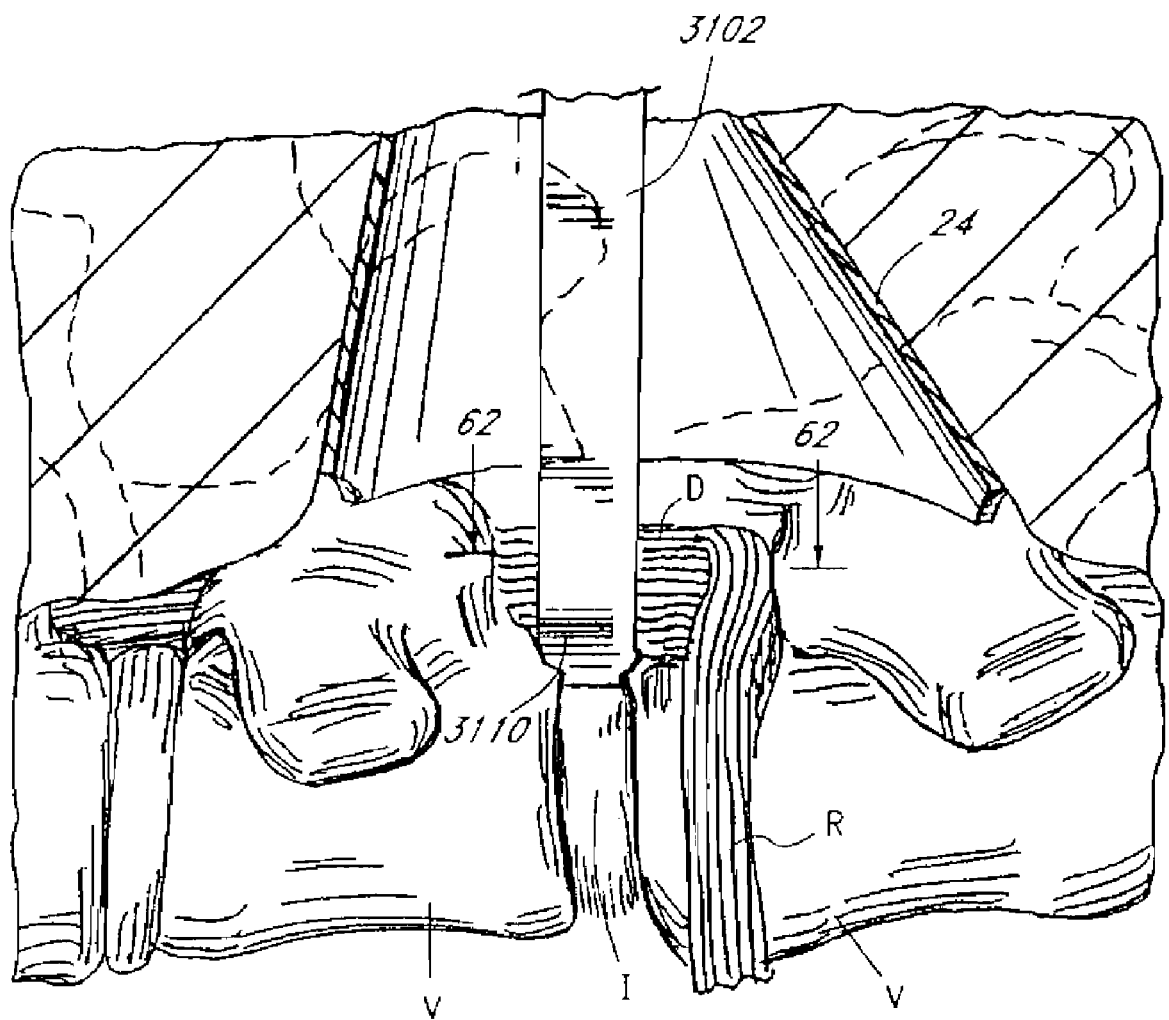
FIG. 61 is a sectional view, similar to FIG. 57, illustrating another alternative position of the apparatus of FIG. 52.
Figure 62:
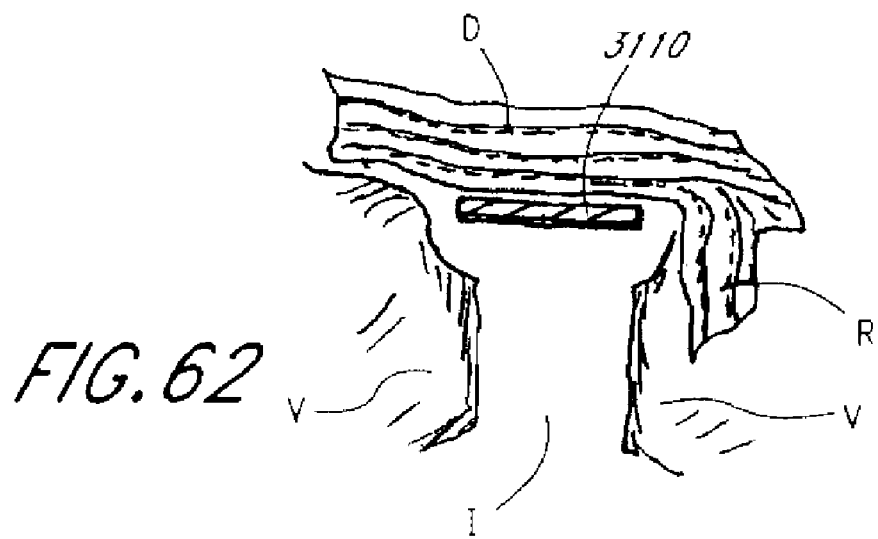
FIG. 62 is a transverse sectional view of the apparatus of FIG. 61, taken along lines 62-62 of FIG. 61.

During certain surgical procedures, it may be useful to introduce crushed bone fragments or the fusion devices 2010 or 2110 to promote bone fusion. As illustrated in FIGS. 61-62, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Figure 63:
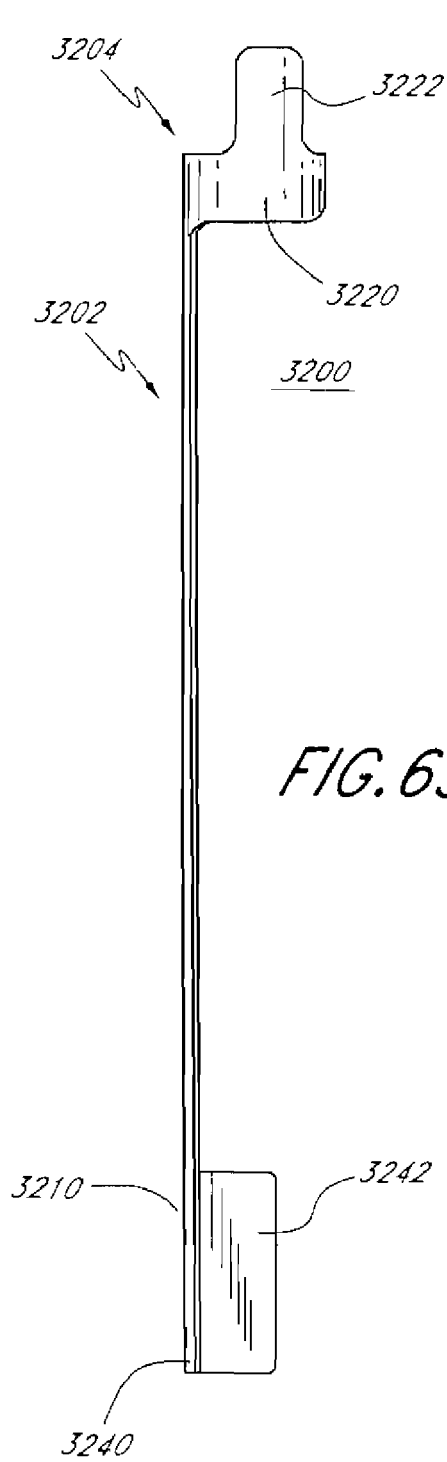
FIG. 63 is a side view, similar to FIG. 52, of another apparatus.
Figure 64:
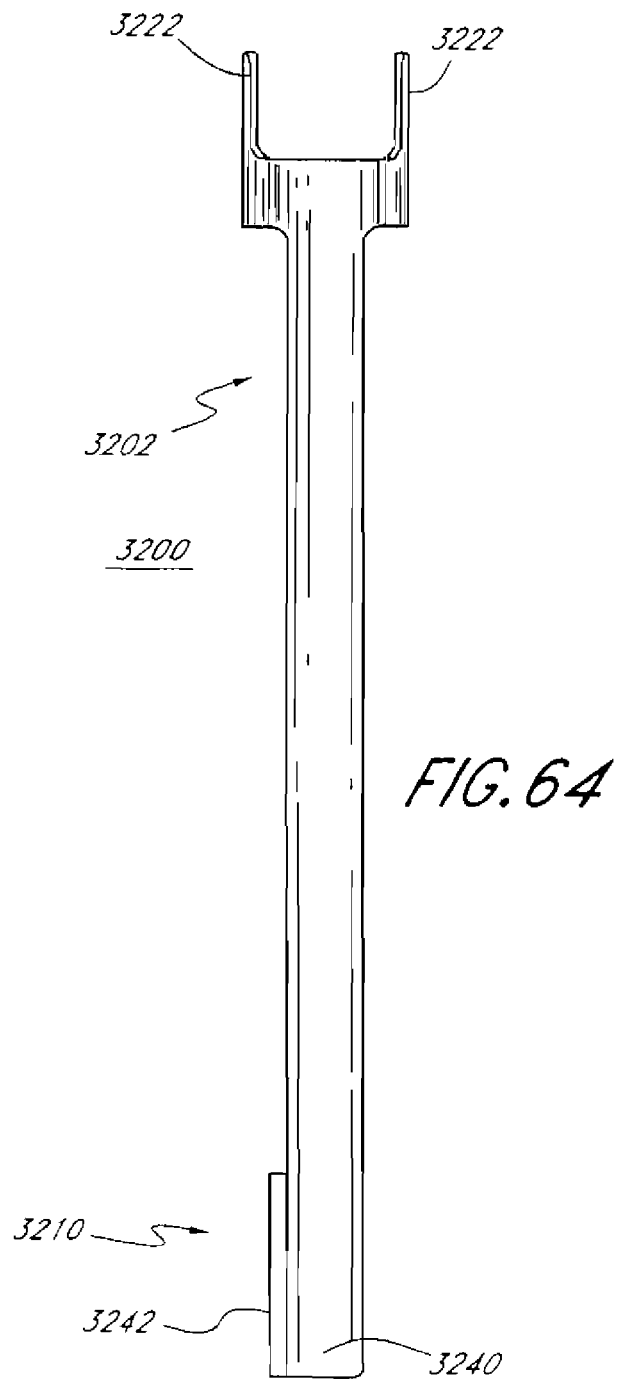
FIG. 64 is a front view, similar to FIG. 55, of the embodiment of FIG. 63.

Another embodiment of the apparatus or shield is illustrated in FIGS. 63-64, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In one embodiment, surfaces 3240 and 3242 defined an angle of about 90 degrees between them. Alternatively another angle between surfaces 3240 and 3242 may be defined as indicated by the body structures to be protected.

Figure 66:
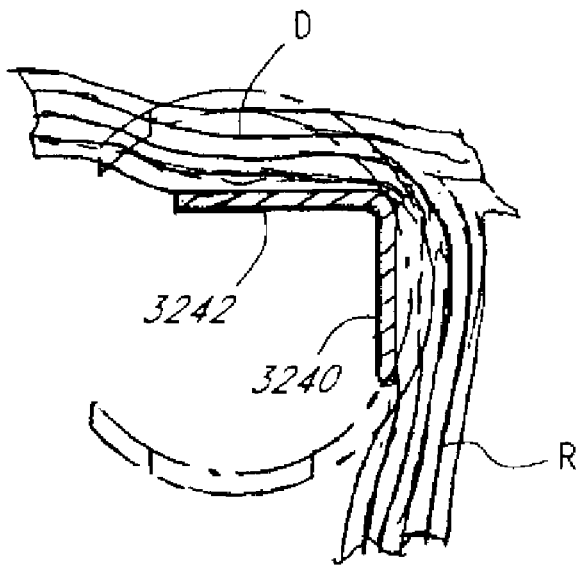
FIG. 66 is a transverse sectional view of the apparatus of FIG. 63, taken along lines 66-66 of FIG. 65.

Distal end portion 3210 allows the apparatus to provide simultaneous shielding of both the dura D and the nerve root R. In FIGS. 65-66, surface 3242 shields the dura D, and surface 3240 shields the nerve root R. It is understood that surfaces 3240 and 3242 may be interchanged with respect to which tissue they protect during the surgical procedure.

According to one technique, once the fusion and fixation portions of the procedure have been performed, the procedure is substantially complete. The surgical instrumentation, such as the endoscope 500 can be withdrawn from the surgical site. The access device 20 is also withdrawn from the site. The muscle and fascia typically close as the access device 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Surgical Procedures that may be Performed with the Systems Described Herein

As discussed above, the systems disclosed herein can be used to access a surgical location at or near the spine of a patient to enable procedures on the spine. These procedures can be applied to one or more vertebral levels, as discussed above. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described herein. These procedures may be performed primarily through retractors or other similar access devices, such as those discussed herein. The procedures may be partially performed percutaneously, e.g., over a guidewire or other structure that has a smaller profile than the access devices describe herein. By performing at least a portion of the procedures percutaneously, the amount of time that a retractor or similar access device is deployed or expanded may be reduced. Also, percutaneous techniques described herein increase the ability of the surgeon to quickly and easily deliver place markers, fasteners, and other implants to target sites, to prepare target sites, and to complete procedures. Percutaneous techniques enable the performance of a substantial portion of a spinal procedure with little or no visualization of the location where the procedure is performed.

A. Procedures Involving Anterior Lumbar Interbody Fusion

The access devices and systems described herein are amenable to a variety of procedures that may be combined with an anterior lumbar interbody fusion (referred to herein as an "ALIF").

In one embodiment of a first method, three adjacent vertebrae, such as the L4, the L5, and the S1 vertebrae of the spine, are treated by first performing an ALIF procedure. Such a procedure may be performed in a conventional manner. The ALIF involves exposing a portion of the spine, in particular the vertebrae and discs located in the interbody spaces, i.e., the spaces between adjacent vertebrae. Any suitable technique for exposing the interbody spaces may be employed, e.g., an open, mini-open, or minimally invasive procedure. In one embodiment, the interbody spaces between the L4, L5, and S1 vertebrae are exposed to the surgeon. Once exposed, the surgeon may prepare the interbody space, if needed, in any suitable manner. For example, some or all of the disc may be removed from the interbody space and the height of the interbody space may be increased or decreased. The interbody space between the L4 and the L5 vertebrae may be exposed separately from the interbody space between the L5 and S1 vertebrae or they may be generally simultaneously exposed and prepared.

After the interbody space has been exposed and prepared, a suitable fusion procedure may be performed. For example, in one example fusion procedure, one or more fusion devices may be placed in the interbody space. Any suitable fusion device may be used, e.g., a fusion cage, a femoral ring, or another suitable implant. Various embodiments of implants and techniques and tools for the insertion of implants are described in U.S. application Ser. No. 10/280,489, filed Oct. 25, 2002, which has been published as Publication No. 2003/0073998 on Apr. 17, 2003, which is hereby incorporated by reference herein in its entirety. In one variation, one or more fusion cages may be placed in an interbody space, e.g., between the L4 and L5 vertebrae, between the L5 and S1 vertebrae, or between the L4 and L5 vertebrae and between the L5 and S1 vertebrae. In another variation, one or more femoral rings may be substituted for one or more of the fusion cages and placed between the L4 and L5 vertebrae and/or between the L5 and S1 vertebrae. In another variation, one or more fusion devices are combined with a bone growth substance, e.g., bone chips, to enhance bone growth in the interbody space(s).

After anterior placement of the fusion device, an access device is inserted into the patient to provide access to a spinal location, as described above. A variety of anatomical approaches may be used to provide access to a spinal location using the access device 20. The access device preferably is inserted generally posteriorly. As used herein the phrase "generally posteriorly" is used in its ordinary sense and is a broad term that refers to a variety of surgical approaches to the spine that may be provided from the posterior side, i.e., the back, of the patient, and includes, but is not limited to, posterior, postero-lateral, retroperitoneal, and transforaminal approaches. Any of the access devices described or incorporated herein, such as the access device 20, could be used.

The distal end of the access device may be placed at the desired surgical location, e.g., adjacent the spine of the patient with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device. In other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the adjacent vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae above and below the first vertebra.

When it is desired to treat the L4, L5, and S1 vertebrae, the access device may be inserted over the L5 vertebrae and then expanded to provide increased access to the L4 and S1 vertebrae. In one embodiment, the access device can be expanded to an oblong shaped configuration wherein the access device provides a first dimension of about 63 mm, and a second dimension perpendicular to the first dimension of about 24 mm. In another embodiment, the access device can be expanded to provide a first dimension of about 63 mm, and a second dimension perpendicular to the first dimension of about 27 mm. These dimensions provide a surgical space that is large enough to provide access to at least three adjacent vertebrae without exposing excessive amounts of adjacent tissue that is not required to be exposed for the procedures being performed. Other dimensions and configurations are possible that would provide the needed access for procedures involving three adjacent vertebrae.

When the access device is in the second configuration, fixation of the three vertebrae may be performed. As discussed above, fixation is a procedure that involves providing a generally rigid connection between at least two vertebrae. Any of the fixation procedures discussed above could be used in this method, as could other fixation procedures. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by the elongated member 650. The three fasteners 600a, 600b, and 600c and the elongate member 650 comprise a first fixation assembly. A second fixation assembly may be applied to the patient on the opposite side of the spine, i.e., about the same location on the opposite side of the medial line of the spine. Other fixation procedures could be applied, e.g., including two fasteners that coupled to the L4 and the S1 vertebrae and an elongate member interconnecting these vertebrae.

One variation of the first method provides one level of fixation on the anterior side of the patient, e.g., when the fusion device is placed in the interbody space. For example, fixation of the L5 and S1 vertebrae could be provided on the anterior side of the spine, in addition to the other procedures set forth above (e.g., a two level postero-lateral fixation). Also, fixation of the L4 and L5 vertebrae could be provided on the anterior side of the spine, in addition to the other procedures set forth above (e.g., a two level postero-lateral fixation).

In a second method, substantially the same steps as set forth above in connection with the first method would be performed. In addition, after the access device is inserted, a decompression procedure is performed through the access device. A decompression procedure is one where unwanted bone is removed from one or more vertebrae. Unwanted bone can include stenotic bone growth, which can cause impingement on the existing nerve roots or spinal cord. Decompression procedures that may be performed include laminectomy, which is the removal of a portion of a lamina(e), and facetectomy, which is the removal of a portion of one or more facets. In one variation of this method, decompression includes both a facetectomy and a laminectomy. Any suitable tool may be used to perform decompression. One tool that is particularly useful is a kerrison.

In a third method, substantially the same steps as set forth above in connection with the first method would be performed. That is, an ALIF procedure is performed in combination with a fixation procedure. In addition, a fusion procedure may be performed through the access device which may have been placed generally posteriorly, e.g., postero-laterally, tranforaminally or posteriorly, whereby bone growth is promoted between the vertebrae and the fixation assembly, including at least one of the fasteners 600a, 600b, 600c and/or the elongate element 650. This procedure is also referred to herein as an "external fusion" procedure.

One example of an external fusion procedure that may be performed involves placement of a substance through the access device intended to encourage bone growth in and around the fixation assembly. Thus, fusion may be enhanced by placing a bone growth substance adjacent any of the fasteners 600a, 600b, 600c and/or the elongate member 650. The bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance can cause bone to bridge across from the vertebra(e) to one or more components of the fixation assembly.

In a fourth method, substantially the same steps as set forth above in connection with the second method would be performed. That is, an ALIF procedure is performed anteriorly, and a decompression procedure and a fixation procedure are performed through the access device which may be placed generally posteriorly, e.g., postero-laterally, tranforaminally, or posteriorly. In addition, bone growth substance is placed in and around a fixation assembly through the access device, as discussed above in connection with the third method. The bone growth substance encourages bone to bridge across from the vertebrae to the fixation assembly.

In a fifth method, an ALIF procedure is performed, as discussed above in connection with the second method. After one or more fusion devices is placed in the interbody space, access is provided by way of the access device, as discussed above, from any suitable anatomical approach, e.g., a generally posterior approach. Preferably, a postero-lateral approach is provided. After access has been provided, a bone growth substance, such as those discussed above in connection with the third method, is delivered through the access device. The bone growth substance is placed adjacent an interbody space, e.g., the space between the L4 and the L5 vertebrae and/or between the L5 and the S1 vertebrae. The bone growth substance encourages fusion of the adjacent vertebrae, e.g., L4 to L5 and/or L5 to S1, by stimulating or enhancing the growth of bone between adjacent vertebrae, as discussed above.

In a sixth method, substantially the same steps described in connection with the first method are performed, except that the fixation procedure is optional. In one variation of the sixth method, the fixation procedure is not performed. However, after the access device is inserted, a bone growth substance is placed in and around one or more interbody spaces through the access device. Where the sixth method involves a two level procedure, the bone growth substance can be placed adjacent the interbody space between the L4 and the L5 vertebra and/or between the L5 and the S1 vertebra. Thus, bone growth may occur in the interbody space and adjacent the interbody space between the vertebrae.

The foregoing discussion illustrates that an ALIF procedure can be combined with a variety of procedures that can be performed through an access device disclosed herein. In addition, though not expressly set forth herein, any combination of the procedures discussed above, and any other suitable known procedure, may also be combined and performed through the access devices described herein, as should be understood by one skilled in the art.

B. Spine Procedures Providing Minimally Invasive Lumbar Interbody Fusion

Another category of procedures that may be performed with the access devices and systems described above involves a minimally invasive lumbar interbody fusion (referred to herein as a "MILIF"). MILIF procedures are particularly advantageous because they permit the surgeon to perform a wide variety of therapeutic procedures without requiring fusion by way of an anterior approach, as is required in an ALIF. This provides a first advantage of allowing the surgeon to perform all procedures from the same side of the patient and also possibly from the same approach. Also, the access devices and systems disclosed herein provide the further advantage of enabling two level procedures, and many other related procedures, to be performed by way of a single percutaneous access. These and other advantages are explained more fully below.

In a first MILIF method, a two level postero-lateral fixation of the spine involving three adjacent vertebrae, such as the L4, L5, and S1 vertebrae, is provided. Analogous one level procedures and two level procedures involving any other three vertebrae also may be provided. In addition, the access devices and systems described herein could be used or modified to accommodate other multi-level procedures, such as a three level procedure. The surgeon inserts an access device such as described herein to a surgical location near the spine. As discussed above, the access devices are capable of a wide variety of anatomical approaches. In this procedure, a postero-lateral approach is preferred. Once the access device is inserted to a location adjacent the spine, as discussed above, it may be configured, e.g., expanded, as discussed above, to a configuration wherein sufficient access is provided to the surgical location.

Any suitable fusion process may then be performed. For example, an implant may be advanced through the access device into the interbody space in order to maintain disc height and allow bone growth therein, e.g., as in a fusion procedure. In order to ease insertion of the implant, it may be beneficial to prepare the interbody space. Interbody space preparation may involve removal of tissue or adjusting the height of the interbody space through the access device, such as in a distraction procedure. Once the interbody space is prepared, a suitable implant may be advanced through the access device into the interbody space, taking care to protect surrounding tissues. Various embodiments of implants and techniques and tools for their insertion are described in U.S. application Ser. No. 10/280,489, incorporated by reference hereinabove. In general, the implant preferably is an allograft strut that is configured to maintain disc height and allow bone growth in the interbody space.

In addition to providing a suitable fusion, the first method provides fixation of the vertebrae. The fixation procedure may take any suitable form, e.g., any of the fixation procedures similar to those disclosed above. In particular, when the access device is in the expanded or enlarged configuration, fixation of the three adjacent vertebrae may be performed. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by way of the elongated member 650. As discussed above, a second fixation assembly may be applied to the patient on the opposite side of the spine, e.g., about the same location on the opposite side of the medial line of the spine.

In a second MILIF method, substantially the same procedures set forth above in connection with the first MILIF method are performed. In addition, a suitable decompression procedure may be performed, as needed. As discussed above, decompression involves removal of unwanted bone by way of a suitable decompression technique that may be performed through the access device. In one embodiment, decompression is performed through the access device after the access device has been expanded. As discussed above, suitable decompression techniques include a laminectomy, a facetectomy, or any other similar procedure. Decompression for the L4, the L5, and/or the S1 vertebrae may be needed and can be performed through the access devices described herein without requiring the access device to be moved from one position to another.

In a third MILIF method, substantially the same procedures set forth above in connection with the first MILIF method are performed. In addition, a further fusion procedure, e.g., a fusion procedure external to the interbody space, is provided. The external fusion procedure is performed adjacent to the interbody space wherein bone growth may be promoted in the proximity of the fixation assembly, e.g., above the postero-lateral boney elements of the spine, such as the facet joints and the transverse processes. In one embodiment, when the fixation assembly comprising the fasteners 600a, 600b, 600c and/or the elongate element 650 has been applied to three adjacent vertebrae, a substance is applied through the access device to one or more components of the fixation assembly to maintain or enhance the formation and/or growth of bone in the proximity of the fixation assembly.

For example, a bone growth substance may be placed adjacent any of the fasteners 600a, 600b, 600c and/or the elongate member 650. Bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance advantageously causes bone to grow between the vertebrae and the fixation assembly to form a bridge therebetween.

A fourth MILIF method involves substantially the same procedures performed in connection with the third MILIF method. In particular, one or more implants are positioned in the interbody spaces through an access device, a fixation procedure is performed through the access device, and a further fusion procedure is performed wherein bone growth substance is positioned adjacent the interbody space through the access device. In addition, a decompression procedure is performed through the access device that may include a facetectomy and/or a laminectomy.

A fifth MILIF method involves substantially the same procedures performed in connection with the first MILIF method, except that the fixation is optional. In one embodiment, the fixation is not performed. In addition, a further fusion procedure is performed through the access device wherein bone growth substance is positioned adjacent the interbody space, as discussed above.

A sixth MILIF method is substantially the same as the fifth MILIF method, except that a further fusion procedure is performed through the access device. In particular, an implant is positioned in the interbody space through an access device, a decompression procedure is performed through the access device, and a further fusion procedure is performed whereby bone growth substance is placed adjacent the interbody space through the access device. As discussed above, the decompression procedure may include a facetectomy, a laminectomy, and any other suitable procedure. As with any of the methods described herein, the procedures that make up the sixth MILIF method may be performed in any suitable order. Preferably the decompression procedure is performed before the external fusion procedure.

The foregoing discussion illustrates that a MILIF procedure can include a variety of procedures that can be performed through an access device described herein. In addition, though not expressly set forth herein, any combination of the procedures discussed above, and any other suitable known procedures, may also be combined, as should be understood by one skilled in the art.

C. Other Multi-Level Procedures

While the foregoing procedures have involved interbody fusion, the access devices and systems described herein can be employed in a variety of single level and multi-level procedures (e.g., more than two levels) that do not involve an interbody fusion. For example, a discectomy can be performed through the access devices described herein without implanting an interbody fusion device thereafter, e.g., to remove a hemeation. In another embodiment, a discectomy can be performed in more than one interbody space without inserting an interbody fusion device into each interbody space, e.g., to remove multiple herneations. In another embodiment, a single or multi-level decompression procedure can be performed to remove unwanted bone growth.

It will be understood that the foregoing is only illustrative of the principles of the invention, and that various modifications, alterations, and combinations can be made by those skilled in the art without departing from the scope and spirit of the invention. Some additional features and embodiments are described below.

III. Apparatuses and Methods Combining Percutaneous and Minimally Invasive Access Certain of the procedures described above can be performed in part percutaneously and in part minimally invasively, e.g., through an access device. FIGS. 67-70 illustrate a first technique wherein at least a portion of a procedure is performed percutaneously.

Figure 67:
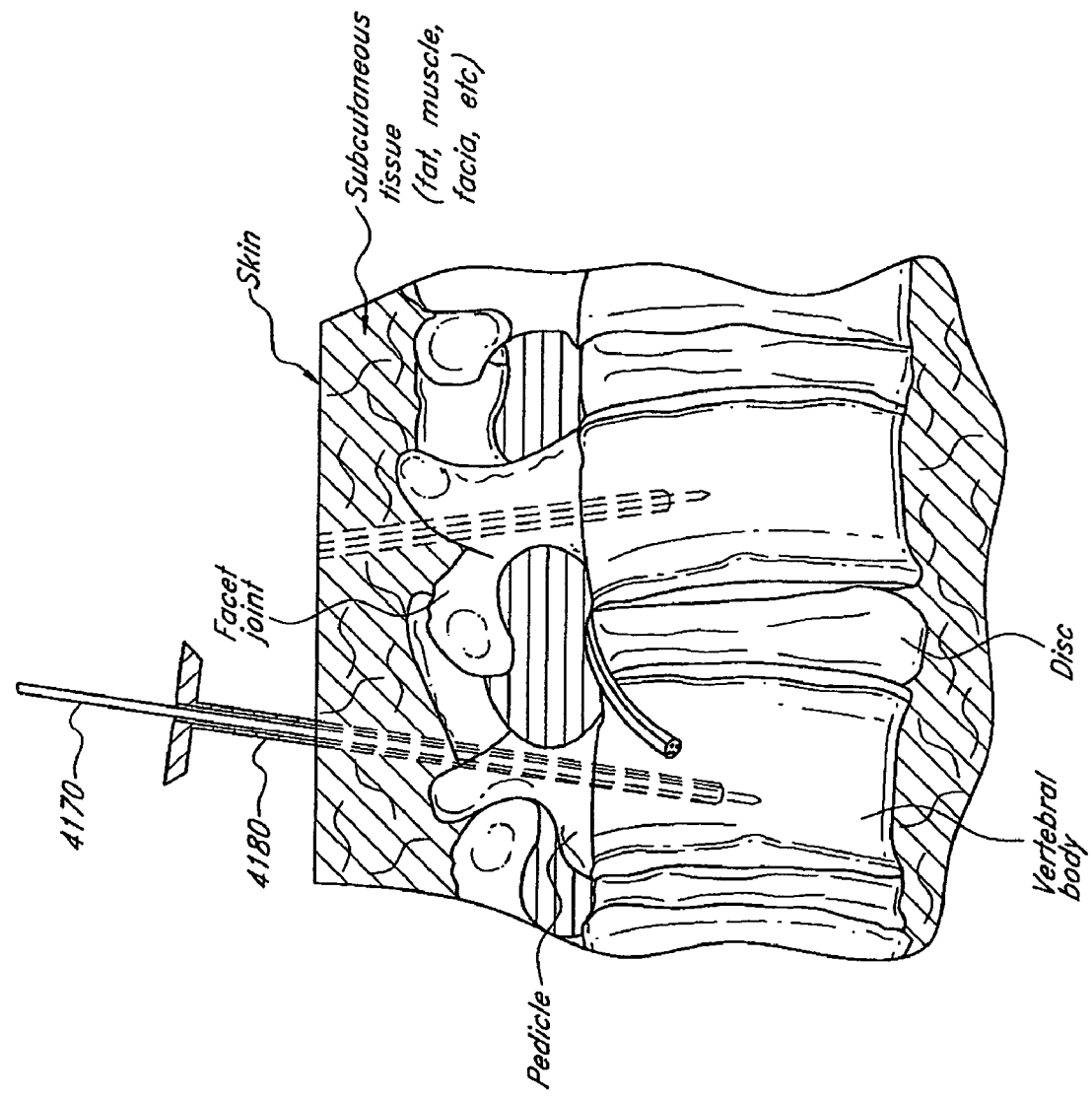
FIG. 67 is a schematic illustration of a method for preparing a site of a vertebra percutaneously to receive an implant.

FIG. 67 shows two adjacent pedicles from a lateral perspective and illustrates an early stage of the first technique. Prior to the stage illustrated in FIG. 67, a device that includes a hollow structure is used to form a percutaneous entry or path between the skin and a vertebral surface or a vertebral target site. A vertebral target site is any site on a vertebra at which a procedure or a portion of a procedure is to be performed. For example, as discussed below, some procedures may advantageously be performed at a pedicle of a vertebra or at a region between a facet joint and a transverse process of a vertebra. In one technique the hollow structure of the percutaneous entry forming device is configured to receive a sharp implement, which is configured to cut and separate tissue. As tissue is cut and separated, the percutaneous access path is formed between the skin and the vertebral surface.

One device that may be used at an early stage of formation of a percutaneous access path combines a trocar and a needle 4180, such as a Jamshidi needle. The percutaneous access path is sometimes referred to herein as a tissue tunnel. In one technique, the trocar is inserted into the needle 4180 and the trocar and needle are advanced together through the skin at a skin puncture location and through subcutaneous tissue (e.g., through fat, muscle, and fascia) until a distal end of the trocar and needle are at the vertebral target site. The needle 4180 and trocar thus create a tissue tunnel through subcutaneous tissue. In one method, a generally posterolateral approach is employed and the initial advancement of the needle 4180 and trocar positions the needle and trocar at the pedicle of the target vertebra. Advancement of the needle 4180 and trocar may be aided by fluoroscopy, e.g., using a C-arm or other similar technique.

After a percutaneous entry, or percutaneous entry path, has been created through the skin and subcutaneous tissue, the vertebral target site may be prepared, if desired. In one method, the needle 4180 and trocar are advanced further into the target vertebra at the vertebral target site to form a tunnel in the target vertebra. The tunnel may be formed in the pedicle and is sometimes referred to as a pedicle tunnel. Preferably a proximal end of the trocar remains outside the patient, above the skin puncture location throughout the target site preparation. Preparation of the vertebral target site may include further procedures, such as tapping of the pedicle tunnel, as discussed below.

Tapping creates threads in the pedicle tunnel that will mate with corresponding threads on an implant to be inserted later. In one method, the needle 4180 is advanced through intervening tissue to the surface of the target vertebra, but is not advanced into the vertebra. The trocar is advanced into the vertebra. Thereafter the trocar is removed and a tapping device is inserted through the needle to tap the hole created by the trocar. In another embodiment, the trocar is configured to further prepare a pedicle tunnel formed thereby, e.g., by having external threads configured to tap the pedicle tunnel. Tapping may be performed after the needle 4180 is withdrawn, as discussed further below.

In one method, the needle 4180 is advanced into the pedicle tunnel and is left in the pedicle tunnel of the target vertebra after the trocar is withdrawn from the needle 4180. Thereafter, a guidewire 4170, or other elongate body, may be inserted into the proximal end of the needle 4180. The guidewire 4170 may be advanced through the tissue tunnel and through the pedicle tunnel within the needle 4180. In one application, the guidewire 4170 is advanced until a distal end of the guidewire 4170 is located in the vertebral body of the target vertebra. The guidewire 4170 preferably extends proximally from of the skin and of the proximal end of the needle 4180 at the stage of the procedure illustrated in FIG. 67. After the stage illustrated in FIG. 67, the needle 4180 is removed leaving the guidewire 4170 in place, extending distally into the pedicle tunnel and proximally out of the skin.

As discussed above, it may be advantageous to prepare the pedicle tunnel by forming threads within the tunnel. One method of forming threads in the pedicle tunnel involves tapping the pedicle tunnel with a cannulated tap. A cannulated tap is a low profile instrument that has an elongate body and an outside surface. The elongate body extends between a proximal end and a distal end. A bore, or cannulation, is formed through the elongate body between the proximal and distal ends. The elongate body has formed thereon a structure configured to form internal threads within the pedicle tunnel, e.g., on the outer surface. The cannulated tap may be advanced over, e.g., slid over, the guidewire 4170 until the distal end is at the vertebral target site. Thereafter the cannulated tap may be rotated about the guidewire 4170 and advanced, turning the cannulated tap into the pedicle tunnel. As the cannulated tap advances the threads are formed in the pedicle tunnel.

In some applications, further dilation of the percutaneous access path or entry facilitates insertion of an implant. In one technique, a small incision is created at the skin puncture location. In one technique, an incision is created that is about 5-15 mm long. In some variations, an incision that is less than 5 mm can be created. The incision also can extend a distance into the tissue beneath the skin. The incision facilitates the insertion of one or more dilators over the wire to increase the size of the percutaneous access path or entry. The dilator may be advanced at least a substantial portion of the distance from the skin puncture location to the surface of the vertebra to reduce the resistance of the tissue beneath the skin to the insertion of an implant. The dilators are removed prior to insertion of an implant in one technique.

Although significant advantages are realized by preparing the vertebral target site prior to insertion of an access device, blood and other body fluids and tissues can hide or obscure the location of the prepared site. After the percutaneous access path or entry has been created, a marker may be delivered over the guidewire to the vertebral target site.

Figure 68:
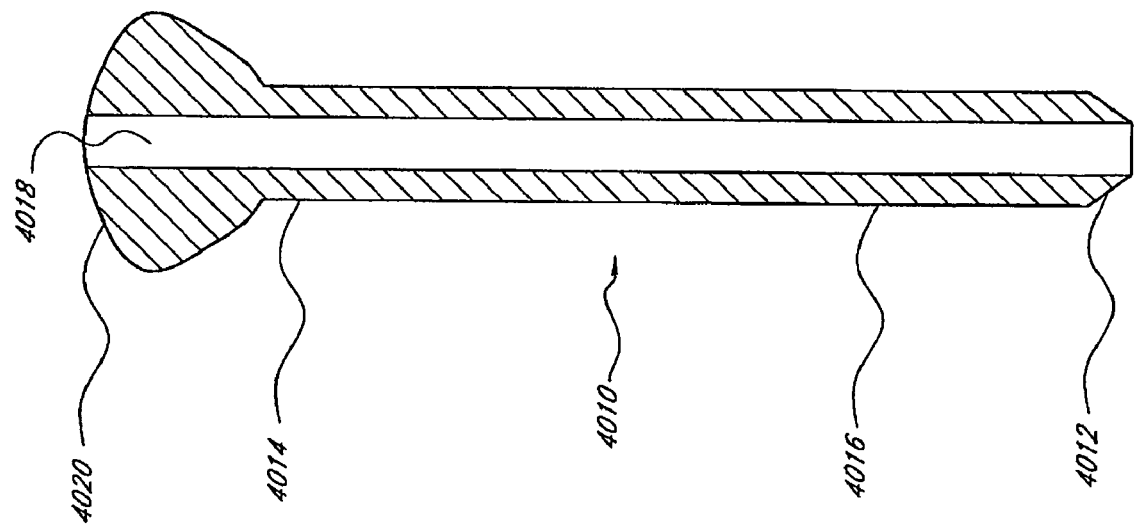
FIG. 68 is a sectional view of one embodiment of a marker configured to be delivered over a guidewire to a vertebra during a procedure.

FIG. 68 illustrates one embodiment of a marker 4010 that may be delivered percutaneously to the vertebral target site before an access device is inserted into the patient. The marker 4010 may be configured to be placed within a pedicle tunnel. Placing a marker within the pedicle tunnel aids the surgeon in finding the pedicle tunnel later in the procedure. The marker 4010 may include an elongated shaft 4016 having a distal end 4012 and a proximal end 4014. The marker 4010 also may include a head portion 4020 located at the proximal end 4014 of the shaft 4016. The shaft 4016 is generally slightly smaller in transverse size (e.g., circumference or cross-sectional area) than the pedicle tunnel. This facilitates sliding the marker 4010 into the tunnel. At least one of the shaft 4016 and a pedicle tunnel into which the shaft 4016 can be inserted is tapered, e.g., having a smaller transverse size near the distal end 4012 (or bottom of the tunnel) than near the proximal end 4014 (or near the top of the tunnel). Thus, a portion of the shaft 4016 may have a larger transverse size than a portion of the pedicle tunnel. The head portion 4020 enables insertion and removal of the marker 4010. For example, the cross-sectional area of at least a portion of the head portion 4020 exceeds the cross-sectional area of the shaft 4016. More particularly, the largest transverse size (e.g., circumference) of the head portion 4020 preferably is greater than the size of the proximal end of the pedicle tunnel such that at least a portion of the head portion 4020 of the marker 4010 remains outside the pedicle tunnel. The head portion 4020 may further be slotted, grooved, recessed, machined, or otherwise configured to engage a low profile instrument, such as a pusher or a driver, including, for example, a screwdriver, hex driver, or TORX driver. The head portion 4020 may be relatively short along the longitudinal axis of the marker 4010 so that the head portion 4020 does not extend too high above the vertebral target site. This arrangement enables an access device that may be deployed later in any of the methods to be positioned very close to the vertebrae being treated.

In one embodiment, a cannulation or bore 4018 is provided that extends from the distal end 4012 through the proximal end 4014 of the shaft 4016 and through the head portion 4020. The bore 4018 is configured to receive the guidewire 4170, as discussed below in connection with FIG. 69. In one embodiment, the exterior of the shaft 4016 is smooth to facilitate insertion and removal of the marker 4010. In another embodiment, the shaft 4016 has ridges or threads. The threads may be provided to more securely hold the marker 4010 within the pedicle tunnel or to further prepare the pedicle tunnel to receive a fastener, such as by tapping the pedicle tunnel.

Figure 69:
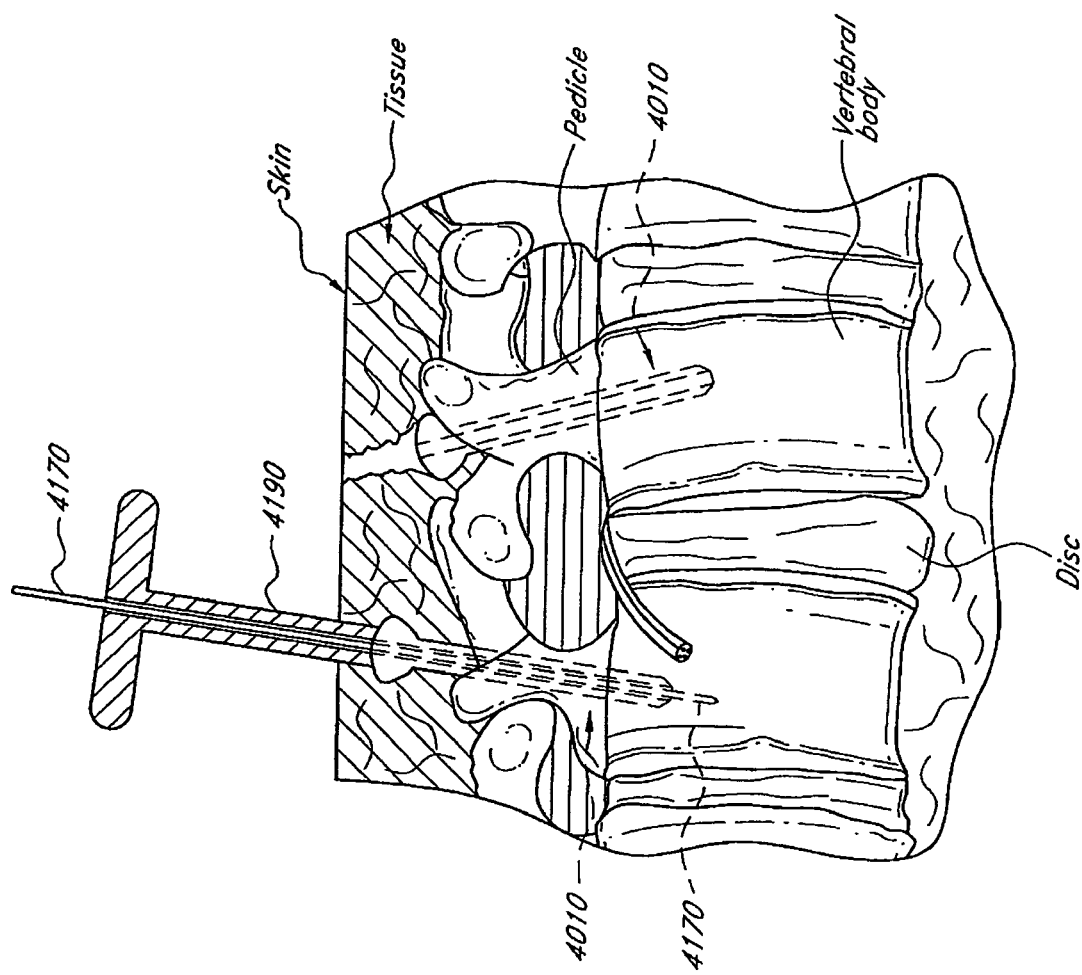
FIG. 69 is a schematic illustration of a method for percutaneously delivering a marker or other implant to a vertebra.

FIG. 69 is a schematic illustration of another stage of procedure that is later than the stage illustrated in FIG. 67. Prior to the stage illustrated in FIG. 69, the needle 4180 used to create the percutaneous entry is removed, leaving the guidewire 4170 in place. Thereafter, the marker 4010 is placed over the proximal end of the guidewire 4170 and advanced through the incision or the skin puncture location. The marker 4010 is thereafter advanced through the subcutaneous tissue to the vertebral target site (e.g., the pedicle). Depending on its configuration, the marker 4010 may be advanced with a cannulated inserter or a cannulated screwdriver 4190. In particular, if the marker 4010 is threaded, a cannulated screwdriver is preferred. Once the marker 4010 is advanced to the desired depth, the guidewire 4170 may be removed and the percutaneous portion of the procedure with respect to the first pedicle is complete Some procedures involve preparing vertebral target sites on adjacent vertebrae. For example, a one level fixation involves preparing target sites (e.g., forming pedicle tunnels) on two adjacent vertebrae. One technique for a two level fixation involves forming pedicle tunnels in the pedicles of three adjacent vertebrae. Accordingly, the foregoing steps discussed in connection with FIGS. 67 and 69 may be repeated for two or more adjacent pedicles to prepare the vertebral target sites and to mark the sites. FIGS. 67 and 69 show the second iteration of the foregoing steps, e.g., after a pedicle has been prepared and marked and while an adjacent pedicle is prepared and marked.

Figure 70:
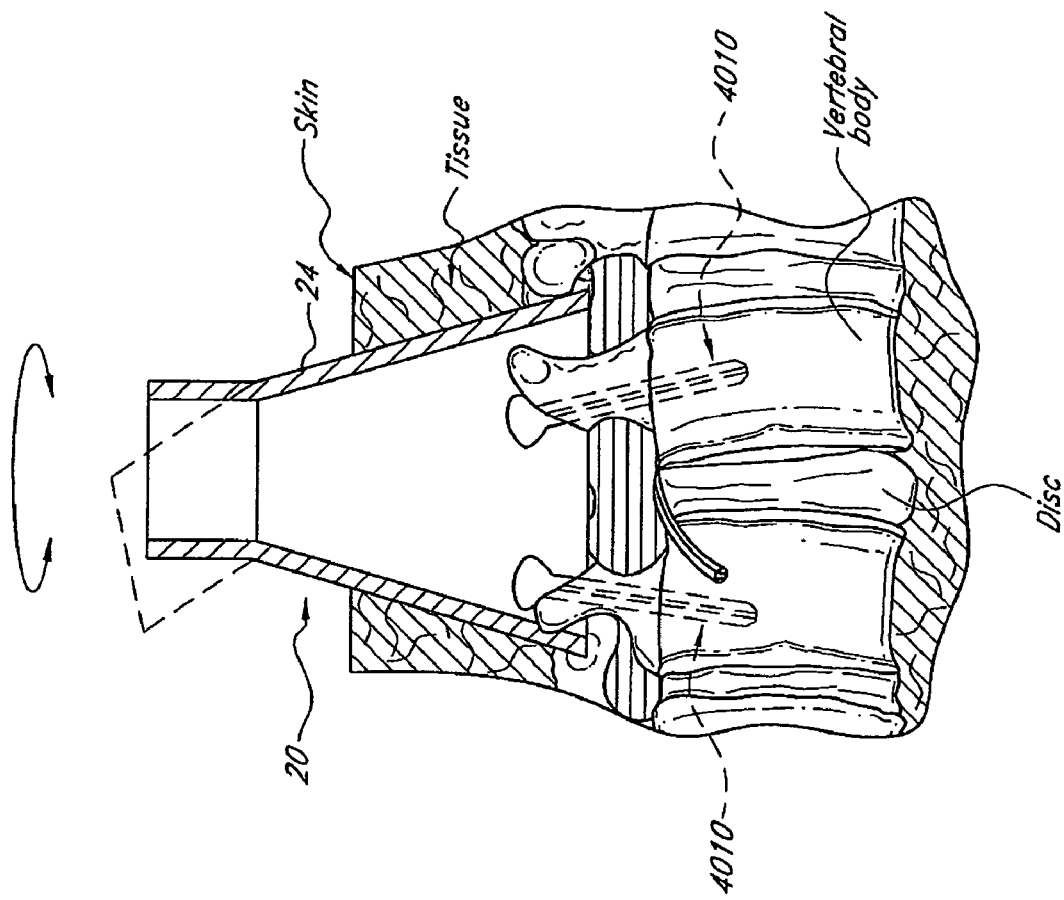
FIG. 70 is a schematic illustration of surgical procedure wherein an access device, such as that of FIG. 2, is deployed after an implant, such as a marker, has been delivered percutaneously to one or more vertebrae.

After adjacent pedicles have been marked, an access device is inserted into the patient to enclose one or more of the adjacent pedicles in a working space so that the minimally invasive portion of the procedure may be performed. In particular, an incision may be created by connecting, by extending, or by connecting and extending the incisions made for the guidewires. After the incision is made, the tissue may be dilated, as discussed above, and the access device or retractor inserted. The access device may be expanded so that the distal portion extends over one or more of the adjacent pedicles and the previously inserted markers 4010. An inserted and expanded access device is illustrated in FIG. 70.

Thereafter, any desired procedure, such as those described above may be performed in and around the working space. For example, the tissue adjacent to the markers 4010 may be debrided as desired. Also, decompression may be performed as desired, e.g., by removing bone in and around the vertebrae, e.g., above the spinal canal, in and around the foramen, etc. Where desired, a fusion may be performed, e.g., in, around, or in and around the interbody space.

After any other procedures have been performed, a fixation may be completed. Before other procedures are performed, the markers 4010 may be removed from the pedicle tunnels. Removal of the markers 4010 may be accomplished using a grasper or a torque applying tool (e.g., a screwdriver), as needed. If the pedicle tunnels have not already been tapped, as discussed above, they may be tapped at this stage. Prior to tapping, the pedicle tunnels may be probed to confirm their integrity. Any suitable technique can be employed to tap the pedicle tunnels after the access device has been deployed. In one variation, the pedicle tunnels may be tapped through the access device but not over a wire. In this technique, the marker 4010 (or a similar cannulated or non-cannulated marker) may be withdrawn in any suitable method. Thereafter, a tapping device is advanced through the access device (but not over a guidewire) to the vertebral target site. The tap is advanced into the pedicle tunnel to form threads therein. After the tapping device has formed the threads, the tapping device is removed from the access device and a fastener is advanced to and mated with each of the vertebral target sites. In this technique, a cannulated fastener or a non-cannulated fastener may be advanced into the pedicle tunnel.

Once the fasteners have been placed, a connecting member may be advanced through the access device along a longitudinal axis of the access device and then turned to span (e.g., to extend across) the fasteners. As discussed above, one-level, two-level, and more than two-level (e.g., three-level) procedures are contemplated. The connecting member may be a rigid element, such as a rigid rod or plate. In another embodiment, the connecting member is a flexible element that enables the adjacent vertebrae to maintain a degree of their natural range of motion. Additional structure related to flexible connecting elements and technique for application of such elements are set forth in U.S. patent application Ser. No. 10/693,815, filed Oct. 24, 2003, which is hereby incorporated herein by reference.

In some cases, other related procedures may thereafter be performed. For example, for some fixation procedures, bone graft material may be delivered to the vertebrae through the access device. For example, bone graft material may be placed around the fasteners and the connecting member to enhance the growth of bone between each of these elements and between these elements and the adjacent vertebrae.

A first alternative procedure is similar to that illustrated in FIGS. 67-70, except as set forth below. In the first alternative procedure, after an access device is deployed, guidewires 4170 are inserted back into pedicle tunnels (or tunnels formed at other vertebral target sites) through the markers 4010. Thereafter, the markers 4010 are withdrawn from the pedicle tunnels and out of the patient over the guidewires 4170. The pedicle tunnels are then prepared by delivering bone preparation instruments over the guidewire 4170. For example, a cannulated bone probe and a cannulated tap, such as the one described above, may be inserted separately over the guidewires 4170 and may be used to prepare the pedicle tunnels to receive the fasteners. After the pedicle tunnel has been tapped, the cannulated tap is removed. In another embodiment a combination probe and tap instrument is inserted over the guidewire to prepare the pedicle tunnels.

After the pedicle tunnels have been prepared, a cannulated fastener 4100, shown in FIG. 71 and discussed in greater detail below, may be delivered over the guidewires 4170 to the pedicle tunnels. The fasteners 4100 may be advanced into place using a cannulated screwdriver 4190. After the cannulated fastener 4100 is in place, the guidewire 4170 and cannulated screwdriver 4190 are removed from the patient. Thereafter, the fasteners 4100 may be coupled with a transverse member, such as a fixation member or a flexible element of a motion preserving member, as discussed above. Also, bone graft material may be delivered through the access device as desired.

In another variation, after a cannulated tap has been used to prepare the pedicle tunnel over a guidewire 4170, the guidewire 4170 is removed. Thereafter, a fastener is advanced through the access device but not over a guidewire. It may be advantageous to use a fastener that is not cannluated, e.g., a solid fastener in this technique. A cannulated fastener could also be used in this variation.

Figure 71:
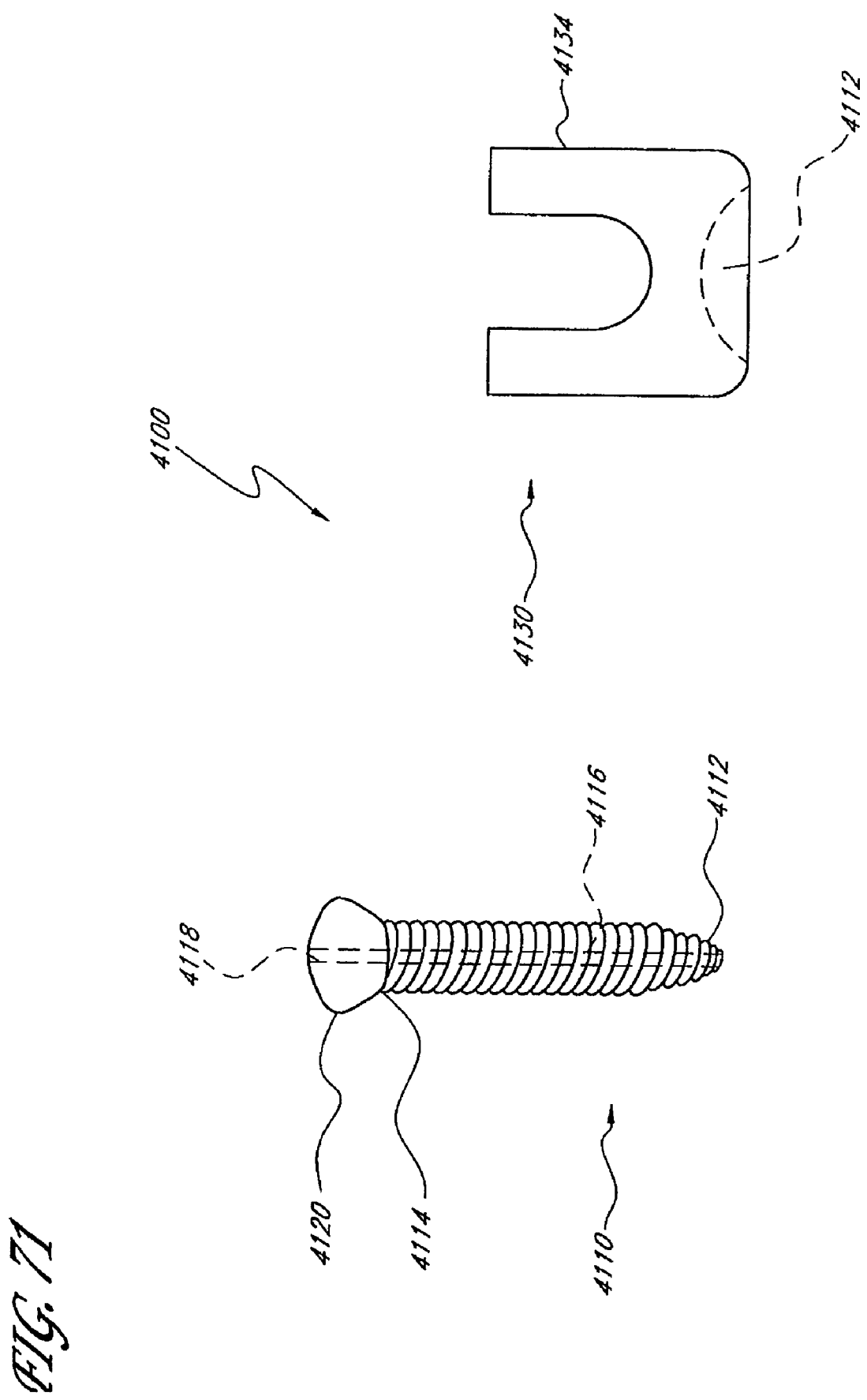
FIG. 71 is a side view of one embodiment of a fastener configured to be delivered over a guidewire to a vertebra.

FIG. 71 shows the fastener 4100 in greater detail. The fastener 4100 has an elongate engagement portion 4110 and a housing portion 4130. The engagement portion 4110 has an elongated shaft 4116 having a distal end 4112 and a proximal end 4114. In one embodiment the shaft 4116 tapers from a first cross sectional area at the distal end 4112 to a second cross sectional area at the proximal end 4114 that is greater than the first cross-sectional area. A head portion 4120 is coupled with the proximal end 4114 of the shaft 4116. The head portion 4120 may be configured for percutaneous delivery. For example, the head portion 4120 may be slotted, grooved, recessed, machined, or otherwise prepared to engage a driver such as a screwdriver, hex driver, or TORX driver.

A bore 4118 extends from the distal end 4112 through the proximal end 4114 of the shaft 4116 and through the head portion 4120. The bore 4118 is configured to receive a guidewire 4170, as discussed below in connection with FIG. 72. The exterior of the shaft 4116 preferably is threaded.

The housing portion 4130 is configured to be coupled with the head portion 4120. In one embodiment, the housing portion 4130 has a base portion 4132 that is recessed in a manner that corresponds with the shape of the head portion 4120. The housing portion 4130 also has a proximal portion 4134 that is substantially similar to the housing portion 604 discussed above in connection with FIG. 26. The elongate engagement portion 4110 is secured to the housing portion 4130 by seating the head portion 4120 in the base portion 4132. In one embodiment, the head portion 4120 snaps into the base portion 4132. In one embodiment, corresponding ridges extend around an outer surface of the head portion 4120 and around an inner surface of the housing portion 4130. The ridges are configured to engage each other to securely couple the housing portion 4130 to the head portion 4120. Thus, these components may be configured to be snapped together by the surgeon.

By making the housing portion 4130 and the elongate engagement portion 4110 of the fastener 4100 separable, a minimally invasive access device can be delivered very close to the vertebrae being treated. This is because the length of the fastener 4100 that extends above the vertebral target site is reduced when the housing portion 4130 is removed from the elongate engagement portion 4110. As a result, when the access device is expanded, deployed, or otherwise configured to provide a working space in the subcutaneous tissue between the skin and the vertebrae being treated, the separation between the distal end of the access device and the vertebral target site need not exceed the height of the head portion 4120 above the verebral target site. By keeping the access device close to the vertebral target site, encroachment of tissue into the working space is kept to a minimum and the vertebrae are made more clearly visible to the surgeon.

A second alternative approach to combining percutaneous and minimally invasive access involves delivery of at least a portion of a fastener percutaneously. The approach is similar to that discussed above in connection with FIGS. 68-70, except as discussed below in connection with FIG. 72.

Figure 72:
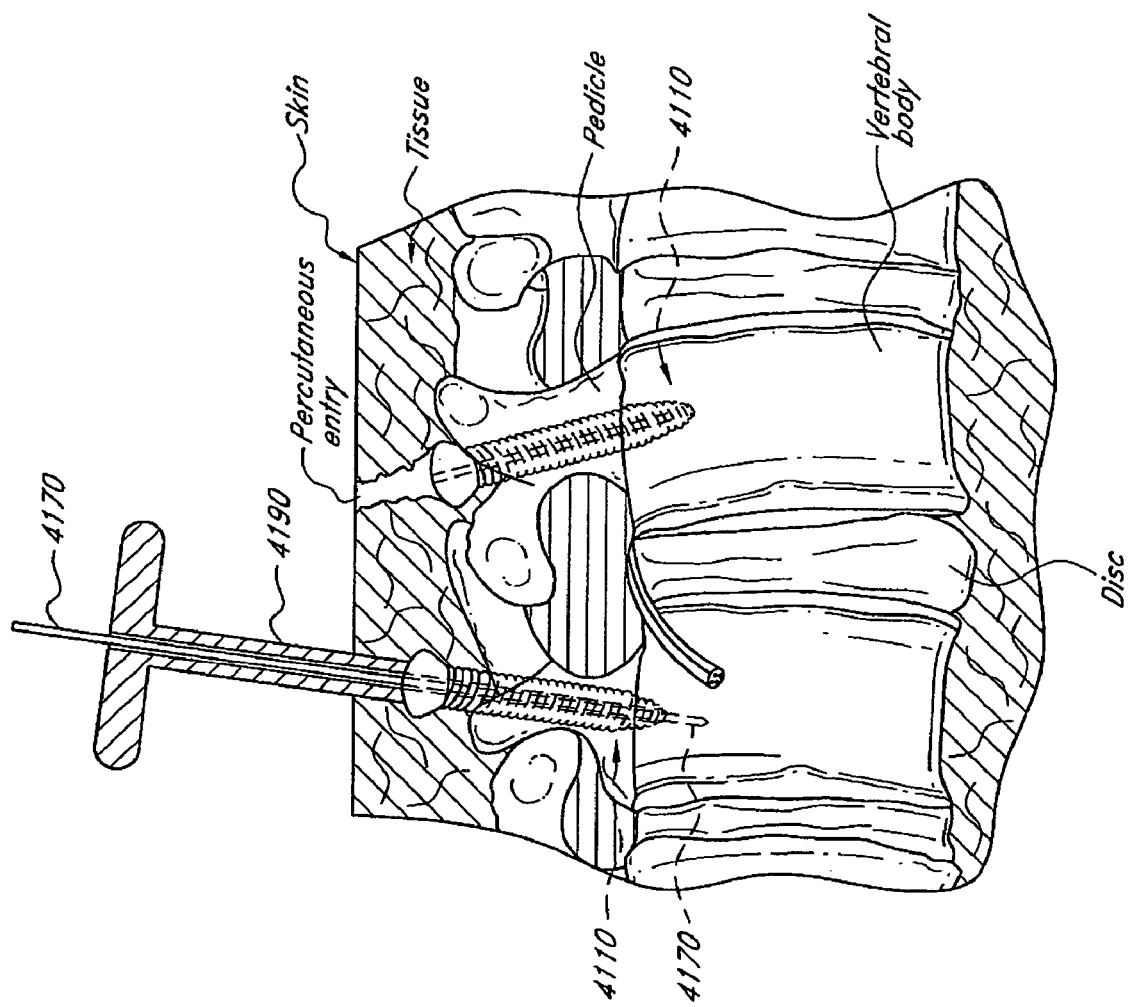
FIG. 72 is a schematic illustration of a method for percutaneously delivering an implant, such as the fastener of FIG. 71, to a vertebra.
Figure 73:
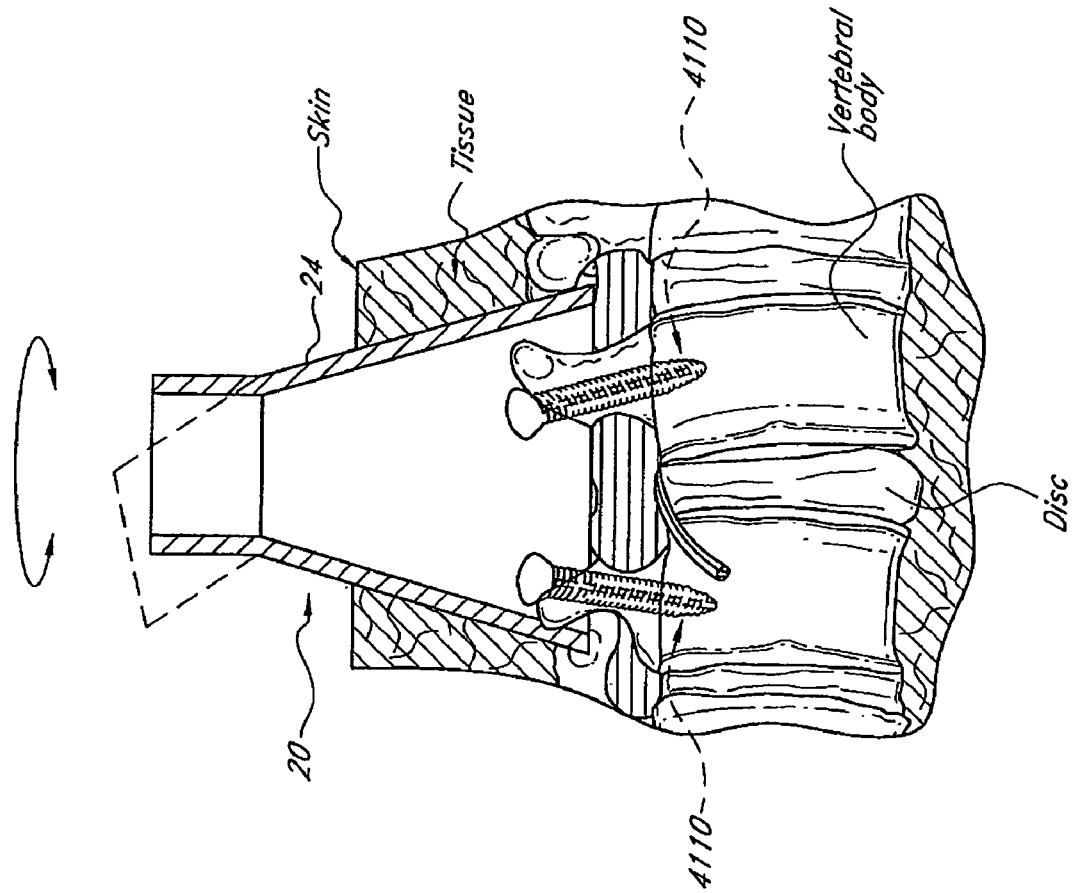
FIG. 73 is a schematic illustration similar to that of FIG. 70 wherein an access device is deployed after at least a portion of one or more fasteners has been delivered percutaneously.

FIG. 72 shows that the fastener 4100 may be inserted over a guidewire 4170 in a manner similar to the insertion of the marker 4010. The two piece arrangement of the fastener 4100 shown in FIG. 71 is advantageous in that the elongate engagement portion 4110 and the head portion 4120 are generally low profile and are cannulated, e.g., having a bore that extends therethrough. In other embodiments, a higher profile fastener (e.g., a one piece fastener or a fastener not requiring assembly during the procedure) can be used. Such fasteners may require slightly different introduction technique, such as greater dilation of the tissue tunnel formed between the skin puncture location and the vertebral target site. If the fastener 4100 is threaded, it may be desirable to prepare the pedicle tunnel, e.g., by tapping the tunnel, as discussed above. The pedicle tunnel (or a tunnel formed at another vertebral target site) can be prepared using cannulated instruments. After the tunnel is prepared, the fastener 4100 can be delivered over the guidewire 4170. If the fastener is threaded, it may be desirable to deliver the fastener 4100 using an instrument configured to apply a torque to the fastener 4100 in a manner similar to a screwdriver 4190.

After the elongate engagement portion 4110 has been delivered over the wire 4170, an access device may be deployed within the patient. Once the working space has been established within the access device, other procedures may be performed in connection with treating the spine, e.g., tissue debridement, decompression, and interbody fusion. Thereafter, the housing portion 4130 may be coupled with the head portion 4120 of the fastener 4100 in any suitable manner. For example, the housing portion 4130 and head portion 4120 may be snapped together, as discussed above. After the fastener 4100 has been fully assembled through the access device, a member, such as a fixation element or a flexible member, may be extended between adjacent fasteners 4100. Any other desired procedure may then be performed, such as external fusion.

In another alternative technique combining percutaneous and minimally invasive access, a vertebral target site is prepared. Percutaneous access is provided in the manner discussed above. In particular, a conventional technique is followed to identify a skin puncture location on the surface of the skin that corresponds to a target site on a target vertebra. The skin puncture location may be one that is directly above the vertebral target site or one that provides a suitable percutaneous access path (e.g., a path that avoids intervening anatomy) to the vertebral target site. As discussed above, a variety of approaches may be employed in spinal procedures. A procedure combining percutaneous access and minimally invasive access may be performed using any of these approaches. As discussed above, a posterolateral may be used in this variation.

A device configured to create a percutaneous entry or path is inserted through the skin. In one technique, a low-profile, sharp implement, such as a trocar, forms a percutaneous entry or path. The trocar or other implement may be advanced through the intervening tissues beneath the skin puncture location until a distal end of the trocar or other implement reaches the vertebral target site. As with the other techniques for forming percutaneous access paths described herein, the trocar or other instrument may be advanced using a visualization technique, such as fluoroscopy, e.g., with a C-arm, as discussed above. In this procedure, the trocar is not advanced within a needle or other hollow structure.

Once the trocar or other implement reaches the vertebral target site, the target site may be prepared by a suitable technique, such as those discussed above. For example, preparation of the vertebral target site may include forming a tunnel that extends from the surface of a pedicle (or other vertebral target site) into the pedicle and into the vertebral body. The pedicle tunnel preferably is somewhat smaller than an implant (e.g., the fastener 4100) to be inserted later, as discussed above. Other techniques for preparing the vertebral target site, such as probing and tapping, as discussed above, also may be employed.

After the vertebral target site is at least partially prepared, minimally invasive access may be provided by an access device, such as that of FIG. 2 discussed above, to provide a working space for the performance of additional procedures. The foregoing techniques for percutaneous vertebral target site preparation advantageously eliminate the need for preparing the target site while the access device is expanded, further reducing trauma to the patient and reducing recovery time associated with a procedure.

FIGS. 67-73 illustrate methods, procedures, and techniques performed at pedicle target sites. These methods, procedures, and techniques also can be performed at other surgical locations, e.g., other spinal locations. Such sites can include, among others, sites on facet joints and in inter-body spaces. For example, a transfacet fixation procedure can be performed by preparing tunnels at one or more target locations on or adjacent to a facet joint and by inserting markers into the tunnel(s) in a manner similar to the techniques described above relative to pedicle target locations. An access device can be deployed to provide a passage adjacent to the target locations. Fasteners can be inserted to the target locations, e.g., to stabilize the facet joint.

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

Incorporation by Reference

The entire disclosure of all of the following patents and patent applications is hereby incorporated by reference herein and made a part of this specification: PCT application no. PCT/US01/23999, filed Jul. 31, 2001, titled METHOD AND APPARATUS FOR SECURING VERTEBRAE, published as Publication WO 0209801 on Feb. 7, 2002; assignee's U.S. application Ser. No. 10/658,736, filed Sep. 9, 2003, titled METHODS AND APPRATUSES FOR TREATING THE SPINE THROUGH AN ACCESS DEVICE; U.S. provisional application No. 60/513,796, filed Oct. 22, 2003, titled ACCESS DEVICE FOR MINIMALLY INVASIVE SURGERY; U.S. provisional application Ser. No. 10/845,389, filed May 13, 2004, titled ACCESS DEVICE FOR MINIMALLY INVASIVE SURGERY; U.S. provisional application No. 60/514,559, filed Oct. 24, 2003, titled ACCESS DEVICE FOR MINIMALLY INVASIVE SPINAL SURGERY; U.S. application Ser. No. 10/969,788, filed Oct. 20, 2004, entitled INSTRUMENT FOR PREPARING A PORTION OF BONE TO RECEIVE AN IMPLANT (47A); U.S. Provisional Patent No. 60/579,643, filed Jun. 15, 2004, entitled ACCESS DEVICE HAVING A LOCKING MECHANISM (67PR2); U.S. application Ser. No. 11/094,822, filed Mar. 30, 2005, entitled SYSTEMS AND METHODS FOR PROVIDING ACCESS TO A SURGICAL LOCATION (50A); U.S. patent Ser. No. 10/842,651, filed May 10, 2004, entitled METHODS AND APPARATUSES FOR MINIMALLY INVASIVE REPLACEMENT OF INTERVERTEBRAL DISCS (30A); and U.S. patent Ser. No. 10/693,663, filed Oct. 24, 2003, entitled SYSTEM AND METHOD FOR IMPLANTING FACET SCREWS (33A).

What is claimed is:

1. A method for treating the spine, comprising:
   first, advancing a guidewire through the skin of a patient along a percutaneous path to a target location of a vertebra;
   second, advancing an implant over the guidewire to the target location of the vertebra, and coupling the implant with the vertebra at the target location;
   third, after coupling the implant with the vertebra, advancing an elongate body having a proximal end and a distal end until the distal end is adjacent the target location, the elongate body having an inner surface defining a passage extending therethrough, wherein a cross-sectional area of the passage at a first location is greater than a cross-sectional area of the passage at a second location, wherein the first location is distal to the second location; and
   fourth, performing a procedure at the target location.

2. The method of claim 1, wherein the implant comprises a marker.

3. The method of claim 2, further comprising:
   removing the marker; and
   advancing a fastener into the vertebra at the target location.

4. The method of claim 3, wherein the fastener is advanced over a guidewire.

5. The method of claim 3, wherein the fastener is advanced through the passage of the elongate body.

6. The method of claim 5, wherein the fastener is advanced over a guidewire.

7. The method of claim 2, further comprising:
   removing the guidewire before advancing the elongate body;
   inserting a guidewire through the marker after advancing the elongate body.

8. The method of claim 7, further comprising:
   removing the marker through the passage of the elongate body over the guidewire; and advancing a fastener to the target location over the guidewire.

9. The method of claim 2, further comprising:
   advancing a second marker over a second guidewire to a second target location on a second vertebra;
   coupling the second marker with the second vertebra; and
   positioning the elongate body such that the passage therethrough provides access to both the first and second target locations.

10. The method of claim 1, wherein the implant comprises an elongate portion of a fastener.

11. The method of claim 10, further comprising:
    advancing a housing portion of the fastener through the passage; and
    coupling the housing portion with the elongate portion of the fastener after the elongate body has been inserted into the patient.

12. The method of claim 11, wherein the fastener comprises a first fastener and the vertebra comprises a first vertebra and further comprising:
    advancing a second fastener to a second vertebra;
    coupling the second fastener with the second vertebra; and
    coupling a spanning member with the first fastener and with the second fastener.

13. The method of claim 12, further comprising:
    advancing a third fastener to a third vertebra;
    coupling the third fastener with the third vertebra; and
    coupling a spanning member with the second fastener and with the third fastener.

14. The method of claim 12, wherein the second fastener comprises an elongate portion and a housing portion and wherein the method of advancing the second fastener to the second vertebra comprises:
    advancing the elongate portion of the second fastener to a second vertebra;
    advancing the housing portion of the second fastener to the elongate portion of the second fastener; and
    coupling the housing portion of the second fastener to the elongate portion of the second fastener.

15. The method of claim 12, wherein the spanning member comprises a fixation element.

16. The method of claim 12, wherein the spanning member comprises a flexible element.

17. The method of claim 1, wherein performing a procedure comprises moving one vertebra relative to an adjacent vertebra in a cephalad-caudal direction.

18. The method of claim 1, wherein performing a procedure comprises moving one vertebra relative to an adjacent vertebra in an anterior-posterior direction.

19. The method of claim 1, wherein performing a procedure comprises debriding tissue.

20. The method of claim 1, wherein performing a procedure comprises performing an inter-body fusion.

21. The method of claim 1, wherein performing a procedure comprises delivering bone graft material.

22. A method for treating the spine, comprising:
    first, advancing a guidewire through the skin of a patient along a percutaneous path to a target location of a vertebra;
    second, advancing a cannulated implant over the guidewire to the target location of the vertebra;
    third, coupling the cannulated implant with the vertebra at the target location;
    fourth, removing the guidewire;
    fifth, advancing an elongate body having a proximal end and a distal end until the distal end is substantially adjacent the target location, the elongate body having an inner surface at least partially defining a passage extending therethrough, wherein a first transverse dimension of the elongate body at a first location is greater than a second transverse dimension the elongate body at a second location, the first location being distal to the second location; and sixth, performing a procedure at the target location through the passage of the elongate body.

23. A method for treating the spine, comprising:

first, percutaneously performing a first procedure at one or more target locations on the spine of a patient at least in part with the aid of a guidewire;

second, advancing a marking device over the guidewire to indicate the position of the target location;

third, advancing an elongate body until the distal end is adjacent the one or more target locations, the elongate body having an inner surface defining a passage extending therethrough, wherein a cross-sectional area of the passage at a first location is greater than a cross-sectional area of the passage at a second location, wherein the first location is distal to the second location; and fourth, performing a second procedure at the one or more target locations through the passage of the elongate body.

24. The method of claim 23, wherein the second procedure comprises a fixation procedure.

25. The method of claim 24, wherein the first procedure comprises preparing one or more target locations for the fixation procedure.

26. The method of claim 23, wherein the target location comprises an inter-body space, the first procedure comprises preparing the target location for insertion of a prosthetic disk, and the second procedure comprises inserting a prosthetic disk.

* * * * *

UNITED STATES PATENT AND TRADEMARK OFFICE
CERTIFICATE OF CORRECTION

| | | |
|---|---|---|
| PATENT NO. | : 7,651,496 B2 | Page 1 of 1 |
| APPLICATION NO. | : 11/184568 | |
| DATED | : January 26, 2010 | |
| INVENTOR(S) | : Thomas E. Keegan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Sixteenth Day of August, 2011

David J. Kappos
*Director of the United States Patent and Trademark Office*